(12) United States Patent
Keicher et al.

(10) Patent No.: US 7,534,771 B2
(45) Date of Patent: May 19, 2009

(54) TRICYCLIC-NUCLEOSIDE PRODRUGS FOR TREATING VIRAL INFECTIONS

(75) Inventors: Jesse Daniel Keicher, San Carlos, CA (US); Christopher Don Roberts, Belmont, CA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 282 days.

(21) Appl. No.: 11/365,170

(22) Filed: Feb. 28, 2006

(65) Prior Publication Data

US 2006/0194749 A1 Aug. 31, 2006

Related U.S. Application Data

(60) Provisional application No. 60/657,463, filed on Feb. 28, 2005.

(51) Int. Cl.
*A01N 43/04* (2006.01)
*A61K 31/70* (2006.01)
*C07H 19/00* (2006.01)
*C07H 19/056* (2006.01)

(52) U.S. Cl. ............... 514/43; 536/27.1; 536/28.1; 536/28.7

(58) Field of Classification Search .............. None
See application file for complete search history.

(56) References Cited

U.S. PATENT DOCUMENTS

| | | | |
|---|---|---|---|
| 4,107,288 | A | 8/1978 | Oppenheim et al. |
| 5,145,684 | A | 9/1992 | Liversidge et al. |
| 5,597,691 | A | 1/1997 | Houghton et al. |
| 5,738,985 | A | 4/1998 | Miles et al. |
| 5,739,002 | A | 4/1998 | De Francesco et al. |
| 5,759,795 | A | 6/1998 | Jubin |
| 5,861,267 | A | 1/1999 | Su |
| 6,030,785 | A | 2/2000 | Katze et al. |
| 6,228,576 | B1 | 5/2001 | DelVecchio |
| 7,268,119 | B2 * | 9/2007 | Cook et al. ........ 514/43 |
| 2005/0090463 | A1 | 4/2005 | Roberts et al. |
| 2006/0079468 | A1 | 4/2006 | Roberts et al. |
| 2006/0252715 | A1 | 11/2006 | Keicher et al. |

FOREIGN PATENT DOCUMENTS

| | | |
|---|---|---|
| WO | WO 97/12033 A1 | 4/1997 |
| WO | WO 98/43991 A1 | 10/1998 |
| WO | WO 01/90121 A2 | 11/2001 |
| WO | WO 02/18404 A2 | 3/2002 |
| WO | WO 02/057287 A2 | 7/2002 |
| WO | WO 02/057425 A2 | 7/2002 |
| WO | WO 03/061385 A1 | 7/2003 |
| WO | WO 2005/003147 A2 | 1/2005 |
| WO | WO 2005/021568 A2 | 3/2005 |
| WO | WO 2005/042556 A1 | 5/2005 |

OTHER PUBLICATIONS

U.S. Appl. No. 11/816,581, filed February 28, 2006, Roberts et al.
U.S. Appl. No. 11/839,380, filed February 28, 2006, Keicher et al.
Bartholomeusz, et al., "Hepatitis C Virus (HCV) RNA polymerase assay using cloned HCV non-structural proteins." Antiviral Therapy, 1996, 1 (supp. 4):18-24.
Beaulieu, et al., "Inhibitors of the HCV NS5B polymerase: new hope for the treatment of hepatitis C infections." Curr. Opin. Investig. Drugs 2004, 5(8):838-850.
Cooperwood, et al., "Nucleoside and Nucleotide prodrugs" in Ed(s) Chu, C. K. Recent Advances in Nucleosides 2002, 92-147.
Cruickshank, et al., "Oligonucleotide labeling: A concise synthesis of a modified thymidine phosphoramidite." Tet. Lett., 1988, 29(41), 5221-24.
Ferrari et al., "Characterization of soluble hepatitis C virus RNA-dependent RNA polymerase expressed in *Escherichia coli*." J. Virol., 1999, 73:1649-1654.
Fried, et al., "Peginterferon alfa-2a plus ribavirin for chronic hepatitis C virus infection." N. Engl. J. Med., 2002, 347(13):975-982.
Griffith, et al., "HCV Antiviral Agents." Ann. Rep. Med. Chem. 2004, 39:223-237.
Harper, et al., "Potent inhibitors of subgenomic hepatitis C virus RNA replication through optimization of indole-N-acetamide allosteric inhibitors of the viral NS5B polymerase." J. Med. Chem., 2005, 48, 4547-57.
Hoofnagle, "Hepatitis C: the clinical spectrum of disease." Hepatology 1997, 26:15S-20S.
Horsmans, et al., "Isatoribine, an agonist of TLR7, reduces plasma virus concentration in chronic hepatitis C infection." Hepatology, 2005, 42:724-731.
Hutchinson, (Ed. Leroy B. Townsend) "The Synthesis, Reaction and Properties of Nucleoside Mono-, Di-, Tri-, and Tetraphosphates and Nucleosides with Changes in the Phosphoryl Residue" Chemistry of Nucleosides and Nucleotides, Plenum Press, 1991, 2.
Ishii et al., "Expression of hepatitis C virus NS5B protein: characterization of its RNA polymerase activity and RNA binding." Hepatology, 1999, 29: 1227-1235.
Lohmann et al., "Selective Stimulation of Hepatitis C Virus and Pestivirus NS5B RNA Polymerase Activity by GTP." J. Bio. Chem., 1999, 274(16):10807-10815.
Lohmann, et al., "Replication of subgenomic hepatitis C virus RNAs in a hepatoma cell line." Science, 1999, 285:110-113.
Love, et al., "Crystallographic identification of a noncompetitive inhibitor binding site on the hepatitis C virus NS5B RNA polymerase enzyme." J. Virol. 2003, 77(13):7575-7581.
Mandal, et al., "Stereospecific C-β-glycosidation and synthesis of 4,7-anhydro-5,6-isopropylidene-4(S), 5(S), 6(R), 7(R)-tetrahydroxyoxocan-2-one" Synth. Commun., 1993, 23(9):1239-1244.
Meier., "Pro-Nucleotides—recent advances in the design of efficient tools for the delivery of biologically active nucleoside monophosphates" Synlett 1998, 3, 233-42.

(Continued)

*Primary Examiner*—Traviss C McIntosh, III
(74) *Attorney, Agent, or Firm*—Junrui Yang

(57) ABSTRACT

Disclosed are compounds, compositions and methods for treating viral infections caused by a Flaviviridae family virus, such as hepatitis C virus.

32 Claims, No Drawings

OTHER PUBLICATIONS

Moriishi et al., "Mechanisms of hepatitis C virus infection." Antivir. Chem. Chemother. 2003, 14:285-297.

Ni et al., "Progress and development of small molecule HCV antivirals," Curr. Opin. Drug Discov. Devel. 2004, 7(4):446-459.

Ning, et al., "Syntheses and reactions of 5-O-acetyl-1,2-anhydro-3-O-benzyl-α-D-ribofuranose and β-D-lyxofuranose, 5-O-acetyl-1,2-anhydro-3,6-di-O-benzyl- and 1,2-anhydro-5,6-di-O-benzoyl-3-O-benzyl-β-D-mannofuranose, and 6-O-acetyl-1,2-anhydro-3,4-di-O-benzyl-α-D-glucopyranose and -β-D-talopyranose." Carbohydr. Res., 2001, 330, 165-175.

Olsen, et al., "A 7-deaza-adenosine analog is a potent and selective inhibitor of hepatitis C virus replication with excellent pharmacokinetic properties" Antimicrob. Agents Chemother. 2004, 48(10), 3944-53.

Sarisky., "Non-nucleoside inhibitors of the HCV polymerase." J. Antimicrob. Chemother. 2004, 54, 14-16.

Saunders, et al., "Inosine Monophosphate Dehydrogenase: Consideration of Structure, Kinetics and Therapeutic Potential." Ann. Rep. Med. Chem., 2000, 35, 201-10.

Seela, et al., "7-substituted-7-deaza-2'-deoxyadenosines and 8-aza-7-deaza-2'-deoxyadenosines: fluorescence of DNA-base analogs induced by the 7-alkynyl side chain" Helvetica Chimica Acta, 2000, 83, 910-927.

Szabo, et al., "Viral hepatitis: new data on hepatitis C infection." Pathol. Oncol. Res. 2003, 9(4):215-221.

Thomson et al., "Hepatitis C infection." Clin Microbial Infect. 2005, 11:86-94.

Wagner, et al., "Pronucleotides: Toward the in vivo delivery of antiviral and anticancer nucleotides." Medicinal Research Reviews 2000, 20(6), 417-451.

Watashi, et al., "Cyclophilin B is a functional regulator of hepatitis C virus RNA polymerase." Molecular Cell, 2005,19, 111-122.

Witty, et al., "Ring contraction of 2-O-trifluoromethanesulphonates of α-hydroxy-γ-lactones to oxetane carboxylic esters." Tet. Lett., 1990, 31(33), p. 4787-4790.

Yamashita et al., "RNA-dependent RNA Polymerase Activity of the Soluble Recombinant Hepatitis C Virus NS5B Protein Truncated at the C-terminal Region." J. Bio. Chem., 1998, 273(25), 15479-15486.

Zemlicka, et al., "Lipophilic phosphoramidates as antiviral pronucleotides." Biochimica et Biophysica Acta 1587, 2002, (2-3), 276-286.

* cited by examiner

TRICYCLIC-NUCLEOSIDE PRODRUGS FOR TREATING VIRAL INFECTIONS

CROSS-REFERENCE TO RELATED APPLICATION

This application claims the benefit under 35 U.S.C. 119(e) to co-pending provisional application U.S. Ser. No. 60/657,463 filed on Feb. 28, 2005, which is incorporated herein by reference in its entirety.

BACKGROUND OF THE INVENTION

1. Field of the Invention

The invention relates to the field of pharmaceutical chemistry, in particular to compounds, compositions and methods for treating viral infections in mammals mediated, at least in part, by a virus in the Flaviviridae family of viruses.

REFERENCES

The following publications are cited in this application as superscript numbers:

1. Szabo, et al., *Pathol Oncol. Res.* 2003, 9:215-221.
2. Hoofnagle J H, *Hepatology* 1997, 26:15S-20S.
3. Thomson B J and Finch R G, *Clin Microbial Infect.* 2005, 11:86-94.
4. Moriishi K and Matsuura Y, *Antivir. Chem. Chemother.* 2003, 14:285-297.
5. Fried, et al. *N. Engl. J Med* 2002, 347:975-982.
6. Ni, Z. J. and Wagman, A. S. *Curr. Opin. Drug Discov. Devel.* 2004, 7, 446-459.
7. Beaulieu, P. L. and Tsantrizos, Y. S. *Curr. Opin. Investig. Drugs* 2004, 5, 838-850.
8. Griffith, et al., *Ann. Rep. Med. Chem* 39, 223-237, 2004.
9. Sommadossi, et al., International Patent Application Publication No. WO01/90121, published May 23, 2001
10. Olson et al., *Antimicrob Agents Chemother.* 2004, 48:3944-53
11. Sarisky R. T. *J Antimicrob Chemother.* 2004, 54:14-6
12. Love et al., *J Virol.* 2003, 77:7575-81
13. Harper et al., J Med Chem. 2005, 48:4547-57
14. Hiromasa et al., U.S. Pat. No. 6,770,666 issued Aug. 3, 2004
15. Watashi, et al, Molecular Cell, 19, 111-122, 2005
16. Horsmans, et al., Hepatology, 42, 724-731, 2005
17. Carroll, S. S., et al., International Patent Application Publication No. WO 02/057287, published 25 Jul. 2002;
18. Carroll, S. S., et al., International Patent Application Publication No. WO 02/057425, published 25 Jul. 2002.

All of the above publications are herein incorporated by reference in their entirety to the same extent as if each individual publication was specifically and individually indicated to be incorporated by reference in its entirety.

2. State of the Art

Chronic infection with HCV is a major health problem associated with liver cirrhosis, hepatocellular carcinoma and liver failure. An estimated 170 million chronic carriers worldwide are at risk of developing liver disease.[1,2] In the United States alone 2.7 million are chronically infected with HCV, and the number of HCV-related deaths in 2000 was estimated between 8,000 and 10,000, a number that is expected to increase significantly over the next years. Infection by HCV is insidious in a high proportion of chronically infected (and infectious) carriers who may not experience clinical symptoms for many years. Liver cirrhosis can ultimately lead to liver failure. Liver failure resulting from chronic HCV infection is now recognized as a leading cause of liver transplantation.

HCV is a member of the Flaviviridae family of RNA viruses that affect animals and humans. The genome is a single ~9.6-kilobase strand of RNA, and consists of one open reading frame that encodes for a polyprotein of ~3000 amino acids flanked by untranslated regions at both 5' and 3' ends (5'- and 3'-UTR). The polyprotein serves as the precursor to at least 10 separate viral proteins critical for replication and assembly of progeny viral particles. The organization of structural and non-structural proteins in the HCV polyprotein is as follows: C-E1-E2-p7-NS2-NS3-NS4a-NS4b-NS5a-NS5b. Because the replicative cycle of HCV does not involve any DNA intermediate and the virus is not integrated into the host genome, HCV infection can theoretically be cured. While the pathology of HCV infection affects mainly the liver, the virus is found in other cell types in the body including peripheral blood lymphocytes.[3,4]

At present, the standard treatment for chronic HCV is interferon alpha (IFN-alpha) in combination with ribavirin and this requires at least six (6) months of treatment. IFN-alpha belongs to a family of naturally occurring small proteins with characteristic biological effects such as antiviral, immunoregulatory and antitumoral activities that are produced and secreted by most animal nucleated cells in response to several diseases, in particular viral infections. IFN-alpha is an important regulator of growth and differentiation affecting cellular communication and immunological control. Treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction. Ribavirin, an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha (IFN) and ribavirin. By now, standard therapy of chronic hepatitis C has been changed to the combination of pegylated IFN-alpha plus ribavirin. However, a number of patients still have significant side effects, primarily related to ribavirin. Ribavirin causes significant hemolysis in 10-20% of patients treated at currently recommended doses, and the drug is both teratogenic and embryotoxic. Even with recent improvements, a substantial fraction of patients do not respond with a sustained reduction in viral load[5] and there is a clear need for more effective antiviral therapy of HCV infection.

A number of approaches are being pursuit to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. Among the viral targets, the NS3/4A protease/helicase and the NS5b RNA-dependent RNA polymerase are considered the most promising viral targets for new drugs.[6,8]

The NS5b RNA-dependent RNA polymerase in particular has been shown to be amenable to small-molecule inhibition. Besides several nucleoside inhibitors,[9,10] at least three allosteric sites have been described,[7] along with multiple inhibitor scaffolds.[11,14]

Besides targeting viral genes and their transcription and translation products, antiviral activity can also be achieved by targeting host cell proteins that are necessary for viral replication. For example, Watashi et al.[15] show how antiviral activity can be achieved by inhibiting host cell cyclophilins. Alternatively, a potent TLR7 agonist has been shown to reduce HCV plasma levels in humans.[16]

However, none of the compounds described above have progressed beyond clinical trials.[6,8]

In view of the worldwide epidemic level of HCV and other members of the Flaviviridae family of viruses, and further in view of the limited treatment options, there is a strong need for new effective drugs for treating infections cause by these viruses.

SUMMARY OF THE INVENTION

This invention is directed to novel compounds that are useful in the viral infections in mammals, mediated at least in part by a virus in the Flaviviridae family of viruses. In one of its composition aspects, the present invention is directed to compounds of Formula I:

I wherein
----- between $Z^1$ and $Z^2$, between $Z^2$ and $Z^3$, between $Z^4$ and $R^1$, and between N and $Z^4$ indicates a bond that may be a single or a double bond and ---- indicates a single bond or no bond, provided that:

only one of the bonds between $Z^1$ and $Z^2$ and between $Z^2$ and $Z^3$ is a double bond;

when the bond between $Z^4$ and $R^1$ is a double bond, the bond between the N and $Z^4$ is a single bond, the bond between the N and $(R)_p$ is a single bond and p is 1;

when the bond between $Z^4$ and $R^1$ is a single bond, the bond between the N and $Z^4$ atoms is a double bond, the bond between the N and $(R)_p$ is absent and p is 0;

p is 0 or 1;

each R is independently selected from hydrogen, alkyl, substituted alkyl, cycloalkyl, substituted cycloalkyl;

when the bond between $Z^4$ and $R^1$ is a single bond, then $R^1$ is selected from the group consisting of hydrogen alkyl, substituted alkyl, alkoxy, substituted alkoxy, thiol, and alkylthioether;

when the bond between $Z^4$ and $R^1$ is a double bond, then $R^1$ is $Q^1$;

each of $Z^1$, $Z^2$ and $Z^3$ is independently selected from the group consisting of CH, CH$_2$, CH-Q$^4$, C-Q$^4$, C(Q$^1$), N, N—H, and N-Q provided that if one of $Z^1$, or $Z^3$ is CH, N or C-Q$^4$ then $Z^2$ is CH or N or C-Q$^4$;

$Z^4$ is a carbon atom containing a double bond either with $R^1$ or with N;

Q is selected from the group consisting of alkyl and substituted alkyl;

$Q^1$ is =O or =S;

$Q^3$ is selected from the group consisting of OH, alkyl, substituted alkyl, amino, and substituted amino;

$Q^4$ is selected from the group consisting of halo, cyano, azido, amino, substituted amino, alkyl, substituted alkyl, alkenyl, substituted alkenyl, alkynyl, substituted alkynyl, acyl, acyloxy, carboxyl, carboxyl ester, acylamino, aminoacyl, alkoxy, substituted alkoxy, thiol, alkylthioether and —SO$_2$-Q$^3$;

Y is selected from the group consisting of a bond, —CH$_2$— or —O—; and

X is selected from the group consisting of O—W$^2$ and halo;

each of W, W$^1$ and W$^2$ is independently selected from the group consisting of hydrogen, C$_{1-4}$alkyl, and a pharmaceutically acceptable prodrug group;

or pharmaceutically acceptable tautomers, salts or partial salts thereof;

provided that at least one of W$^1$ and W$^2$ is a pharmaceutically acceptable prodrug group; and further provided that said compound, tautomer, salt, or partial salt is not represented by formula II or III or a tautomer, salt, or partial salt thereof

II

III wherein:
Q' is absent or is selected from the group consisting of O, S, and NH, provided that when Q' is absent, V and NH are both attached to a CH$_2$ group;

V is selected from the group consisting of N and C-G;

Z is selected from the group consisting of N and C-G';

V and Z are not identical;

G and G' are independently selected from the group consisting of hydrogen, amino, aminocarbonyl, methylamino, dimethylamino, acylamino, alkoxyamino, —SO$_3$H, —SO$_2$NH$_2$, aminocarbonylamino, oxycarbonylamino, HR'NCHR"C(O)NH—, azido, cyano, halo, hydroxyamino, and hydrazino where R' is hydrogen and R" is a side-chain of an amino acid or where R' and R" together with the nitrogen and carbon bound to each group respectively form a pyrrolidinyl group;

A and B are independently selected from the group consisting of C=Q", NH, and methylene optionally substituted with 1 to 2 halo groups, provided that A and B are not both NH;

D is NH, or -D-A-B— together form a —N=CH—NH—, —(C=Q")-CH$_2$—(C=Q")-, —(C=Q")-NH—(C=Q")-, —(CX')—(CX')—(C=Q")-, or —CH=CH—NH— group where X' is halo;

each Q" is independently selected from the group consisting of O, S, and NH;

$T^1$ and $T^2$ are independently selected from the group consisting of hydrogen, hydroxyl, $C_1$-$C_4$-alkoxy, $C_1$-$C_4$-thioalkoxy, amino, substituted amino, and halo; and W, $W^1$, Y and X are as defined for formula I.

In another of its composition aspects, the present invention is directed to compounds of Formula Ia:

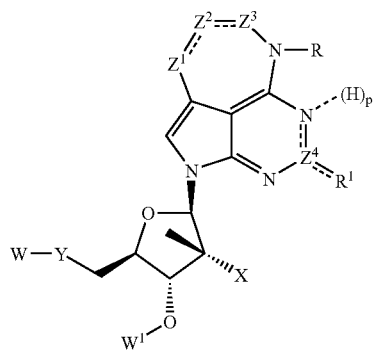

Ia wherein
⚏⚏⚏⚏ between $Z^1$ and $Z^2$, between $Z^2$ and $Z^3$, between $Z^4$ and $R^1$, and between N and $Z^4$ indicates a bond that may be a single or a double bond and ----- indicates a single bond or no bond, provided that:

only one of the bonds between $Z^1$ and $Z^2$ and between $Z^2$ and $Z^3$ is a double bond;

when the bond between $Z^4$ and $R^1$ is a double bond, the bond between the N and $Z^4$ is a single bond, the bond between the N and $(H)_p$ is a single bond and p is 1;

when the bond between $Z^4$ and $R^1$ is a single bond, the bond between the N and $Z^4$ atoms is a double bond, the bond between the N and $(H)_p$ is absent and p is 0;

p is 0 or 1;

R is selected from hydrogen, alkyl, substituted alkyl, cycloalkyl, substituted cycloalkyl;

when the bond between $Z^4$ and $R^1$ is a single bond, then $R^1$ is selected from the group consisting of hydrogen, alkyl, substituted alkyl, alkoxy, substituted alkoxy, thiol, alkylthioether;

when the bond between $Z^4$ and $R^1$ is a double bond, then $R^1$ is $Q^1$;

$Z^1$ is selected from the group consisting of CH, CH$_2$, CH-$Q^4$, C-$Q^4$, C($Q^1$), N, NH, N-Q $Z^2$ is selected from the group consisting of CH, CH$_2$, C($Q^1$);

$Z^3$ is selected from the group consisting of CH, CH$_2$, C($Q^1$);

provided that if $Z^1$ is CH, N or C-$Q^4$ or if $Z^3$ is CH then $Z^2$ is CH;

$Z^4$ is a carbon atom containing a double bond either with $R^1$ or with N;

Q is selected from the group consisting of alkyl and substituted alkyl;

$Q^1$ is =O or =S;

$Q^4$ is selected from the group consisting of halo, cyano, azido, amino, substituted amino, alkyl, substituted alkyl, alkenyl, substituted alkenyl, alkynyl, substituted alkynyl, acyl, acyloxy, carboxyl, carboxyl ester, acylamino, aminoacyl, alkoxy, substituted alkoxy, thiol, alkylthioether and —SO$_2$-$Q^3$, where $Q^3$ is OH, alkyl, substituted alkyl, amino, or substituted amino;

Y is selected from the group consisting of a bond, —CH$_2$— or —O—; and

X is selected from the group consisting of O—$W^2$ and halo;

each of W, $W^1$ and $W^2$ is independently selected from the group consisting of hydrogen, $C_{1-4}$alkyl, and a pharmaceutically acceptable prodrug group;

or pharmaceutically acceptable tautomers, salts or partial salts thereof;

provided that at least one of $W^1$ and $W^2$ is a pharmaceutically acceptable prodrug group; and further provided that said compound, tautomer, salt, or partial salt is not represented by formula II or III or a tautomer, salt, or partial salt thereof

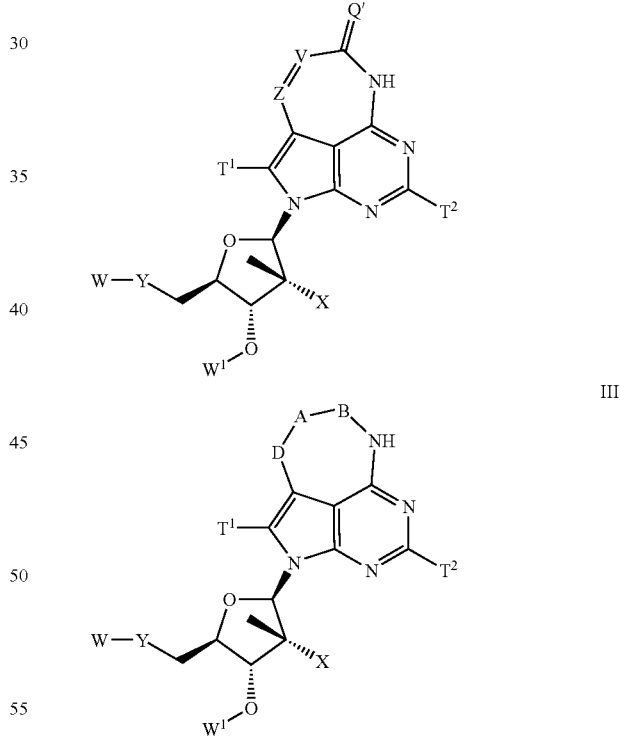

wherein:

Q' is absent or is selected from the group consisting of O, S, and NH, provided that when $Q^1$ is absent, V and NH are both attached to a CH$_2$ group;

V is selected from the group consisting of N and C—G;

Z is selected from the group consisting of N and C—G';

V and Z are not identical;

G and G' are independently selected from the group consisting of hydrogen, amino, aminocarbonyl, methylamino, dimethylamino, acylamino, alkoxyamino, —SO$_3$H, —SO$_2$NH$_2$, aminocarbonylamino, oxycarbonylamino, HR'NCHR"C(O)NH—, azido, cyano, halo, hydroxyamino, and hydrazino where R' is hydrogen and R" is a side-chain of an amino acid or where R' and R" together with the nitrogen and carbon bound to each group respectively form a pyrrolidinyl group;

A and B are independently selected from the group consisting of C=Q", NH, and methylene optionally substituted with 1 to 2 halo groups, provided that A and B are not both NH;

D is NH, or -D-A-B— together form a —N=CH—NH', —(C=Q")-CH$_2$—(C=Q")-, —(C=Q")-NH—(C=Q")-, —(CX')=(CX')'(C=Q")-, or —CH=CH—NH— group where X' is halo;

each Q" is independently selected from the group consisting of O, S, and NH;

T$^1$ and T$^2$ are independently selected from the group consisting of hydrogen, hydroxyl, C$_1$-C$_4$-alkoxy, C$_1$-C$_4$-thioalkoxy, amino, substituted amino, and halo; and W, W$^1$, Y and X are as defined for formula I.

In another of its composition aspects, the present invention is directed to compounds of Formula Ib:

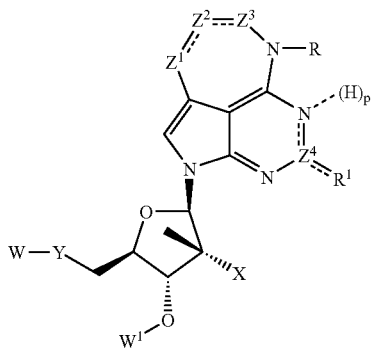

Ib wherein

-----between Z$^1$ and Z$^2$, between Z$^2$ and Z$^3$, between Z$^4$ and R$^1$, and between N and Z$^4$ indicates a bond that may be a single or a double bond and ----indicates a single bond or no bond, provided that:

only one of the bonds between Z$^1$ and Z$^2$ and between Z$^2$ and Z$^3$ is a double bond;

when the bond between Z$^4$ and R$^1$ is a double bond, the bond between the N and Z$^4$ is a single bond, the bond between the N and (H)$_p$ is a single bond and p is 1;

when the bond between Z$^4$ and R$^1$ is a single bond, the bond between the N and Z$^4$ atoms is a double bond, the bond between the N and (H)$_p$ is absent, and p is 0;

p is 0 or 1;

R is hydrogen;

when the bond between Z$^4$ and R$^1$ is a single bond, then R$^1$ is selected from the group consisting of hydrogen, alkyl, alkoxy, and alkylthioether;

when the bond between Z$^4$ and R$^1$ is a double bond, then R$^1$ is =O;

Z$^1$ is selected from the group consisting of CH, CH$_2$, C-Q$^5$, C—CN, C—N$_3$, C—OH, C—SH, C—O-alkyl, C—S-alkyl, C—SO$_2$-Q$^3$, CC≡C-Q$^2$, C(Q$^1$); C—NH$_2$, C—NHCH$_3$, C—N(CH$_3$)$_2$, N, and NH;

Z$^2$ is selected from the group consisting of CH, CH$_2$, C(Q$^1$);

Z$^3$ is selected from the group consisting of CH, CH$_2$, C(Q$^1$);

provided that if Z$^1$ is CH, C—CN, C—N$_3$, C—O—C(O)CH$_3$, C—OH, C—SH, —C—O-alkyl, C—SO$_2$-Q$^3$, CC≡C-Q$^2$, CNH$_2$, CNHCH$_3$, C—N(CH$_3$)$_2$ or N or if Z$^3$ is CH then Z$^2$ is CH;

Z$^4$ is a carbon atom containing a double bond either with R$^1$ or with N;

Q$^1$ is O or S;

Q$^2$ is hydrogen, alkyl;

Q$^3$ is OH, NH$_2$, or alkyl;

Q$^5$ is halo;

Y is selected from the group consisting of a bond, —CH$_2$— or —O—; and

X is selected from the group consisting of O—W$^2$ and halo;

each of W, W$^1$ and W$^2$ is independently selected from the group consisting of hydrogen, C$_{1-4}$alkyl, and a pharmaceutically acceptable prodrug group;

or pharmaceutically acceptable tautomers, salts or partial salts thereof;

provided that at least one of W$^1$ and W$^2$ is a pharmaceutically acceptable prodrug group; and further provided that said compound, tautomer, salt, or partial salt is not represented by formula II or III or a tautomer, salt, or partial salt thereof

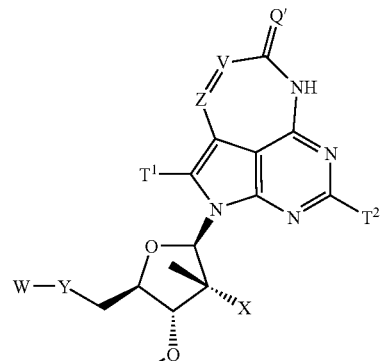

II

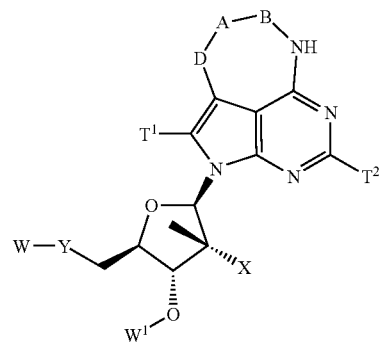

III wherein:

Q' is absent or is selected from the group consisting of O, S, and NH, provided that when Q' is absent, V and NH are both attached to a CH$_2$ group;

V is selected from the group consisting of N and C-G;

Z is selected from the group consisting of N and C-G';

V and Z are not identical;

G and G' are independently selected from the group consisting of hydrogen, amino, aminocarbonyl, methylamino, dimethylamino, acylamino, alkoxyamino, —SO$_3$H, —SO$_2$NH$_2$, aminocarbonylamino, oxycarbonylamino, HR'NCHR"C(O)NH—, azido, cyano, halo, hydroxyamino, and hydrazino where R' is hydrogen and R" is a side-chain of an amino acid or where R' and R" together with the nitrogen and carbon bound to each group respectively form a pyrrolidinyl group;

A and B are independently selected from the group consisting of C=Q", NH, and methylene optionally substituted with 1 to 2 halo groups, provided that A and B are not both NH;

D is NH, or -D-A-B— together form a —N=CH—NH—, —(C=Q")-CH$_2$—(C=Q-)-, —(C=Q")-NH—(C=Q")-, —(CX')=(CX')—(C=Q")-, or —CH=CH—NH— group where X' is halo;

each Q" is independently selected from the group consisting of O, S, and NH;

T$^1$ and T$^2$ are independently selected from the group consisting of hydrogen, hydroxyl, C$_1$-C$_4$-alkoxy, C$_1$-C$_4$-thioalkoxy, amino, substituted amino, and halo; and W, W$^1$, Y and X are as defined for formula I.

In another of its composition aspects, the present invention is directed to compounds of Formula Ic:

Ic

[chemical structure]

wherein

----- between Z$^1$ and Z$^2$, between Z$^2$ and Z$^3$, between Z$^4$ and R$^1$, and between N and Z$^4$ indicates a bond that may be a single or a double bond and ---- indicates a single bond or no bond, provided that:

only one of the bonds between Z$^1$ and Z$^2$ and between Z$^2$ and Z$^3$ is a double bond;

Z$^1$ is selected from the group consisting of CH, CH$_2$, C—NH$_2$, C—NHCH$_3$;

Z$^2$ is selected from the group consisting of CH, CH$_2$;

Z$^3$ is selected from the group consisting of CH, CH$_2$, C(O);

provided that if Z$^1$ is CH, C—NH$_2$ or C—NHCH$_3$, then Z$^2$ is CH and Z$^3$ is not CH;

Y is selected from the group consisting of a bond, —CH$_2$— or —O—; and

X is selected from the group consisting of O—W$^2$ and halo;

each of W, W$^1$ and W$^2$ is independently selected from the group consisting of hydrogen, C$_{1-4}$alkyl, and a pharmaceutically acceptable prodrug group;

or pharmaceutically acceptable tautomers, salts or partial salts thereof;

provided that at least one of W$^1$ and W$^2$ is a pharmaceutically acceptable prodrug group; and further provided that said compound, tautomer, salt, or partial salt is not represented by formula II or III or a tautomer, salt, or partial salt thereof

II

[chemical structure]

III

[chemical structure]

wherein:

Q' is absent or is selected from the group consisting of O, S, and NH, provided that when Q' is absent, V and NH are both attached to a CH$_2$ group;

V is selected from the group consisting of N and C-G;

Z is selected from the group consisting of N and C-G';

V and Z are not identical;

G and G' are independently selected from the group consisting of hydrogen, amino, aminocarbonyl, methylamino, dimethylamino, acylamino, alkoxyamino, —SO$_3$H, —SO$_2$NH$_2$, aminocarbonylamino, oxycarbonylamino, HR'NCHR"C(O)NH—, azido, cyano, halo, hydroxyamino, and hydrazino where R' is hydrogen and R" is a side-chain of an amino acid or where R' and R" together with the nitrogen and carbon bound to each group respectively form a pyrrolidinyl group;

A and B are independently selected from the group consisting of C=Q", NH, and methylene optionally substituted with 1 to 2 halo groups, provided that A and B are not both NH;

D is NH, or -D-A-B— together form a —N=CH—NH—, —(C=Q")-CH$_2$—(C=Q")-, —(C=Q")-NH—(C=Q")-, —(CX')=(CX')—(C=Q")-, or —CH=CH—NH— group where X' is halo;

each Q" is independently selected from the group consisting of O, S, and NH;

T$^1$ and T$^2$ are independently selected from the group consisting of hydrogen, hydroxyl, C$_1$-C$_4$-alkoxy, C$_1$-C$_4$-thioalkoxy, amino, substituted amino, and halo; and W, W$^1$, Y and X are as defined for formula I.

In one embodiment the compound of the present invention has the structure of Formula I or Formula Ia, X is O—W$^2$ and each of W, W$^1$, and W$^2$ is independently hydrogen or a pharmaceutically acceptable prodrug group selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR³NHR"³, where R¹³ is hydrogen and R³ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a sidechain of an amino acid; or R³ and R¹³ together with the carbon and nitrogen atoms bound thereto respectively form a heterocyclic ring. Preferably, W is hydrogen, phospho, diphospho, or triphospho.

In another embodiment the compound of the present invention has the structure of a Formula above, X is O—W² and one of W, W¹, and W² is hydrogen. In another embodiment, W and W¹ are H, or W and W² are H, or W² and W¹ are H. In yet another embodiment each of W, W¹, and W² is hydrogen.

In another embodiment the compound of the present invention has the structure of a Formula above, X is O—W² and W is represented by the formula:

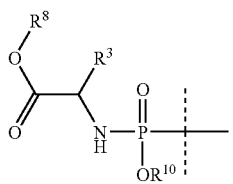

wherein R³ is a sidechain of an amino acid; R⁸ is hydrogen or alkyl; and R¹⁰ is selected from the group consisting of alkyl, substituted alkyl, aryl, substituted aryl, cycloalkyl, substituted cycloalkyl, heteroaryl, substituted heteroaryl, heterocyclic and substituted heterocyclic. Preferably one of W¹ and W² is hydrogen. More preferably W¹ and W² are hydrogen.

In another embodiment the compound of the present invention has the structure of a Formula above, X is O—W² and W¹ is represented by the formula:

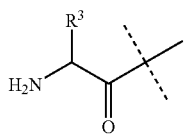

where R³ is a sidechain of an amino acid. Preferably one of W and W² is hydrogen. More preferably W and W² are hydrogen.

In one embodiment the compound of the present invention has the structure of a Formula above, X is halo, preferably fluoro, and each of W and W¹ is independently hydrogen or a pharmaceutically acceptable prodrug group selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR³NHR"³, where R¹³ is hydrogen and R³ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a sidechain of an amino acid; or R³ and R¹³ together with the carbon and nitrogen atoms bound thereto respectively form a heterocyclic ring. W is preferably hydrogen, phospho, diphospho, or triphospho.

In another embodiment the compound of the present invention has the structure of Formula I or Formula Ia, X is halo, preferably fluoro, and W is represented by the formula:

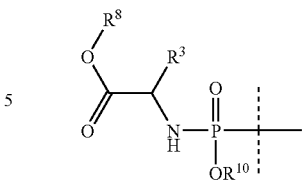

wherein R³ is a sidechain of an amino acid; R⁸ is hydrogen or alkyl; and R¹⁰ is selected from the group consisting of alkyl, substituted alkyl, aryl, substituted aryl, cycloalkyl, substituted cycloalkyl, heteroaryl, substituted heteroaryl, heterocyclic and substituted heterocyclic. Preferably W¹ is hydrogen.

In another embodiment the compound of the present invention has the structure of Formula I or Formula Ia, X is halo, preferably fluoro, and W¹ is represented by the formula:

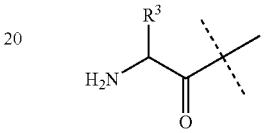

where R³ is a sidechain of an amino acid. Preferably, W is hydrogen.

In one embodiment the compound of the present invention has the structure of Formula I or Formula Ia, X is O—W², W² is $C_{1-4}$alkyl, preferably methyl, and each of W and W¹ is independently hydrogen or a pharmaceutically acceptable prodrug group selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR³NHR¹³, where R¹³ is hydrogen and R³ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a sidechain of an amino acid; or R³ and R¹³ together with the carbon and nitrogen atoms bound thereto respectively form a heterocyclic ring. Preferably W is hydrogen, phospho, diphospho, or triphospho. More preferably, one of W and W¹ is hydrogen. Even more preferably W and W¹ are hydrogen.

In one embodiment the compound of the present invention has the structure of Formula I or Formula Ia, X is O—W², W¹ is $C_{1-4}$alkyl, preferably methyl, and each W and W² is independently hydrogen or a pharmaceutically acceptable prodrug group selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR³NHR¹³, where R¹³ is hydrogen and R³ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a sidechain of an amino acid; or R³ and R¹³ together with the carbon and nitrogen atoms bound thereto respectively form a heterocyclic ring. Preferably W is hydrogen, phospho, diphospho, or triphospho. More preferably, one of W and W² is hydrogen. Even more preferably W and W² are hydrogen.

In one embodiment the compound of the present invention has the structure of Formula I or Formula Ia, X is O—W², W is $C_{1-4}$alkyl, preferably methyl, and each of W¹ and W² is independently hydrogen or a pharmaceutically acceptable prodrug group selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR³NHR¹³, where R¹³ is hydrogen and R³ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a sidechain of an amino acid; or R³ and R¹³ together with the carbon and nitrogen atoms bound thereto respectively form a heterocyclic ring. More preferably, one of $W^1$ and $w^2$ is hydrogen. Even more preferably $W^1$ and $W^2$ are hydrogen.

In another embodiment the compound of the present invention has the structure of Formula I or Formula Ia, X is O—$W^2$ and W is represented by the formula:

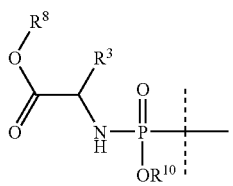

wherein R³ is a sidechain of an amino acid; R⁸ is hydrogen or alkyl; and R¹⁰ is selected from the group consisting of alkyl, substituted alkyl, aryl, substituted aryl, cycloalkyl, substituted cycloalkyl, heteroaryl, substituted heteroaryl, heterocyclic and substituted heterocyclic. In another embodiment $W^1$ is hydrogen and $W^2$ is $C_{1-4}$alkyl, preferably methyl. In yet another embodiment $W^2$ is hydrogen and $W^1$ is $C_{1-4}$alkyl, preferably methyl.

In another embodiment the compound of the present invention has the structure of Formula I or Formula Ia, X is O—$W^2$ and $W^1$ is represented by the formula:

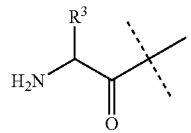

where R³ is a sidechain of an amino acid. In another embodiment W is hydrogen and $W^2$ is methyl. In still another embodiment $W^2$ is hydrogen and W is methyl.

Some examples of compounds included in the present invention are named in the list below and in Table I.

2-(2'-methyl-β-D-ribofuranosyl)-2,6,8,9-tetrahydro-2,3,5,6-tetraaza-benzo[cd]azulen-7-one;

2-(2'-methyl-β-D-ribofuranosyl)-6,7-dihydro-2H-2,3,5,6-tetraaza-benzo[cd]azulene;

2-(2'-methyl-β-D-ribofuranosyl)-6,9-dihydro-2H-2,3,5,6-tetraaza-benzo[cd]azulene;

2-(2'-methyl-β-D-ribofuranosyl)-6,7,8,9-tetrahydro-2H-2,3,5,6-tetraaza-benzo[cd]azulene;

2-(2'-methyl-β-D-ribofuranosyl)-2,6-dihydro-2,3,5,6-tetraaza-benzo[cd]azulen-7-one;

9-Amino-2-(2'-methyl-β-D-ribofuranosyl)-2,6-dihydro-2,3,5,6-tetraaza-benzo[cd]azulen-7-one; and 2-(2'-methyl-β-D-ribofuranosyl)-9-methylamino-2,6-dihydro-2,3,5,6-tetraaza-benzo[cd]azulen-7-one;

or pharmaceutically acceptable prodrugs, salts, or partial salts thereof.

In Table I below, $Q^1$, $Q^2$, $Q^3$, $Q^4$, and $Q^5$ have the definitions as provided above:

TABLE I

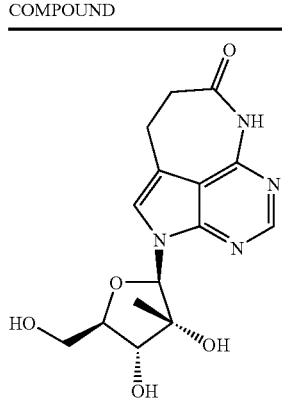

| COMPOUND | R | R¹ | Z¹ | Z² | Z³ |
|---|---|---|---|---|---|
| | H | —H (p = 0) | CH₂ | CH₂ | C(O) |

TABLE I-continued

| COMPOUND | R | R¹ | Z¹ | Z² | Z³ |
|---|---|---|---|---|---|
| (structure) | H | —H (p = 0) | CH | CH | CH$_2$ |
| (structure) | H | —H (p = 0) | CH$_2$ | CH | CH |
| (structure) | H | —H (p = 0) | CH$_2$ | CH$_2$ | CH$_2$ |

TABLE I-continued

| COMPOUND | R | R¹ | Z¹ | Z² | Z³ |
|---|---|---|---|---|---|
| (structure) | H | —H (p = 0) | CH | CH | C(O) |
| (structure) | H | —H (p = 0) | C—NH$_2$ | CH | C(O) |
| (structure) | H | —H (p = 0) | C—NHCH$_3$ | CH | C(O) |

TABLE I-continued
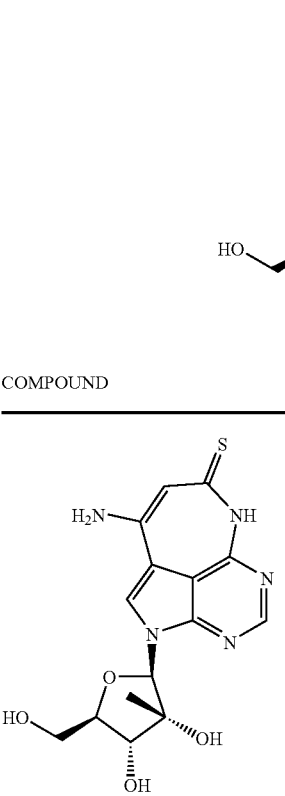
| COMPOUND | R | R¹ | Z¹ | Z² | Z³ |
|---|---|---|---|---|---|
| 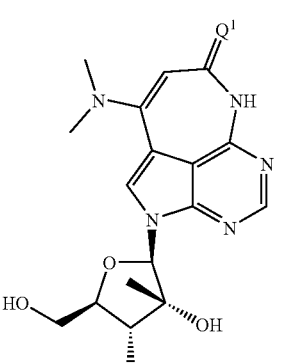 | H | —H (p = 0) | C—$NH_2$ | CH | C(S) |
| 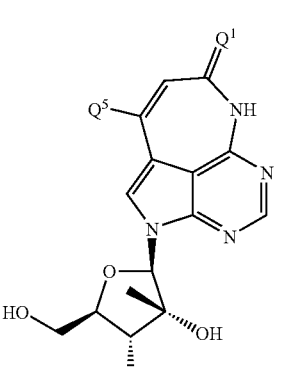 | H | —H (p = 0) | C—$N(CH_3)_2$ | CH | C($Q^1$) |
|  | H | —H (p = 0) | C—$Q^5$ | CH | C($Q^1$) |

TABLE I-continued
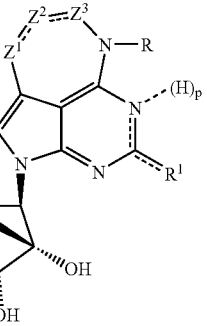
| COMPOUND | R | R¹ | Z¹ | Z² | Z³ |
|---|---|---|---|---|---|
| (structure) | H | —H (p = 0) | C(Q¹) | CH$_2$ | C(Q¹) |
| (structure) | H | —H (p = 0) | C—T (where T is —OCH$_3$ or SCH$_3$) | CH | C(Q¹) |
| (structure) | H | —H (p = 0) | C—CN | CH | C(Q¹) |

TABLE I-continued
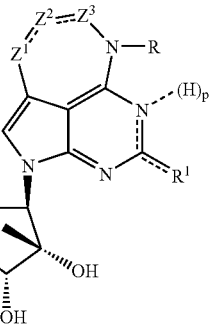
| COMPOUND | R | R$^1$ | Z$^1$ | Z$^2$ | Z$^3$ |
|---|---|---|---|---|---|
| 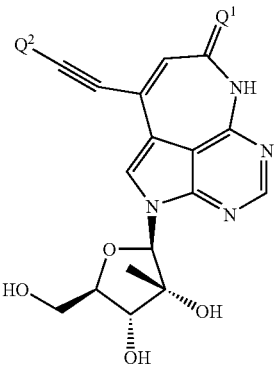 | H | —H (p = 0) | CC≡C—Q$^2$ | CH | C(Q$^1$) |
| 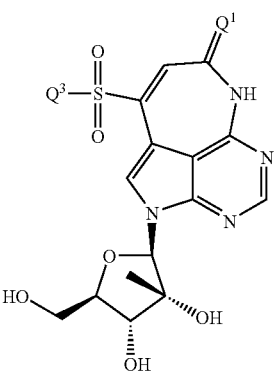 | H | —H (p = 0) | C—N$_3$ | CH | C(Q$^1$) |
|  | H | —H (p = 0) | C—SO$_2$—Q$^3$ | CH | C(Q$^1$) |

TABLE I-continued
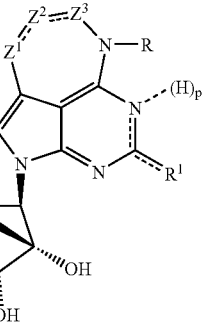
| COMPOUND | R | R$^1$ | Z$^1$ | Z$^2$ | Z$^3$ |
|---|---|---|---|---|---|
| (structure) | H | —H (p = 0) | NH | C(Q$^1$) | C(Q$^1$) |
| (structure) | H | —H (p = 0) | NH | CH$_2$ | C(Q$^1$) |
| (structure) | H | —H (p = 0) | N | CH | C(Q$^1$) |

TABLE I-continued
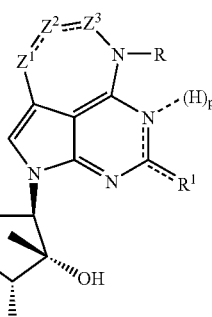
| COMPOUND | R | R¹ | Z¹ | Z² | Z³ |
|---|---|---|---|---|---|
| 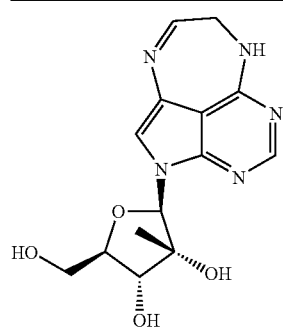 | H | —H (p = 0) | N | CH | $CH_2$ |
| 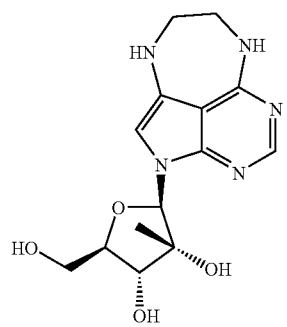 | H | —H (p = 0) | NH | $CH_2$ | $CH_2$ |
| 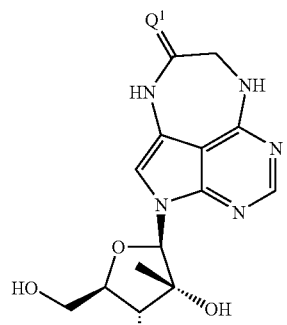 | H | —H (p = 0) | NH | $C(Q^1)$ | $CH_2$ |

TABLE I-continued
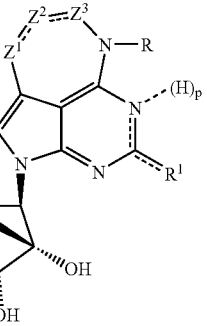
| COMPOUND | R | R¹ | Z¹ | Z² | Z³ |
|---|---|---|---|---|---|
| 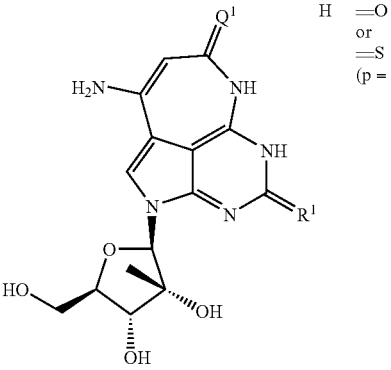 | H | =O or =S (p = 1) | C—NH$_2$ | CH | C(Q¹) |
| 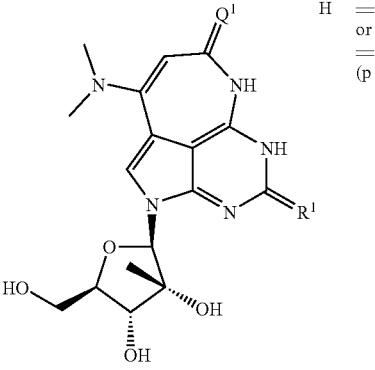 | H | =O or =S (p = 1) | C—(CH$_3$)$_2$ | CH | C(Q¹) |
|  | H | =O or =S (p = 1) | C—Q⁵ | CH | C(Q¹) |

TABLE I-continued

| COMPOUND | R | R¹ | Z¹ | Z² | Z³ |
|---|---|---|---|---|---|
| (structure with Q¹=O, Q¹=O on seven-membered ring fused to pyrrolopyrimidine ribonucleoside) | H | =O or =S (p = 1) | C(Q¹) | CH₂ | C(Q¹) |
| (structure with Q¹, T² substituent) | H | =O or =S (p = 1) | T² = C—OCH₃ or C—O—C₂₋₄alkyl | CH | C(Q¹) |
| (structure with Q¹, NC substituent) | H | =O or =S (p = 1) | C—CN | CH | C(Q¹) |

TABLE I-continued
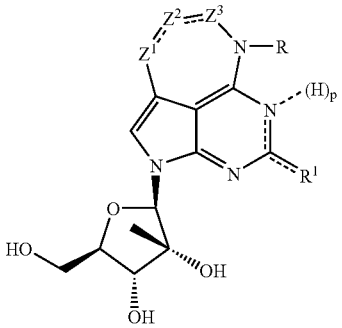
| COMPOUND | R | R¹ | Z¹ | Z² | Z³ |
|---|---|---|---|---|---|
| 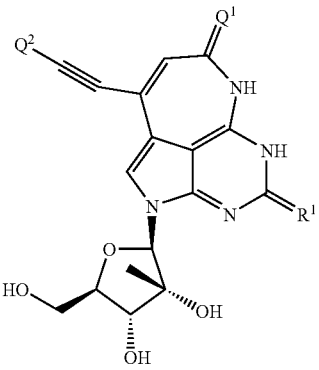 | H | =O or =S (p = 1) | CC≡C—Q² | CH | C(Q¹) |
| 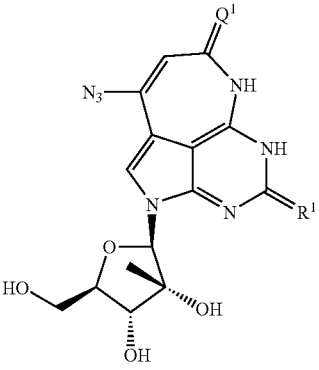 | H | =O or =S (p = 1) | C—N₃ | CH | C(Q¹) |
| 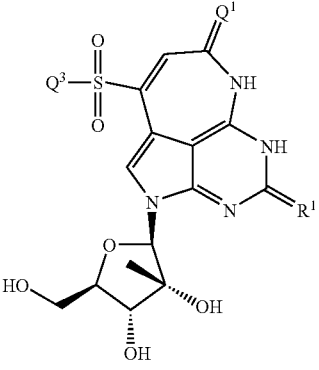 | H | =O or =S (p = 1) | —C—SO₂—Q³ | CH | C(Q¹) |

TABLE I-continued
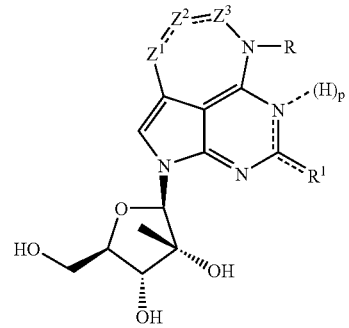
| COMPOUND | R | R¹ | Z¹ | Z² | Z³ |
|---|---|---|---|---|---|
| 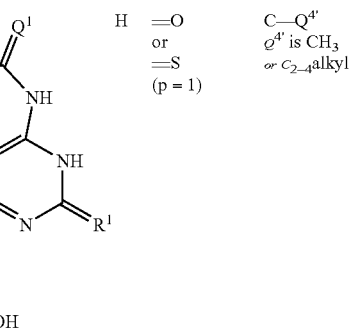 | H | =O or =S (p = 1) | C—Q⁴' $Q^{4'}$ is CH₃ or $C_{2-4}$alkyl | CH | C(Q¹) |
| 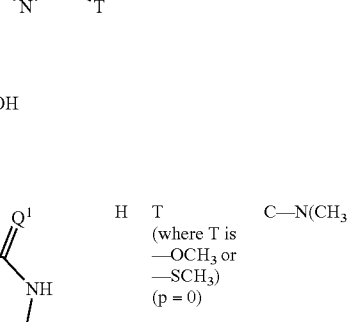 | H | T (where T is —OCH₃ or —SCH₃) (p = 0) | C—NH₂ | CH | C(Q¹) |
| 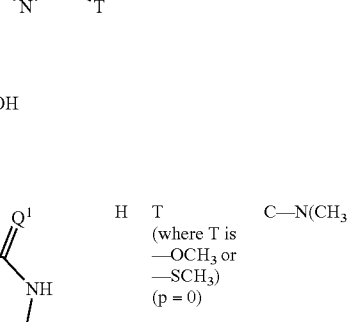 | H | T (where T is —OCH₃ or —SCH₃) (p = 0) | C—N(CH₃)₂ | CH | C(Q¹) |

TABLE I-continued
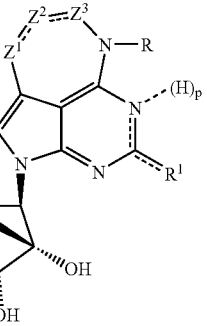
| COMPOUND | R | R¹ | Z¹ | Z² | Z³ |
|---|---|---|---|---|---|
| (structure) | H | T (where T is —OCH₃ or —SCH₃) (p = 0) | C—Q⁵ | CH | C(Q¹) |
| (structure) | H | T (where T is —OCH₃ or —SCH₃) (p = 0) | C(Q¹) | CH₂ | C(Q¹) |
| (structure) | H | T (where T is —OCH₃ or —SCH₃) (p = 0) | T² = C— OCH₃ or C— O—C₂₋₄alkyl | CH | C(Q¹) |

TABLE I-continued
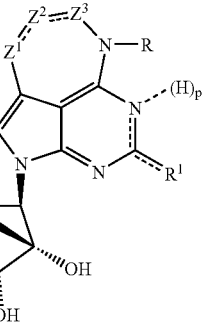
| COMPOUND | R | R¹ | Z¹ | Z² | Z³ |
|---|---|---|---|---|---|
| (structure) | H | T (where T is —OCH$_3$ or —SCH$_3$) (p = 0) | C—CN | CH | C(Q¹) |
| (structure) | H | T (where T is —OCH$_3$ or —SCH$_3$) (p = 0) | CC≡C—Q² | CH | C(Q¹) |
| (structure) | H | T (where T is —OCH$_3$ or —SCH$_3$) (p = 0) | C—N$_3$ | CH | C(Q¹) |

TABLE I-continued
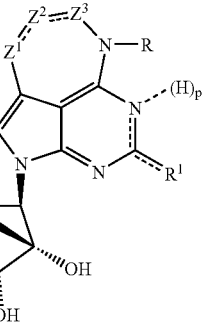
| COMPOUND | R | R¹ | Z¹ | Z² | Z³ |
|---|---|---|---|---|---|
| 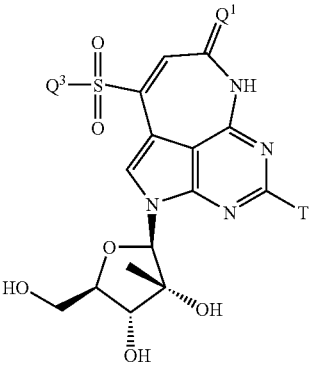 | H | T (where T is —OCH$_3$ or —SCH$_3$) (p = 0) | C—SO$_2$Q$^3$ | CH | C(Q¹) |
| 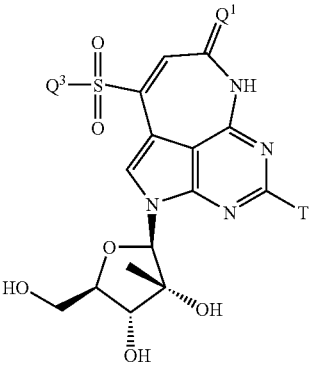 | H | T (where T is —OCH$_3$ or —SCH$_3$) (p = 0) | C—Q$^{4'}$ Q$^{4'}$ is CH$_3$ or C$_{2-4}$alkyl | CH | C(Q¹) |
| 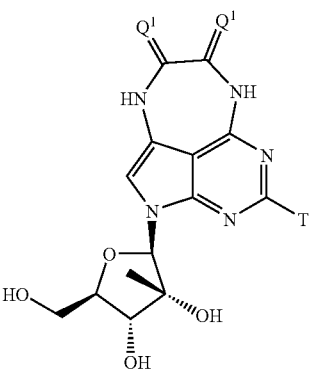 | H | T (where T is —OCH$_3$ or SCH$_3$) (p = 0) | NH | C(Q¹) | C(Q¹) |

TABLE I-continued
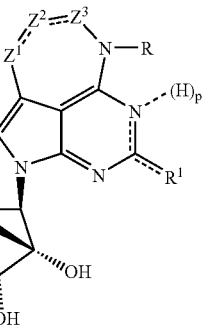
| COMPOUND | R | R¹ | Z¹ | Z² | Z³ |
|---|---|---|---|---|---|
| (structure) | H | T (where T is —OCH$_3$ or —SCH$_3$) (p = 0) | NH | CH$_2$ | C(Q¹) |
| (structure) | H | T (where T is —OCH$_3$ or —SCH$_3$) (p = 0) | N | CH | C(Q¹) |
| (structure) | H | T (where T is —OCH$_3$ or —SCH$_3$) (p = 0) | N | CH | CH$_2$ |

TABLE I-continued
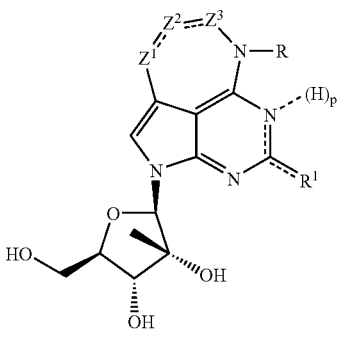
| COMPOUND | R | R¹ | Z¹ | Z² | Z³ |
| --- | --- | --- | --- | --- | --- |
| 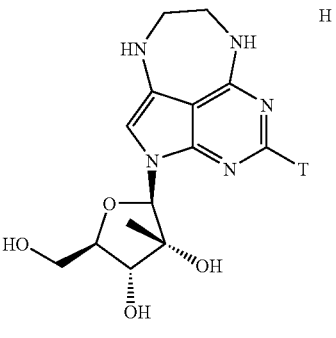 | H | T (where T is —OCH₃ or —SCH₃) (p = 0) | NH | CH₂ | CH₂ |
| 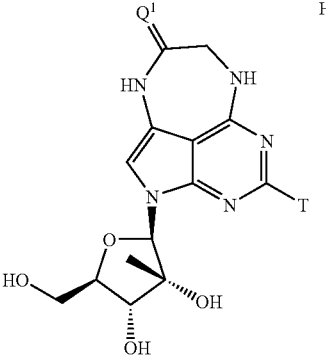 | Q¹ | T (where T is —OCH₃ or —SCH₃) (p = 0) | NH | C(Q¹) | CH₂ |
|  | H | =O or =S (p = 1) | NH | C(Q¹) | C(Q¹) |

TABLE I-continued
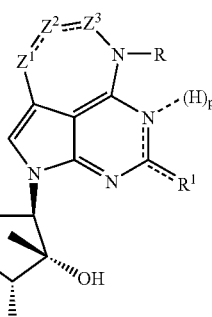
| COMPOUND | R | R¹ | Z¹ | Z² | Z³ |
|---|---|---|---|---|---|
| 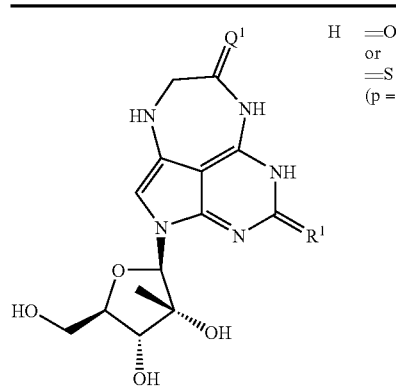 | H | =O or =S (p = 1) | NH | $CH_2$ | $C(Q^1)$ |
| 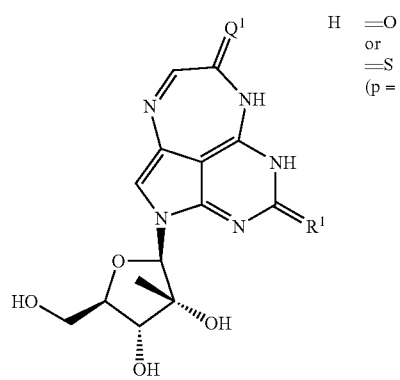 | H | =O or =S (p = 1) | N | CH | $C(Q^1)$ |
| 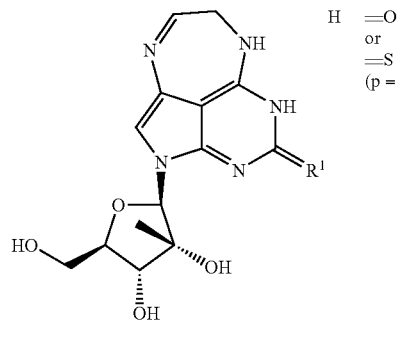 | H | =O or =S (p = 1) | N | CH | $CH_2$ |

TABLE I-continued

| COMPOUND | R | $R^1$ | $Z^1$ | $Z^2$ | $Z^3$ |
|---|---|---|---|---|---|
| [structure] | H | =O or =S (p = 1) | NH | $CH_2$ | $CH_2$ |
| [structure] | $Q^1$ | =O or =S (p = 1) | NH | $C(Q^1)$ | $CH_2$ |

Compounds of this invention are active as antiviral agents or are useful as intermediates in the preparation of other antiviral agents of this invention.

This invention is also directed to pharmaceutical compositions comprising a pharmaceutically acceptable diluent and a therapeutically effective amount of a compound described herein or mixtures of one or more of such compounds.

This invention is still further directed to methods for treating a viral infection mediated at least in part by a virus in the Flaviviridae family of viruses, such as HCV, in mammals which methods comprise administering to a mammal, that has been diagnosed with said viral infection or is at risk of developing said viral infection, a pharmaceutical composition comprising a pharmaceutically acceptable diluent and a therapeutically effective amount of a compound of this invention or mixtures of one or more of such compounds.

In yet another embodiment of the invention, methods of treating or preventing viral infections in mammals are provided wherein the compounds of this invention are administered in combination with the administration of a therapeutically effective amount of one or more agents active against HCV. Active agents against HCV include Ribavirin, levovirin, viramidine, thymosin alpha-1, an inhibitor of NS3 serine protease, and inhibitor of inosine monophosphate dehydrogenase, interferon-alpha or pegylated interferon-alpha, either alone or in combination with Ribavirin, viramidine or levovirin. Preferably the additional agent active against HCV is interferon-alpha or pegylated interferon-alpha alone or in combination with Ribavirin, viramidine or levovirin.

DETAILED DESCRIPTION OF THE INVENTION

The invention is directed to compounds, compositions and methods for treating Flaviviridae viruses, such as hepatitis C virus infections. However, prior to describing this invention in detail, the following terms will first be defined:

Definitions

As used herein, the term "alkyl" refers to hydrocarbyl groups having from 1 to 6 carbon atoms and more preferably 1 to 2 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, oxyacyl, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—.

"Formyl" refers to the —C(O)H group.

"Acylamino" refers to the group —C(O)NR$^4$R$^4$ where each R$^4$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R$^4$ is joined to form together with the nitrogen atom a heterocyclic or substituted heterocyclic ring.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—.

"Oxyacyl" refers to the groups alkyl-OC(O)—, substituted alkyl-OC(O)—, alkenyl-OC(O)—, substituted alkenyl-OC(O)—, alkynyl-OC(O)—, substituted alkynyl-OC(O)—, aryl-OC(O)—, substituted aryl-OC(O)—, cycloalkyl-OC(O)—, substituted cycloalkyl-OC(O)—, heteroaryl-OC(O)—, substituted heteroaryl-OC(O)—, heterocyclic-OC(O)—, and substituted heterocyclic-OC(O)—.

"Alkenyl" refers to an unsaturated hydrocarbon preferably having from 2 to 6 carbon atoms and more preferably 2 to 4 carbon atoms and having at least 1 and preferably from 1-2 sites of vinyl (>C=C<) unsaturation. Such groups are exemplified by vinyl (ethen-1-yl), allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom. Preferred substituted alkenyl groups are selected from, but not limit to, 2,2-difluoroethen-1-yl, 2-methoxyethen-1-yl, and the like.

It is understood that the term "substituted alkenyl" includes both E (cis) and Z (trans) isomers as appropriate. The isomers can be pure isomeric compounds or mixtures of E and Z components.

"Alkynyl" refers to an unsaturated hydrocarbon having at least 1 site of acetylenic (—C≡C—) unsaturation and having from 2 to 6 carbon atoms and more preferably 2 to 4 carbon atoms. Preferred alkynyl groups are selected from but not limit to ethyn-1-yl, propyn-1-yl, propyn-2-yl, 1-methylprop-2-yn-1-yl, butyn-1-yl, butyn-2-yl, butyn-3-yl, and the like.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic with the proviso that any hydroxyl substitution is not attached to an acetylenic carbon atom. Preferred substituted alkynyl groups are selected from but not limit to 2-fluoroethyn-1-yl, 3,3,3-trifluoropropyn-1-yl, 3-aminopropyn-1-yl, 3-hydroxypropyn-1-yl, and the like.

"Amino" refers to the group —NH$_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocyclic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino.

"Aminoacyl" refers to the groups —NR$^5$C(O)alkyl, —NR$^5$C(O)substituted alkyl, —NR$^5$C(O)cycloalkyl, —NR$^5$C(O)substituted cycloalkyl, —NR$^5$C(O)alkenyl, —NR$^5$C(O)substituted alkenyl, —NR$^5$C(O)alkynyl, —NR$^5$C(O)substituted alkynyl, —NR$^5$C(O)aryl, —NR$^5$C(O)substituted aryl, —NR$^5$C(O)heteroaryl, —NR$^5$C(O)substituted heteroaryl, —NR$^5$C(O)heterocyclic, and —NR$^5$C(O)substituted heterocyclic where R$^5$ is hydrogen or alkyl.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl", including "substituted phenyl" refers to aryl groups or phenyl groups which are substituted with from 1 to 3 substituents, and preferably 1 to 2 substituents, selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl ester, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or salts thereof.

"Carboxyl ester" refers to the groups —C(O)O-alkyl, —C(O)O-substituted alkyl, —C(O)O-aryl, and —C(O)O-substituted aryl wherein alkyl, substituted alkyl, aryl and substituted aryl are as defined herein.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Substituted cycloalkyl" refers to a cycloalkyl having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Heteroaryl" refers to an aromatic group of from 1 to 10 carbon atoms and 1 to 4 heteroatoms selected from the group consisting of oxygen, nitrogen, sulfur in the ring. The sulfur and nitrogen heteroatoms atoms may also be present in their oxidized forms, such as N(O), S(O) and S(O)$_2$. Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Preferred heteroaryls include pyridyl, pyrrolyl, thienyl, indolyl, thiophenyl, and furyl.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" or "heterocycloalkyl" refers to a saturated or unsaturated group (but not heteroaryl) having a single ring or multiple condensed rings, from 1 to 10 carbon atoms and from 1 to 4 hetero atoms selected from the group consisting of nitrogen, oxygen, sulfur, S(O), and S(O)$_2$ within the ring wherein, in fused ring systems, one or more the rings can be cycloalkyl, aryl or heteroaryl provided that the point of attachment is through the heterocyclic ring.

"Substituted heterocyclic" or "substituted heterocycloalkyl" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Phosphate" refers to the groups —OP(O)(OH)$_2$ (monophosphate or phospho), —OP(O)(OH)OP(O)(OH)$_2$ (diphosphate or diphospho) and —OP(O)(OH)OP(O)(OH)OP(O)(OH)$_2$ (triphosphate or triphospho) or salts thereof including partial salts thereof. It is understood, of course, that the initial oxygen of the mono-, di- and triphosphate (phospho, diphospho and triphospho) includes the oxygen atom at, for example, the 5-position of the ribose sugar.

"Phosphate esters" refers to the mono-, di- and tri-phosphate groups described above wherein one or more of the hydroxyl groups is replaced by an alkoxy group.

"Phosphonate" refers to the groups —OP(O)(R$^6$)(OH) or —OP(O)(R$^6$)(OR$^{6'}$) or salts thereof including partial salts thereof, wherein R$^6$ is independently selected from hydrogen, alkyl, and substituted alkyl, and R$^{6'}$ is independently selected from hydrogen, alkyl, substituted alkyl, carboxylic acid, and carboxyl ester. It is understood, of course, that the initial oxygen of the phosphonate includes the oxygen atom at, for example, the 5-position of the ribose sugar.

"Phosphorodiamidate" refers to the group:

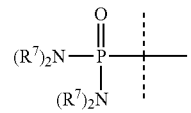

where each R$^7$ may be the same or different and each is hydrogen, alkyl, substituted alkyl, cycloalkyl, or substituted cycloalkyl. A particularly preferred phosphorodiamidate is the following group:

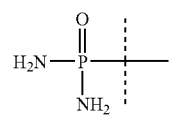

"Phosphoramidate monoester" refers to the group below, where R$^3$ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a sidechain of an amino acid; and R$^8$ is hydrogen or alkyl. In a preferred embodiment R$^3$ is derived from an L-amino acid.

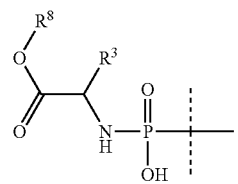

"Phosphoramidate diester" refers to the group below, where R$^{10}$ is selected from the group consisting of alkyl, substituted alkyl, aryl, substituted aryl, cycloalkyl, substituted cycloalkyl, heteroaryl, substituted heteroaryl, heterocyclic and substituted heterocyclic, and R$^3$ and R$^8$ are as defined above. In a preferred embodiment R$^3$ is derived from an L-amino acid.

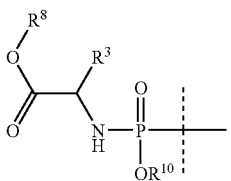

"Cyclic phosphoramidate" refers to the group below, where n is 1 to 3, more preferably n is 1 to 2.

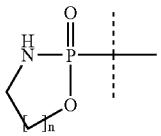

"Cyclic phosphorodiamidate" refers to the group below, where n is 1 to 3, more preferably n is 1 to 2.

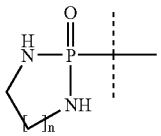

"Phosphonamidate" refers to the group below, where $R^{11}$ is hydrogen, alkyl, substituted alkyl, cycloalkyl, or substituted cycloalkyl.

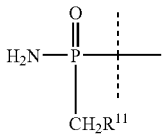

"Thiol" refers to the group —SH.

"Thioalkyl" or "alkylthioether" or "thioalkoxy" refers to the group —S-alkyl.

"Substituted thioalkyl" or "substituted alkylthioether" or "substituted thioalkoxy" refers to the group —S-substituted alkyl.

"Thiocycloalkyl" refers to the groups —S-cycloalkyl and "substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group -S-substituted heterocyclic.

The term "amino acid sidechain" refers to the $R^3$ substituent of α-amino acids of the formula $R^{13}NHCH(R^3)COOH$ where $R^3$ is selected from the group consisting of hydrogen, alkyl, substituted alkyl and aryl and $R^{13}$ is hydrogen or together with $R^3$ and the nitrogen and carbon atoms bound thereto respectively form a heterocyclic ring. Preferably, the α-amino acid sidechain is the sidechain one of the twenty naturally occurring L amino acids.

The term "pharmaceutically acceptable prodrugs" refers to art recognized modifications to one or more functional groups which functional groups are metabolized in vivo to provide a compound of this invention or an active metabolite thereof. "Prodrug group" refers to a type of protecting group that, when used to mask a functional group within an active drug, converts the drug into a prodrug. Prodrug groups are typically attached to the functional group of the drug via bonds that are cleavable under specified conditions of use. Such functional groups are well known in the art including acyl groups for hydroxyl and/or amino substitution, esters of mono-, di- and tri-phosphates wherein one or more of the pendent hydroxyl groups have been converted to an alkoxy, a substituted alkoxy, an aryloxy or a substituted aryloxy group, and the like.

The term "pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkyl-ammonium, and the like; and when the molecule contains a basic functionality, salts of organic or inorganic acids, such as hydrochloride, hydrobromide, tartrate, mesylate, acetate, maleate, oxalate and the like.

The term "pharmaceutically acceptable partial salts" refers to compounds having a substituent capable of having more than one group form a salt but less than the maximum amount of such groups actually form a salt. For example, a diphospho group can form a plurality of salts and, if only partially ionized, the resulting group is sometimes referred to herein as a partial salt.

The term "tautomers" as used herein refers to rapidly interconverting constitutional isomers, usually distinguished by a different bonding location for a labile hydrogen atom and a differently located double bond.

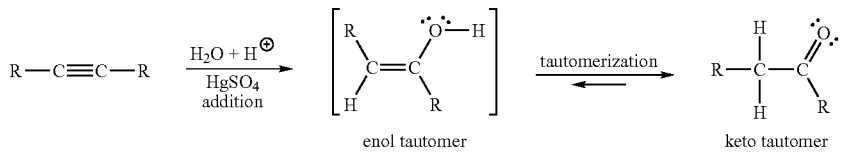

The equilibrium between tautomers is rapid under normal conditions and often strongly favors one of the isomers ( acetone, for example, is 99.999% keto tautomer ). Even in such one-sided equilibria, evidence for the presence of the minor tautomer comes from the chemical behavior of the compound. Tautomeric equilibria are catalyzed by traces of acids or bases that are generally present in most chemical samples. Some examples of tautomers of the present invention are shown below:

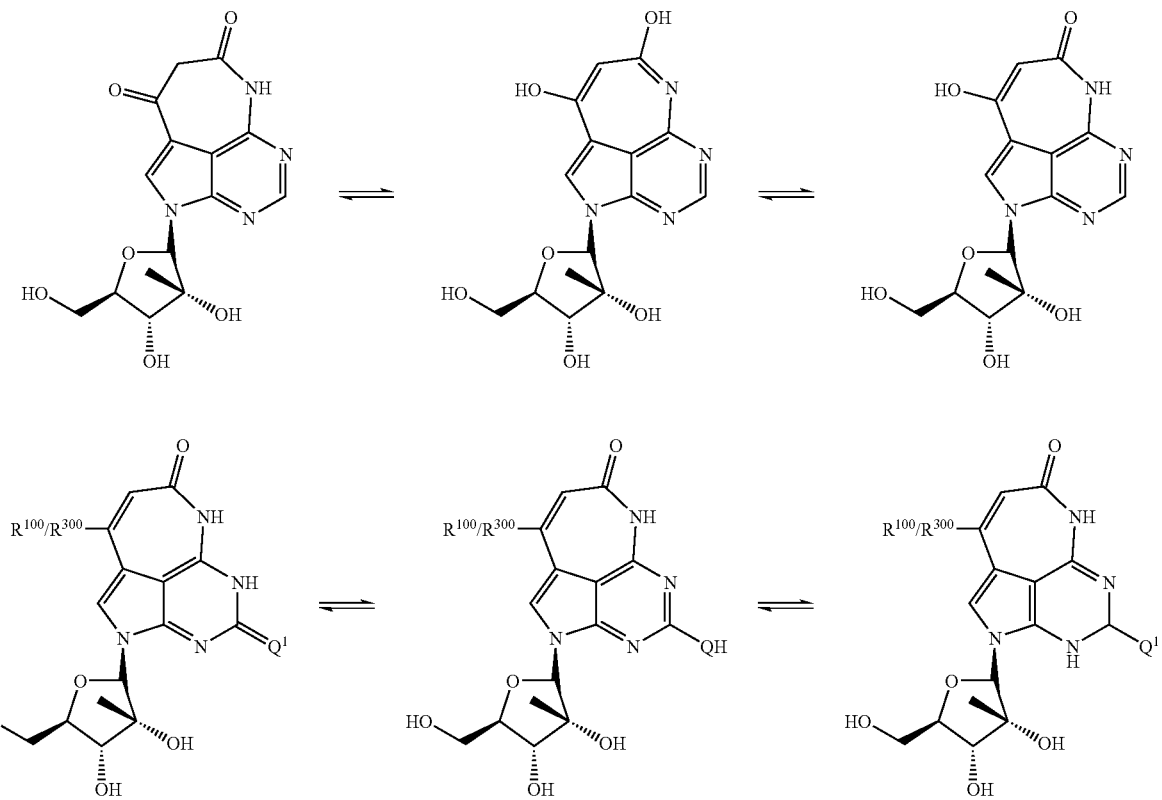

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to—substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Etika-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4$^{th}$ Edition), and Larock's Comprehensive Organic Transformations (VCH Publishers Inc., 1989).Specifically, the compounds of this invention may be prepared by various methods known in the art of organic chemistry in general and nucleoside and nucleotide analogue synthesis in particular. General reviews of the preparation of nucleoside and nucleotide analogues include 1) Michelson A. M. "*The Chemistry of Nucleosides and Nucleotides*," Academic Press, New York, 1963; 2) Goodman L. "*Basic Principles in Nucleic Acid Chemistry*," Academic Press, New York, 1974, vol. 1, Ch. 2; and 3) "*Synthetic Procedures in Nucleic Acid Chemistry*," Eds. Zorbach W. & Tipson R., Wiley, New York, 1973, vol. 1 & 2.

In one embodiment, the synthesis of certain compounds of this invention proceeds via the 7-(2'-methyl-β-D-ribofuranosyl)-4-amino-5-iodopyrrolo[2,3-d]pyrimidine, compound 1, the synthesis of which is described in Scheme 1 below and is also described in U.S. patent application Ser. No. 10/861,090, filed Jun. 4, 2004 which application is incorporated herein by reference in its entirety.

(about 1.05 to 1.10 equivalents) of N-iodsuccinimide with 4-chloro-1H-pyrrolo [2,3-d]pyrimidine, compound 1a. The reaction is preferably conducted under ambient conditions in the absence of light in a suitable solvent such as N,N-dimethylformamide. The reaction is continued until substantially complete which occurs in about 2 to 24 hours to produce 4-chloro-5-iodo-1H-pyrrolo[2,3-d]pyrimidine, compound 1b. Upon reaction completion, compound 1b is recovered by conventional methods including neutralization, evaporation, extraction, precipitation, chromatography, filtration, and the like, or, alternatively, is used in the next reaction without purification and/or isolation.

4-Chloro-5-iodo-1H-pyrrolo[2,3-d]pyrimidine, compound 1b, is then coupled to a protected 2-methyl substituted sugar the synthesis of which is described, for example, by Carroll, et al.,[17,18] using conditions well known in the art to provide for the 3,5-di-O-protected 7-deazapurine compound. For example, known 1-O-methyl-3,5-di-(O-2,4-dichlorobenzyl)-2-C-methyl-D-ribofuranoside, compound 1c, is dis-

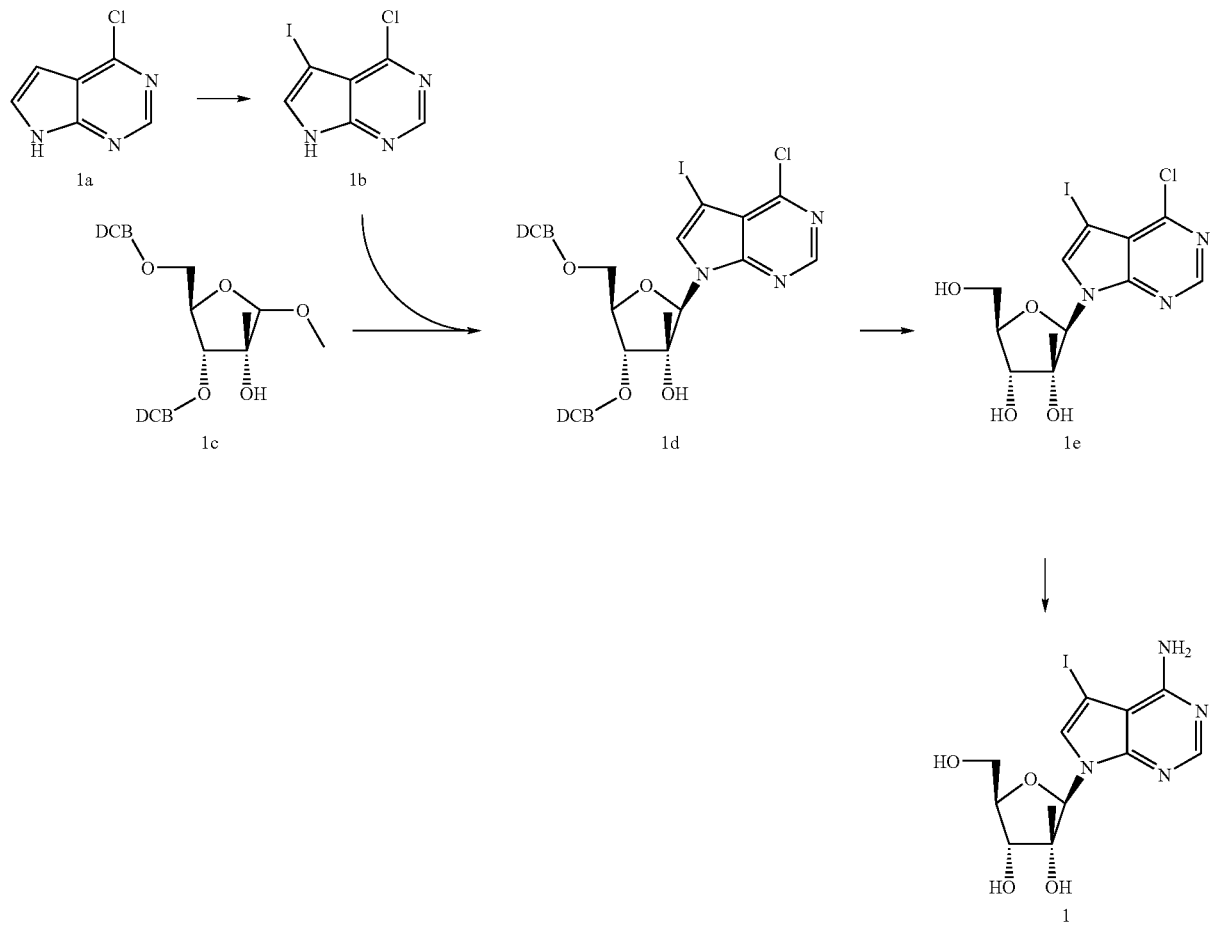

Scheme 1 where DCB is dichlorobenzyl.

Specifically, in Scheme 1, known 4-chloro-1H-pyrrolo[2,3-d]pyrimidine (Example 62, Step D, Carroll, et al.[18]), compound 1a, is converted to the corresponding 4-chloro-5-iodo-1H-pyrrolo[2,3-d]pyrimidine, compound 1b, by iodination with N-iodosuccinimide. Specifically, the reaction is typically conducted by combining a slight stoichiometric excess solved in a dry inert solvent, such as dichloromethane, chloroform, carbon tetrachloride and the like, and then the solution is cooled to about 0° C. Afterwards, an excess of HBr or other appropriate reagent, in acetic acid, is added drop wise. This reaction is typically run about 1 to about 4 hours at temperature at about 0 to about 25° C., or until substantially complete as determined by conventional techniques such as TLC. The resulting brominated sugar mixture (not shown) is isolated and purified using standard techniques such as chromatography, precipitation, crystallization, filtration, and the like. Alternatively this intermediate may be isolated and used in the next step without further purification. The resulting brominated sugar mixture is co-evaporated, preferably with dry toluene, dissolved in a suitable inert diluent such as dry acetonitrile and stirred with the sodium salt of 4-chloro-5-iodo-1H-pyrrolo[2,3-d]pyrimidine (not shown) at room temperature over night. The resulting compound 1d, 7-(2'-methyl-3',5'-di-(O-2,4-dichlorobenzyl)-β-D-ribofuranosyl)-4-chloro-5-iodopyrrolo[2,3-d]pyrimidine, is isolated and purified using standard techniques such as chromatography, precipitation, crystallization, filtration, and the like. Alternatively, this intermediate may be isolated and used in the next step without further purification.

The sodium salt of 4-chloro-5-iodo-1H-pyrrolo[2,3-d]pyrimidine is prepared in an inert atmosphere by suspending compound 1b in a dry inert solvent such as, acetonitrile and the like, with NaH dispersed in oil. The reaction is run for about 2 to about 24 hours at a temperature of about 0 to about 40° C.

The 2,4-dichlorobenzyl protecting groups at the 3,5-positions of compound 1d are removed under conventional conditions such as contact with an excess of boron trichloride in a suitable solvent such as dichloromethane, chloroform, and the like, to provide for 7-(2'-methyl-β-D-ribofuranosyl)-4-chloro-5-iodopyrrolo[2,3-d]pyrimidine, compound 1e. Specifically, the reaction is preferably conducted at a temperature of from about 0 to about −80° C. until the reaction is substantially complete which occurs in about 0.2 to 2 hours to produce compound 1e. Upon reaction completion, compound 1e is recovered by conventional methods including neutralization, evaporation, extraction, precipitation, chromatography, filtration, and the like, or, alternatively, is used in the next reaction without purification and/or isolation.

Conversion of compound 1e to 7-(2'-methyl-β-D-ribofuranosyl)-4-amino-5-iodopyrrolo[2,3-d]pyrimidine, compound 1 is achieved, for example, by contacting compound 1e with an excess of liquid ammonia. In one embodiment, the reaction is conducted at about 85° C. at elevated pressures until the reaction is substantially complete which typically occurs in about 12 to about 48 hours. Compound 1 is then isolated and purified using standard techniques such as chromatography, precipitation, crystallization, filtration, and the like.

Compound 1 can then be used as a key intermediate in the synthesis of compounds of this invention. In one embodiment illustrated in Scheme 2 where $Z^1$ and $Z^2$ are CH and $Z^3$ is C=O, the iodo group of compound 1 is converted to a 2-(ethyl carboxylate)acetylenyl group of compound 2. For illustrative purposes only, in Scheme 2, W, $W^1$ and X are hydroxyl, Y is oxygen, p is zero, the bond between N and $Z^4$ is a double bond and $R^3$ is hydrogen. Some of the reactions depicted in Scheme 2 are further illustrated in the examples below.

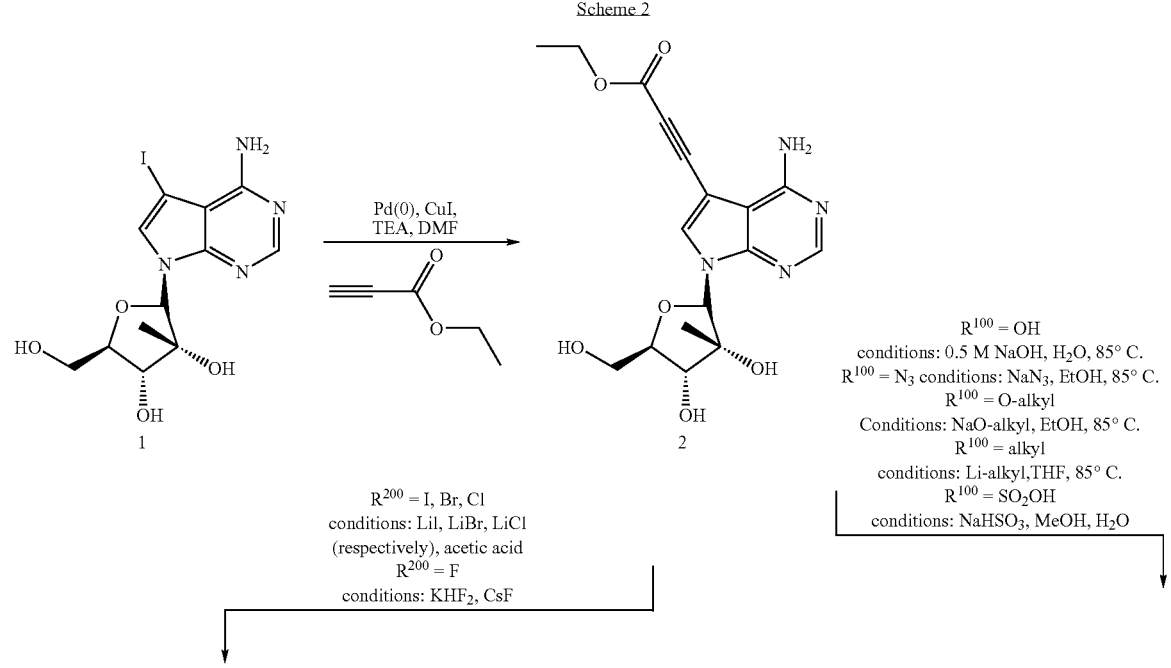

Scheme 2

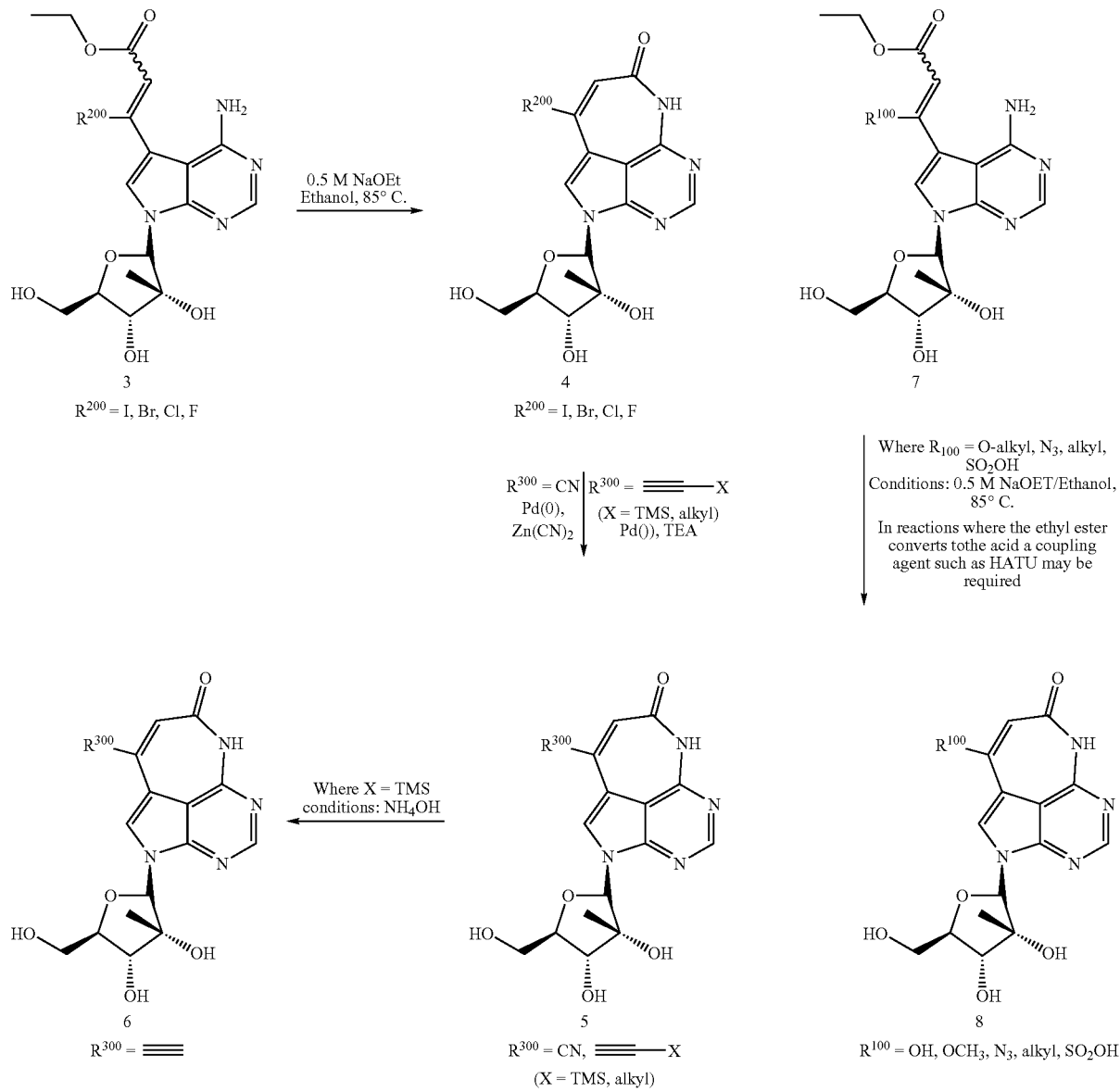

In Scheme 2, compound 1, described above, is converted first to the 7-(2'-C-methyl-β-D-ribofuranosyl)-4-amino-5-[(ethyl 2-carboxyl)ethyn-1-yl]-pyrrolo[2,3-d]pyrimidine, compound 2, using the procedures set forth therein. In one embodiment, compound 2 is converted to 7-(2'-C-methyl-β-D-ribofuranosyl)-4-amino-5-[(ethyl 2-carboxyl-1-halo)ethen-1-yl]-pyrrolo[2,3-d]pyrimidine, compound 3, using the procedures set forth therein. In turn, compound 3 is then cyclized under conventional basic conditions to provide for 9-halo-2-(2'-methyl-β-D-ribofuanosyl)-2,6-dihydro-2,3,5,6-tetraaza-benzo[cd]azulen-7-one, compound 4, a compound of formula I.

The halo group of compound 4 can be derivatized as illustrated in Scheme 2 to provide further compounds 5 and 6 which are compounds of formula I. Alternatively, dehalogenation under conventional conditions provides for $R^{100}$=hydrogen (not shown). This compound can also be prepared by conventional hydrogenatin of the 7-(2'-C-methyl-β-D-ribofuranosyl)-4-amino-5-[(ethyl 2-carboxyl)ethyn-1-yl]-pyrrolo[2,3-d]pyrimidine, compound 2, to provide for the 7-(2'-C-methyl-p-D-ribofuranosyl)-4-amino-5-[(ethyl 2-carboxyl)ethen-1-yl]-pyrrolo[2,3-d]pyrimidine followed by cyclization as described above.

In another embodiment, compound 2 is derivatized to 7-(2'-C-methyl-β-D-ribofuranosyl)-4-amino-5-[(ethyl 2-carboxyl-1-$R^{100}$-substituted)ethen-1-yl]-pyrrolo[2,3-d]pyrimidine, compound 7, using the procedures set forth therein. In turn, compound 7 is cyclized in the manner described therein to provide for compound 8. When $R^{100}$ is hydroxyl in compound 8, this compound has as one set of its tautomeric forms the following structures:

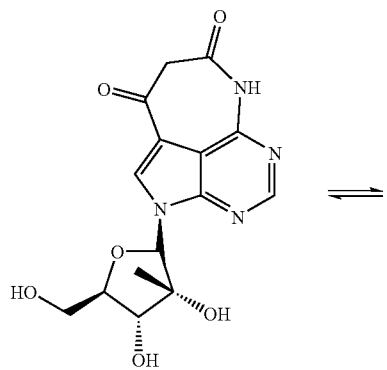 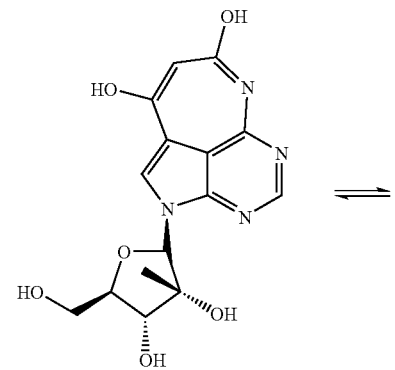 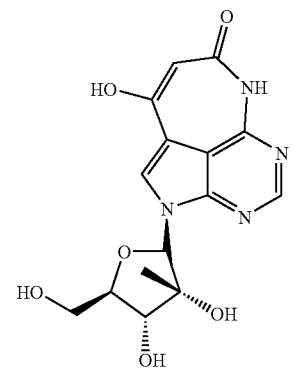

all of which are covered by this invention.

In addition to the compounds above, starting materials having $R^1$ other than hydrogen are known in the art and are disclosed, for example, by Carroll, et al.[17,18]

Further compounds of formula I can be prepared as shown in Scheme 3 below wherein, for illustrative purposes only, W, $W^1$ and X are hydroxyl, Y is oxygen, p is zero, the bond between N and $Z^4$ is a double bond and $R^1$ is initially methylthiol ($-SCH_3$). Compounds 9 and 10 are prepared in a manner described above in Schemes 1 and 2, where 4-chloro-2-methylthio-1H-pyrrolo[2,3-d]pyrimidine is used in place of compound 1a.

Scheme 3

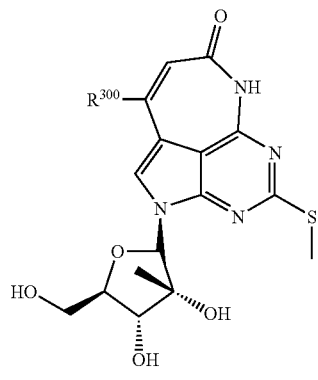 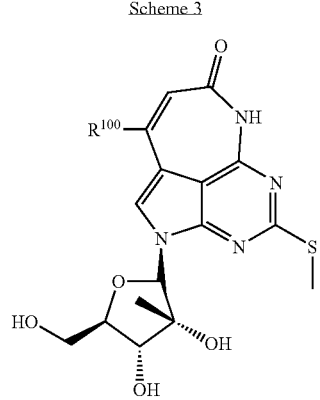 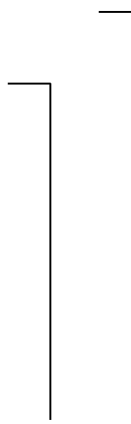

9
$R^{100}$ = CN, acetylene
≡—Alkyl

10
$R^{100}$ = OH, OCH$_3$, N$_3$
alkyl, SO$_2$OH

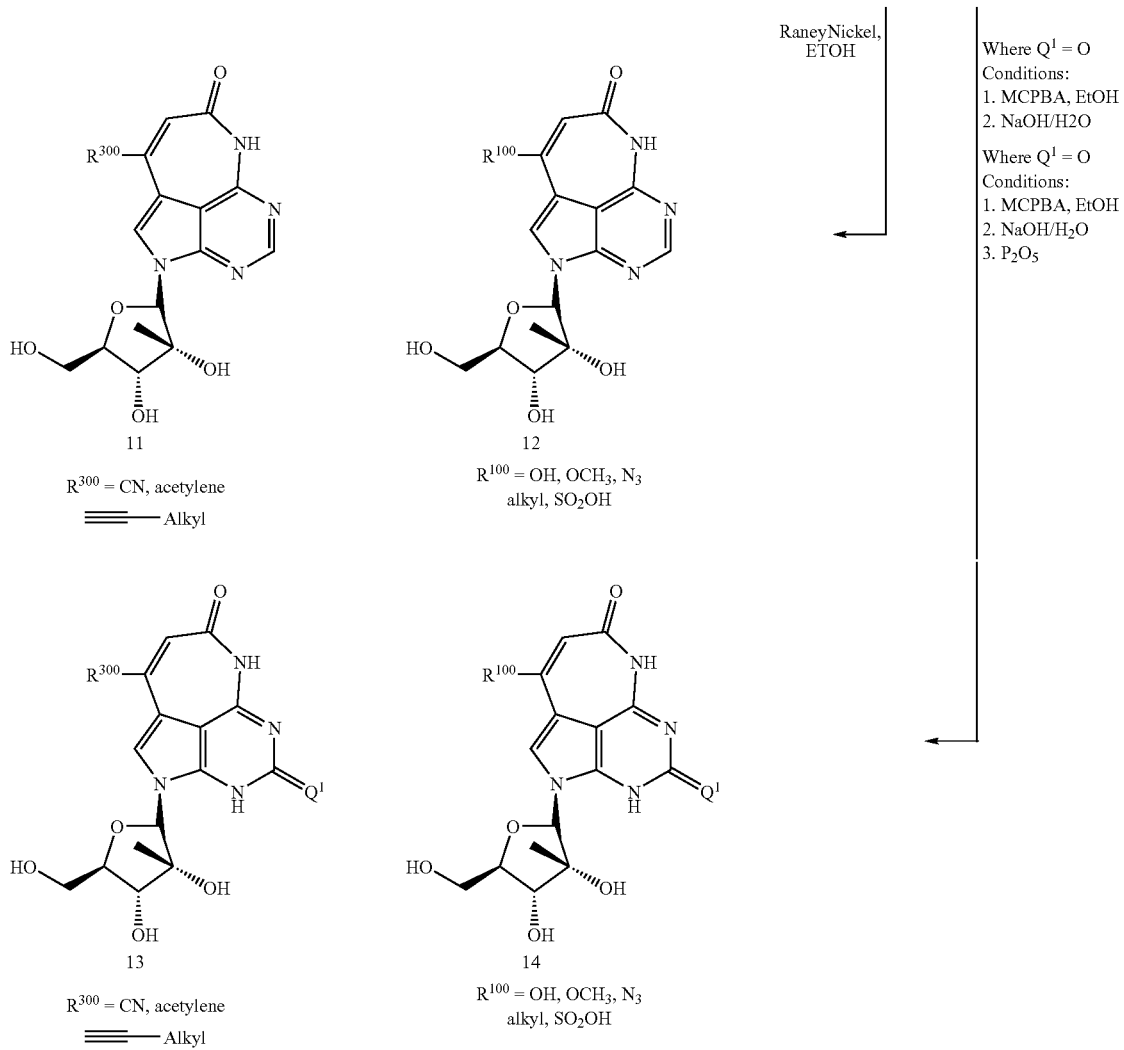

Specifically, in Scheme 3, conversion of the 2-methylthio derivatives, compounds 9 and 10, to the corresponding 2-hydrogen derivatives, compounds 11 and 12, proceeds as described therein. Alternatively, the 2-methylthio derivatives, compounds 9 and 10, can be converted to the corresponding compounds 13 and 14. Compounds 13 and 14 have as one set of its tautomeric forms the following structures:

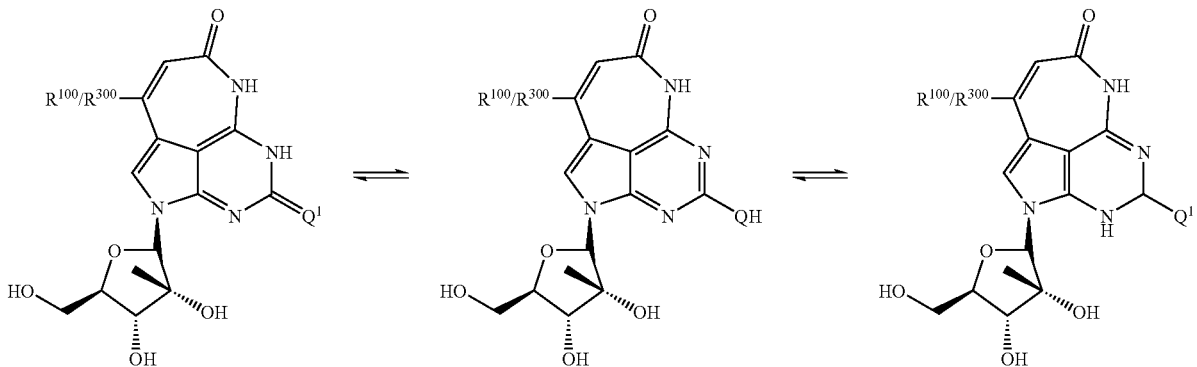

all of which are covered by this invention.
Scheme 4 below illustrates synthetic methods for forming a thiocarbonyl group on the lactam ring. As before, for illustrative purposes only, W, $W^1$ and X are hydroxyl, Y is oxygen, p is zero, the bond between N and $Z^4$ is a double bond and $R^1$ is methylthiol (—$SCH_3$).
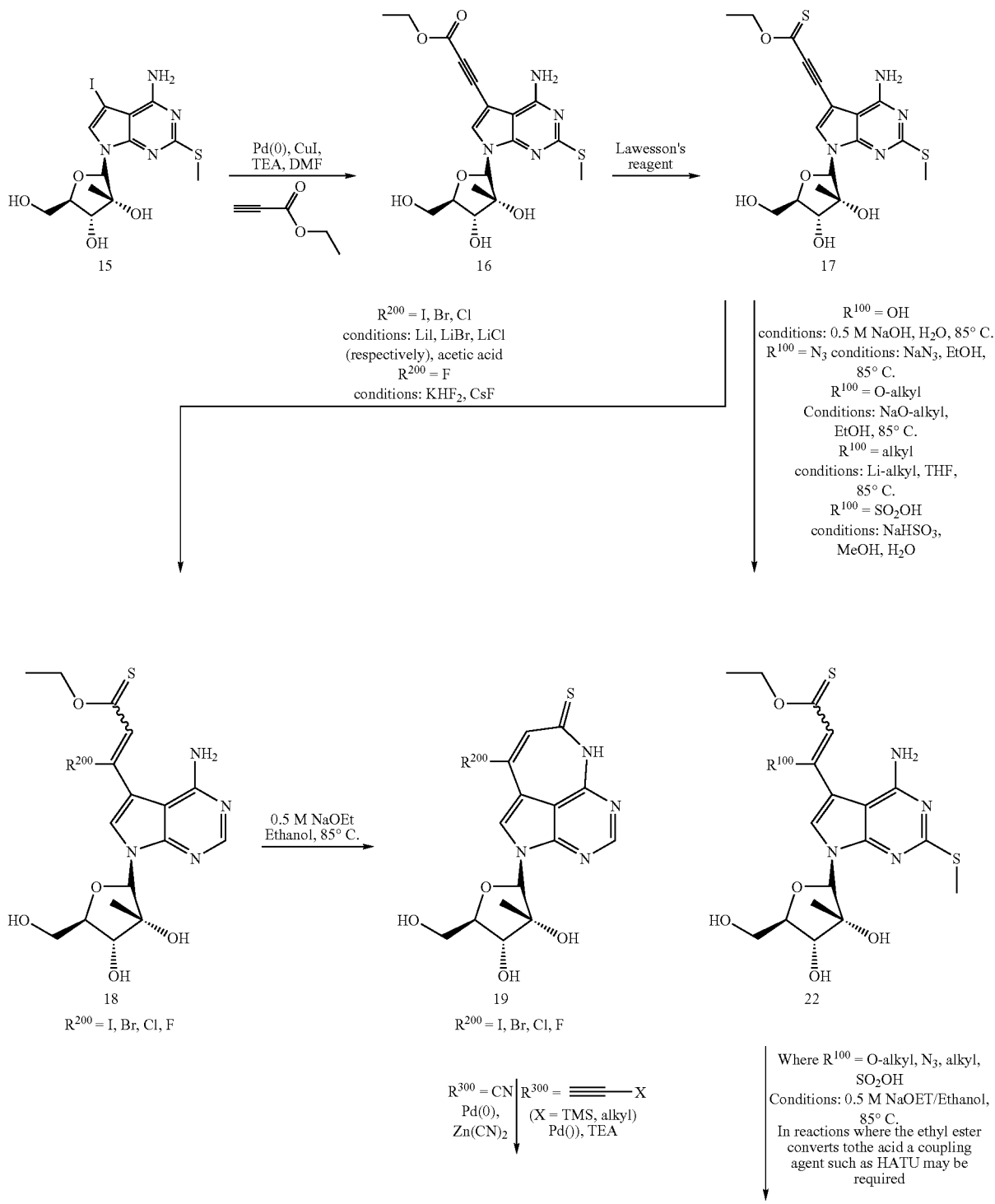

-continued

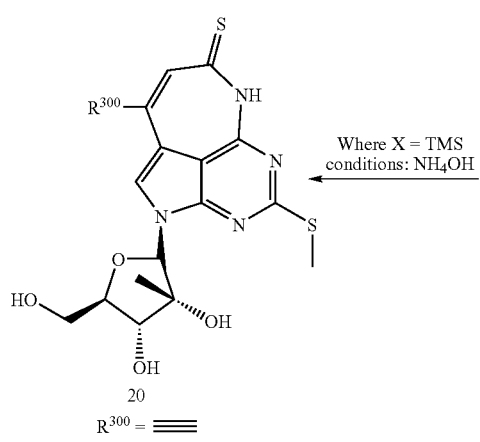
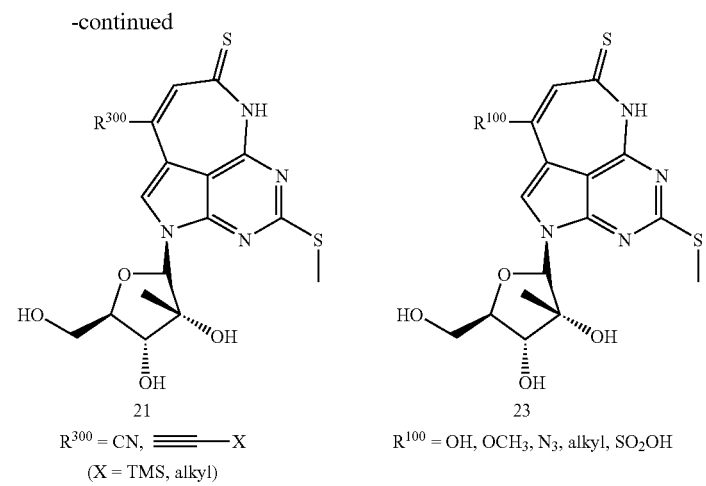

Specifically, in Scheme 4, compound 15 is prepared in a manner similar to that of Scheme 1 with the exception that the starting material is 4-chloro-2-methylthio-1H-pyrrolo[2,3-d]pyrimidine. Compound 15 is converted to compound 16 as described above and then the carbonyl group of the carboxyl ester is converted to the corresponding thiocarbonyl group using conventional methods, e.g., Lawesson's reagent as depicted above to provide for compound 17. This compound is converted to compounds 18, 19, 20, 21, 22 and 23 as described therein.

Scheme 5 below illustrates the synthesis diazepine compounds

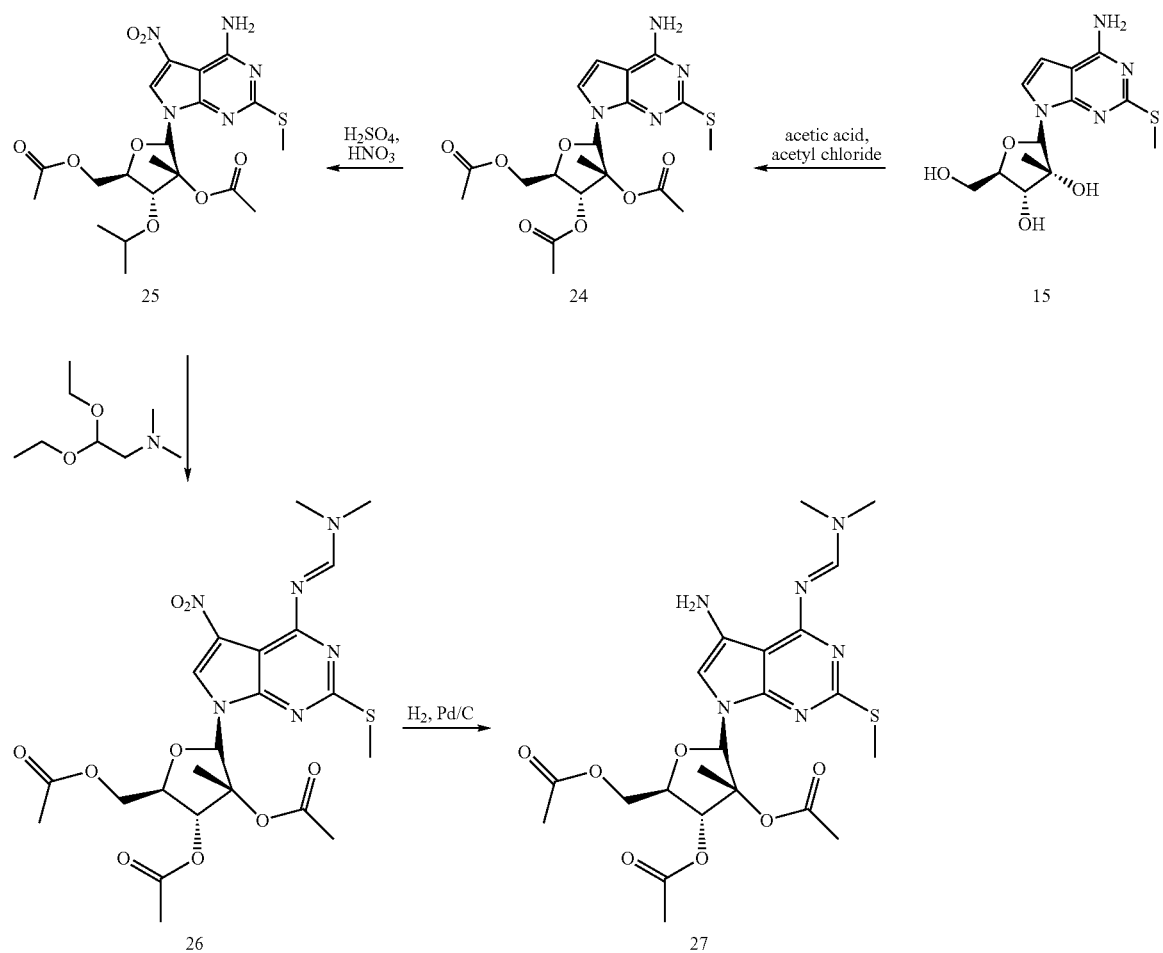

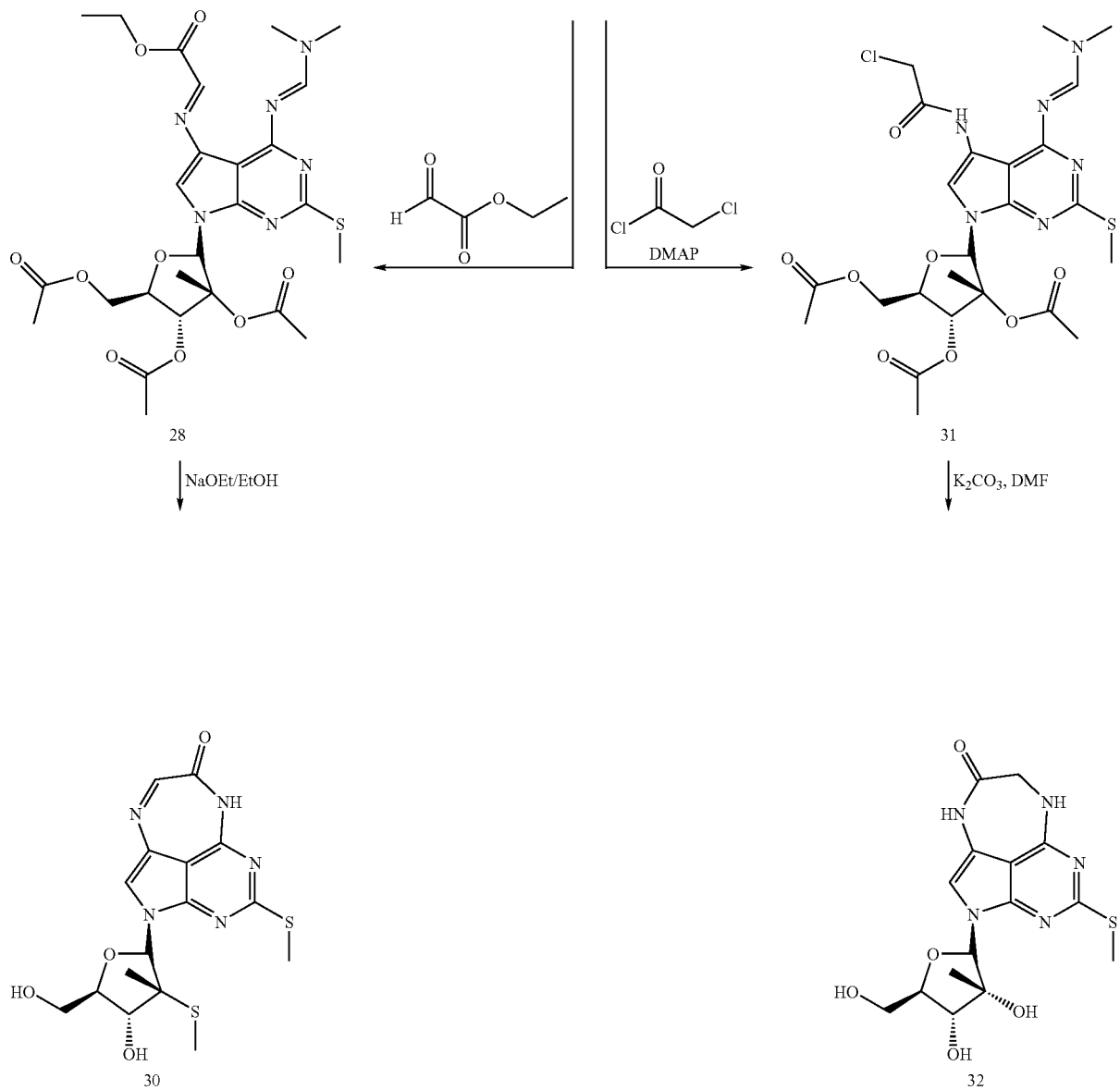

Specifically, in Scheme 5, Compound 15, described above, is converted to the corresponding 2,3,5-tri-O-protected sugar, compound 24, under conventional conditions. In turn, compound 24 is converted to the 5-nitro derivative, compound 25, by contact with a combination of nitric and sulfuric acid. Conversion of compound 25 to the imine of compound 26 proceeds by reaction with the masked aldehyde. Hydrogenation of the nitro group of compound 26 to the corresponding amine, compound 27, proceeds via conventional hydrogenation conditions.

In one embodiment, compound 27 is reacted with chloroacetyl chloride in the manner described above to provide for compound 31. Subsequent cyclization provides for compound 32.

In another embodiment, compound 27 is converted to compound 28 as shown in Scheme 5. Subsequent cyclization provides for compound 30.

Scheme 6 below illustrates further modifications of the compounds prepared in Scheme 4.

Scheme 6
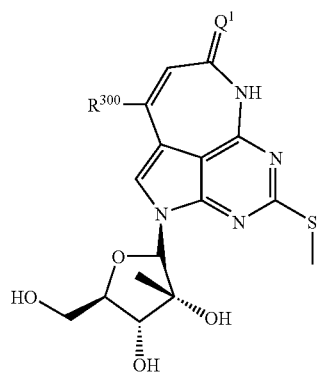
33
$R^{300}$ = CN, acetylene
≡— Alkyl
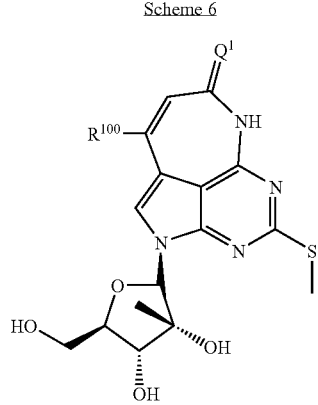
34
$R^{100}$ = OH, OCH₃, N₃
alkyl, SO₂OH
Only for lactam:
RaneyNickel,
ETOH
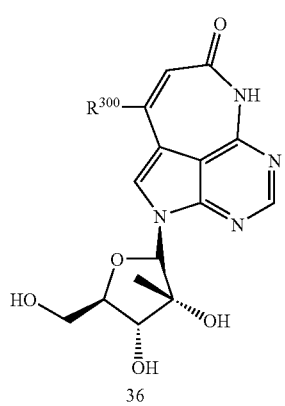
36
$R^{300}$ = CN, acetylene
≡—Alkyl
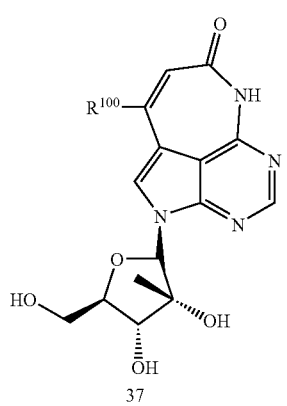
37
$R^{100}$ = OH, OCH₃, N₃
alkyl, SO₂OH
Where $R^4$ = O
Conditions:
1. MCPBA, EtOH
2. NaOH/H2O
Where $R^4$ = S
Conditions:
1. MCPBA, EtOH
2. NaOH/H2O
3. P2O5
1. MCPBA, EtOH
2. NaOMe/ MeOH
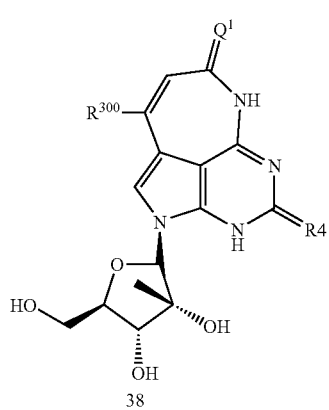
38
$R^{300}$ = CN, acetylene
≡—Alkyl
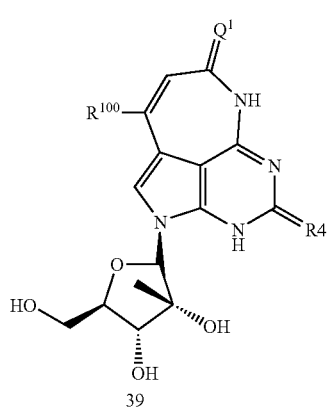
39
$R^{100}$ = OH, OCH₃, N₃
alkyl, SO₂OH -continued
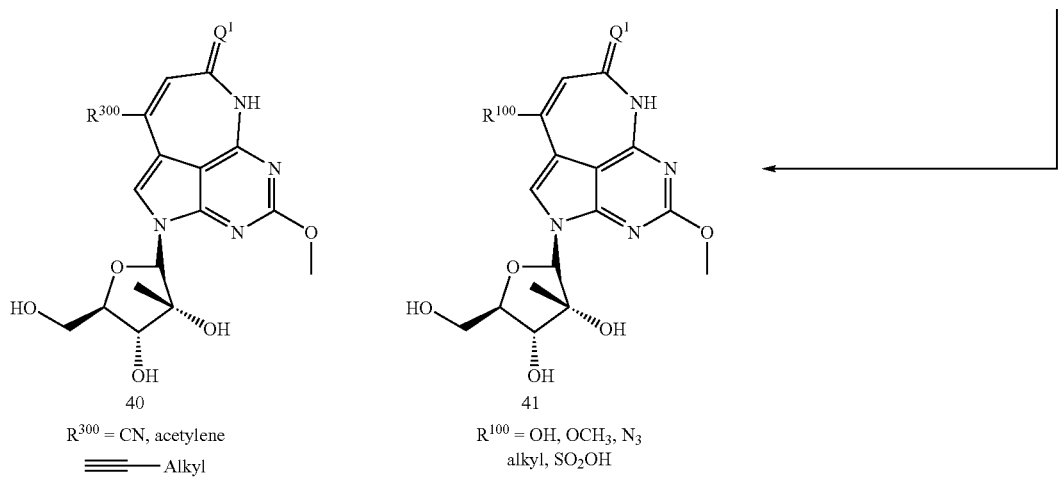
Scheme 6 follows the procedures of the synthetic methods described in Scheme 3 above to provide for compounds 36, 37, 38 and 39. Conversion of the thioether of compounds 33 and 34 to the corresponding ether of compounds 40 and 41 proceeds as described above.
Scheme 7 below illustrates the synthesis of 7 member ring compounds containing either one or two amide bonds.
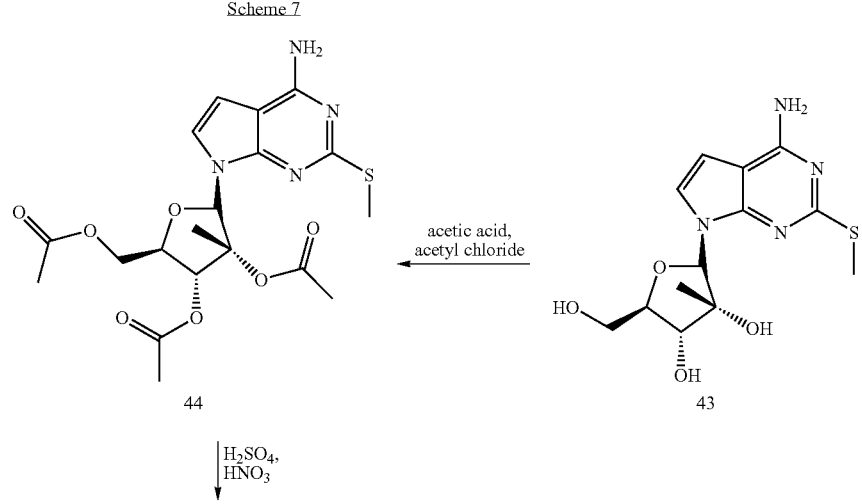

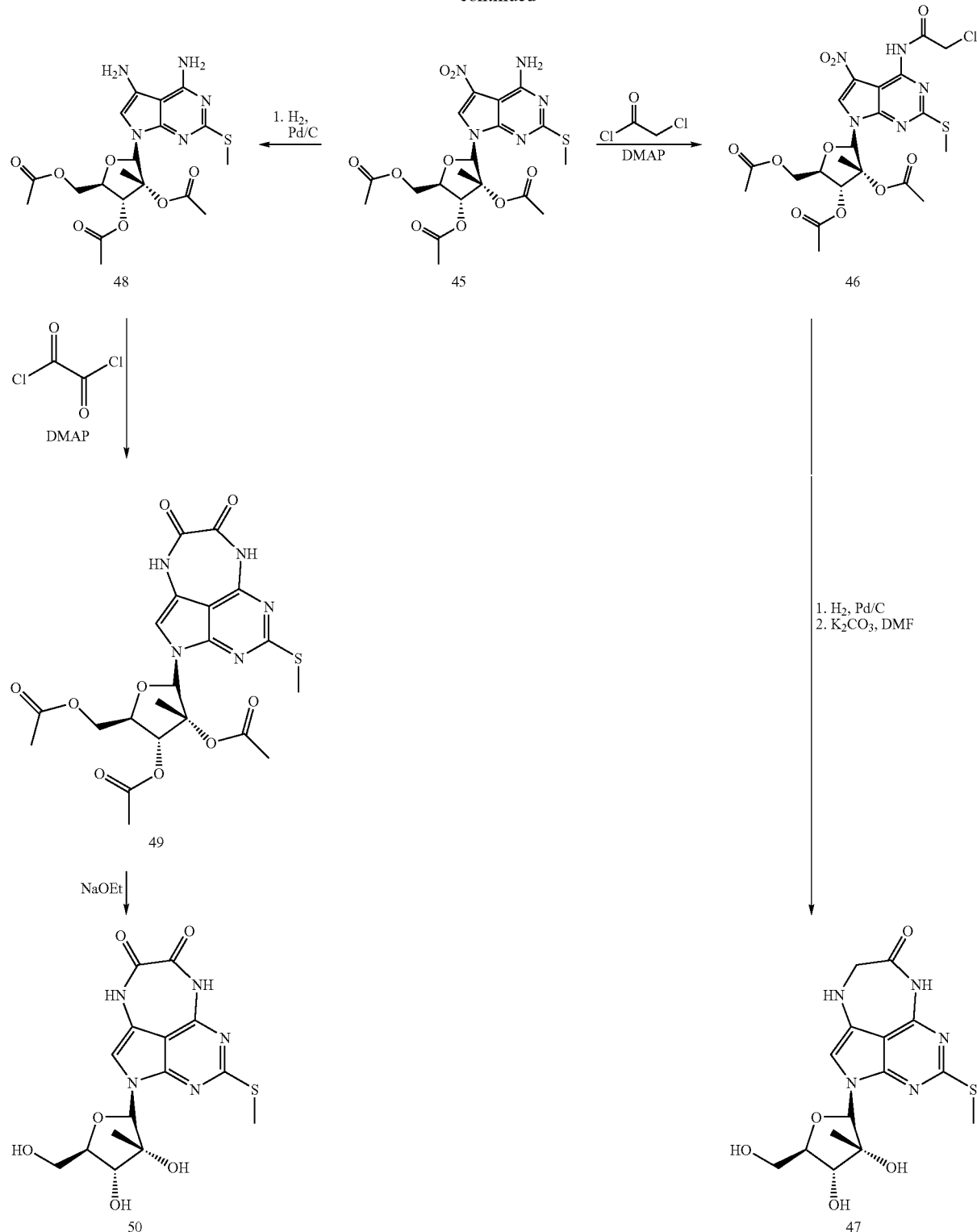

In Scheme 7, compound 43 is converted to the corresponding 2,3,5-tri-O-protected sugar, compound 44, under conventional conditions. In turn, compound 44 is converted to the 5-nitro derivative, compound 45, by contact with a combination of nitric and sulfuric acid. In one embodiment, compound 45 is contacted with chloroacetyl chloride in the presence of DMAP to form compound 46. Hydrogenation of the nitro group of compound 46 to the corresponding amine proceeds via conventional hydrogenation conditions. Cyclization of the intermediate 5-amino group (not shown)

by nucleophilic displacement of the chloro functionality of compound 46 in the presence of a base also removes the hydroxyl protecting groups to provide for compound 47.

In another embodiment, hydrogenation of the nitro group of compound 46 to the corresponding amine proceeds via conventional hydrogenation conditions to provide for diamine 48. Compound 48 is then reacted under conventional conditions with an excess of oxalyl chloride to provide for compound 49 which is followed by conventional removal of the protecting groups to provide for compound 50.

Scheme 8 illustrates modification of the 2-methylthio group of some of the compounds described above and follows the procedures of Schemes 3 and 6 above.

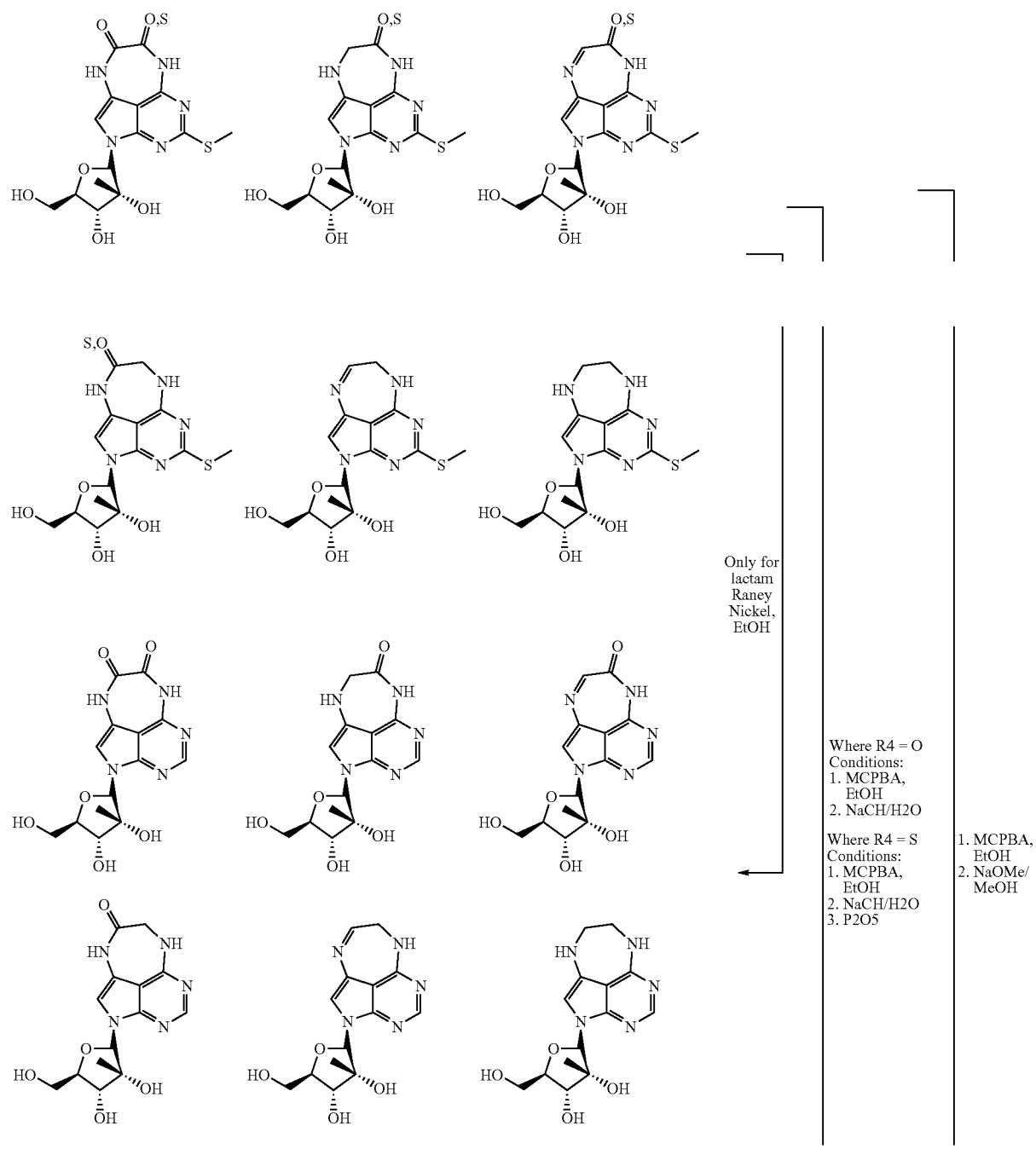

Scheme 8

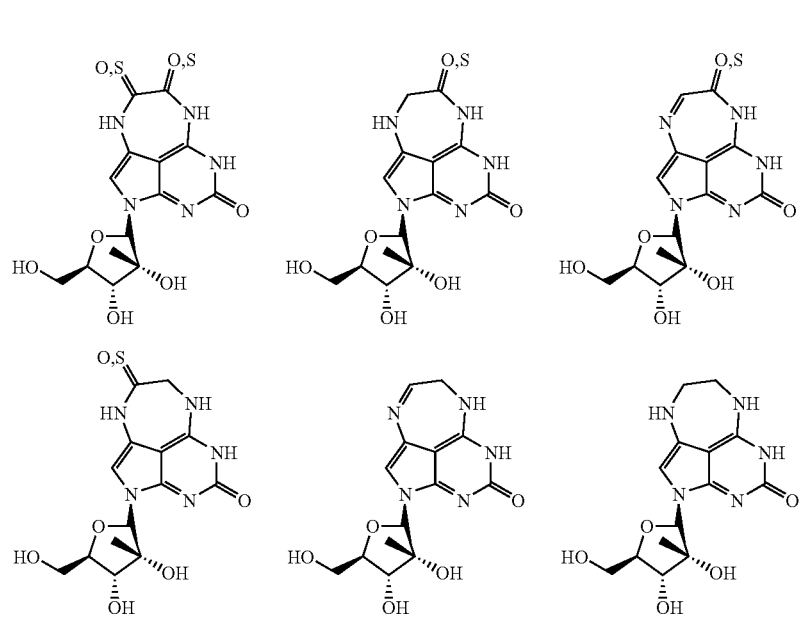
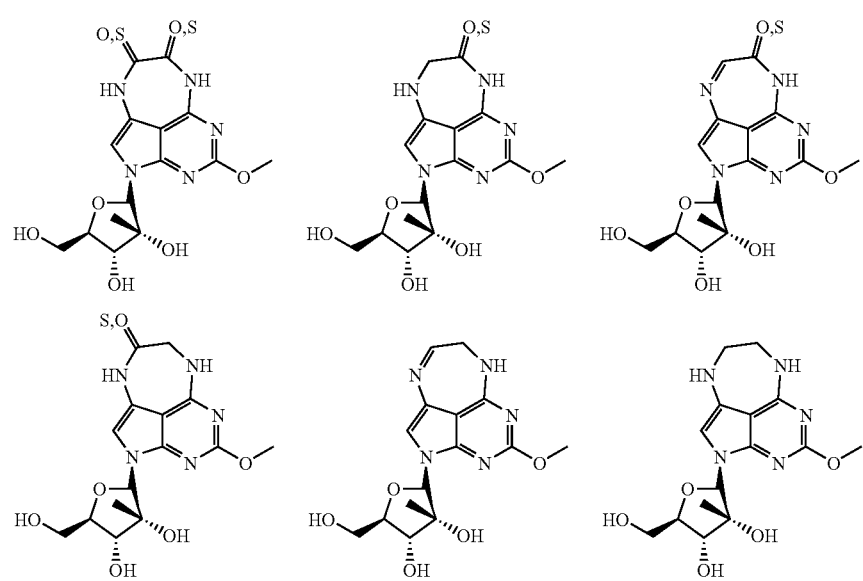

Examples of compounds which can be made by the procedures set forth above include the following:
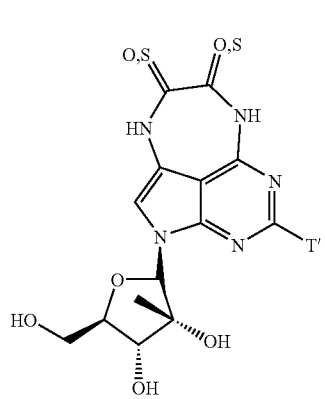
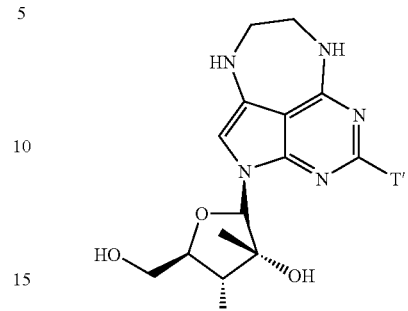
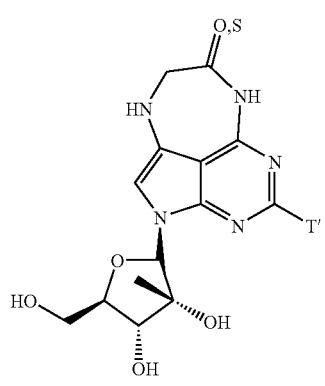
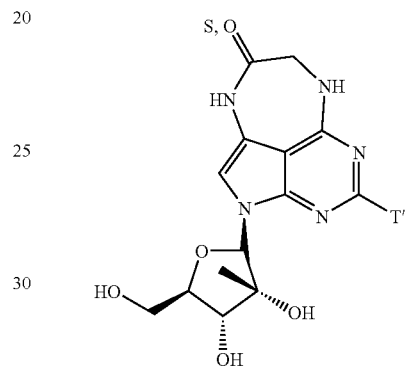
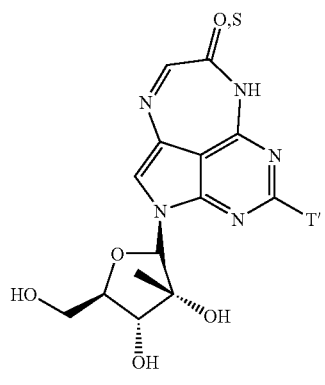
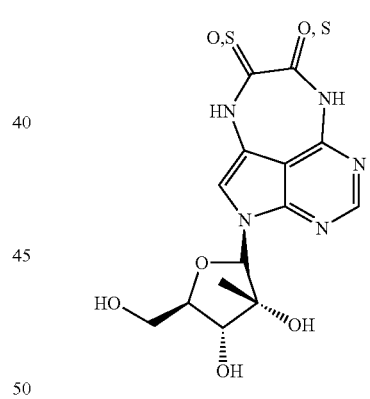
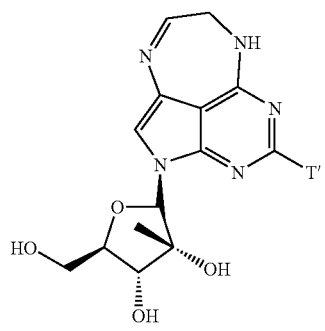
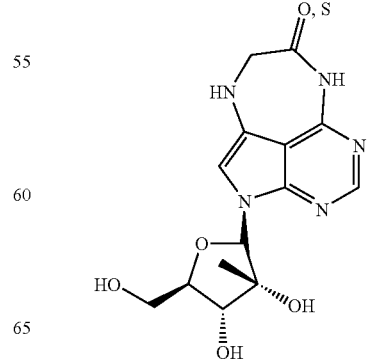

87
-continued
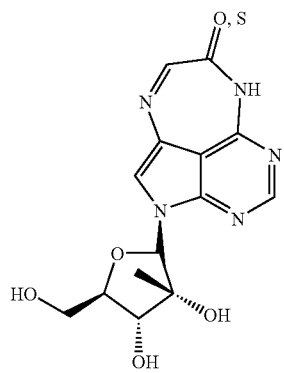
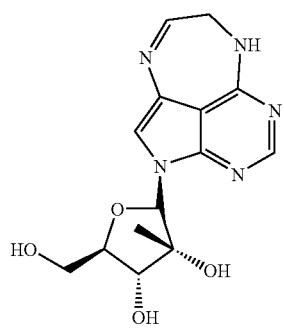
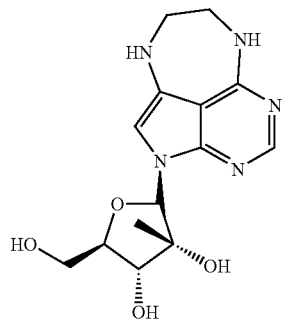
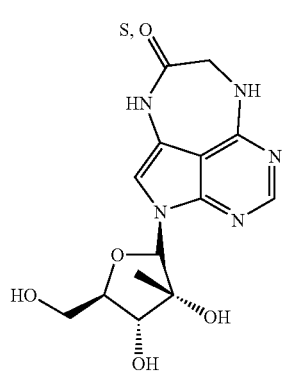
T' =  —O-alkyl
or  —S-alkyl
88
-continued
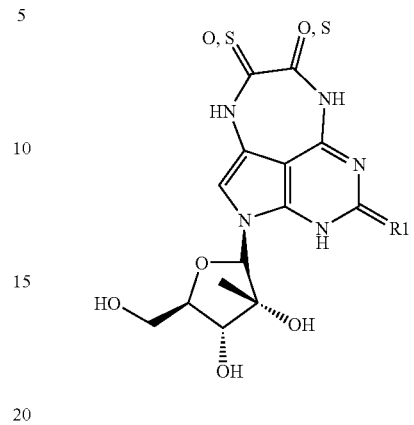
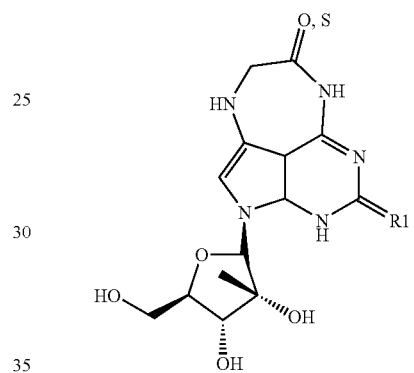
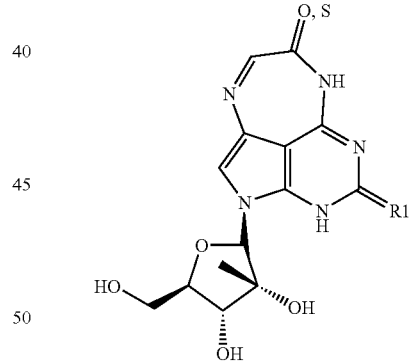
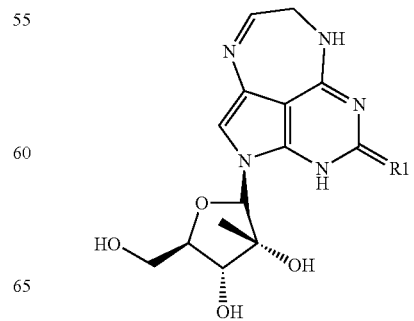

-continued

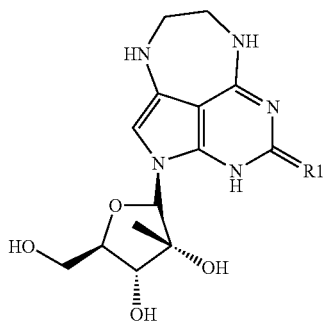

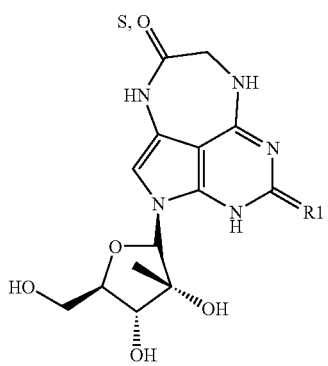

R1 = ═O or ═S

Formation of sugar a in Scheme 9 above where Ph is phenyl and X is a suitable leaving group such as halo, is accomplished as described by Mandal, S. B., et al., *Synth. Commun.*, 1993, 9, page 1239, starting from commercial D-ribose. Protection of the hydroxyl groups to form sugar b is described in Witty, D. R., et al., *Tet. Lett.*, 1990, 31, page 4787. Sugar c and d are prepared using the method of Ning, J. et al., *Carbohydr. Res.*, 2001, 330, page 165, and methods described herein. Sugar e is prepared by using a modification of the Grignard reaction with $CH_3MgBr$ or other appropriate organometallic as described herein (with no titanium/cerium needed). Finally the halogenated sugar (X=halo) used in the subsequent coupling reaction is prepared using the same protection method as used in to make sugar b above. The halogenation is described in Seela.[13]

Subsequently, any of the described nucleosides can be deprotected by methods well known to those skilled in the art, as taught by Greene et al. *Protective Groups in Organic Synthesis*, Jon Wiley and Sons, Second Edition, 1991.

An alternative approach to making protected sugars useful for coupling to heterocyclic bases is detailed in Scheme 10 below.

The following schemes illustrate methods for preparing the sugars used in the methods described above.

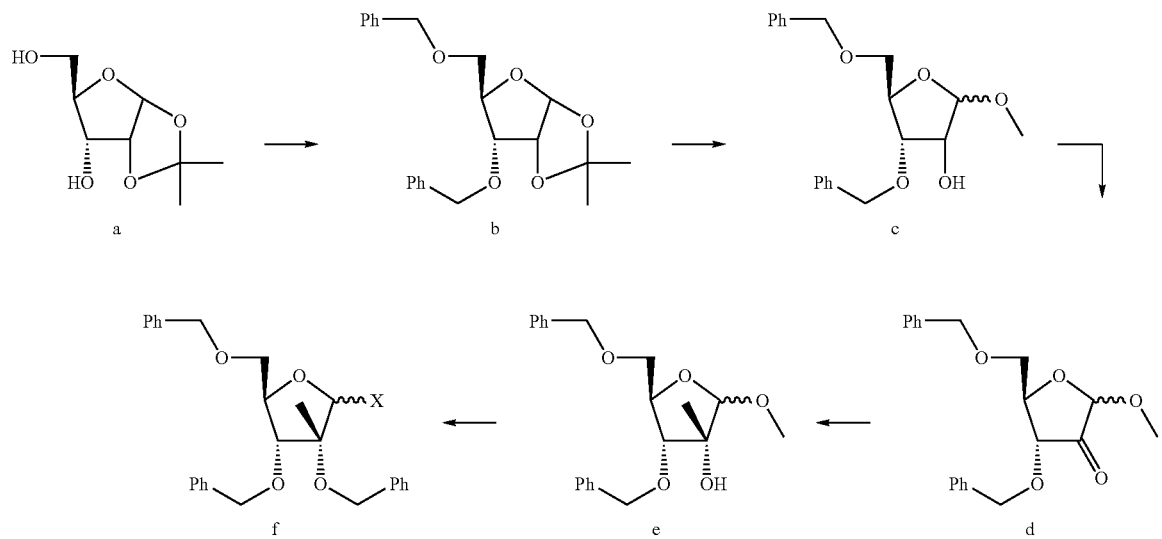

Scheme 9

Scheme 10

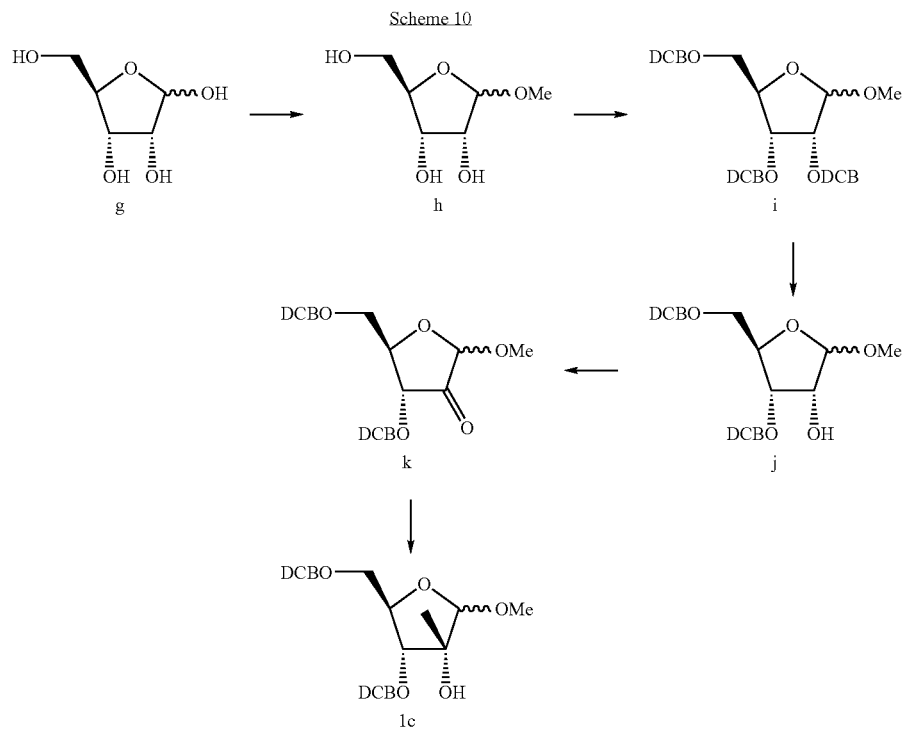

In Scheme 10, methylation of the hydroxyl group of compound g proceeds via conventional methodology to provide for compound h. The 2, 3 and 5 hydroxyl groups of the compound h are each protected with 2,4-dichlorobenzyl groups to provide for compound i. Selective deprotection of the 2-(2',4'-dichlorobenzyl) group on compound i proceeds via contact with stannous chloride in a suitable solvent such as methylene chloride, chloroform, and the like at reduced temperatures, e.g., ~0 to 5° C., until reaction completion, e.g., 24-72 hours, to provide for compound j. Oxidation of the 2-hydroxyl group of compound j proceeds as described herein to provide for compound k. Methylation also proceeds as described herein to provide for compound 1c.

In an alternative approach, an appropriately substituted nucleoside with a 2'-OH and 2'-H can be used as the starting material. This nucleoside can be purchased or can be prepared by any known means including standard coupling techniques. The nucleoside can be optionally protected with suitable protecting groups, preferably with acyl, substituted alkyl or silyl groups, by methods well known to those skilled in the art, as taught by Greene et al. *Protective Groups in Organic Synthesis*, John Wiley and Sons, Second Edition, 1991.

The hydroxyl group at the 2' position of the sugar of an otherwise appropriately protected nucleoside can then be oxidized with the appropriate oxidizing agent in a compatible solvent at a suitable temperature to yield the 2'-modified (oxo) sugar. Possible oxidizing agents are, for example, Dess-Martin periodine reagent, $Ac_2O$+DCC in DMSO, Swern oxidation (DMSO, oxalyl chloride, triethylamine), Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$ ruthenium tetroxide, phase transfer catalysts such as chromic acid or permanganate supported on a polymer, $Cl_2$-pyridine, $H_2O_2$-ammonium molybdate, $NaBrO_2$-CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Coupling of an organometallic carbon nucleophile, such as a Grignard reagent, an organolithium, lithium dialkylcopper or $CH_3SiMe_3$ in TBAF with the ketone with the appropriate non-protic solvent at a suitable temperature, yields the alkyl substituted nucleoside. Isolation of the appropriate isomer is conducted as needed.

Subsequently, the nucleoside can be deprotected by methods well known to those skilled in the art, as taught by Greene et al. *Protective Groups in Organic Synthesis*, John Wiley and Sons, Second Edition, 1991.

The present invention is also directed to compounds of Formula I, and Ia to Ic where X is halo, preferably fluoro. Preparation of these compounds is accomplished by forming the desired 2'-fluoro-2'methylribofuranosyl derivative which is subsequently coupled to the desired base. The details for preparing 2'-fluoro-2'methylribofuranosyl derivatives is given in International Patent application with publication number WO 2005 003147 at least on pages 73, and 76 to 79.

In one embodiment of the invention, the D-enantiomers are utilized. However, L-enantiomers are also contemplated to be useful herein. The L-enantiomers corresponding to the compounds of the invention can be prepared following the same foregoing general methods, beginning with the corresponding L-sugar or nucleoside as starting material. In a particular embodiment, the 2'-C-branched ribonucleoside is desired.

Preparation of compounds where W, $W^1$ or $W^2$ is other than hydrogen, using the compounds prepared above as the starting materials, can be accomplished using the methods described in the following reviews of prodrug preparation:

1) Cooperwood, J. S. et al., "*Nucleoside and Nucleotide prodrugs,*" in Ed(s) Chu, C. K. Recent Advances in Nucleosides (2002), 92-147.
2) Zemlicka, J. et al., Biochimica et Biophysica Acta (2002), 158(2-3), 276-286.
3) Wagner, C. et al., Medicinal Research Reviews (2002), 20(6), 417-451.
4) Meier, C. et al., Synlett (1998), (3), 233-242.

For example, conversion of the 5'-hydroxyl group can prepared using the methods describe in D. W. Hutchinson, (Ed. Leroy b. Townsend) "The Synthesis, reaction and Properties of Nucleoside Mono-, Di-, and Triphosphates, and Nucleosides with Changes in the Phosphoryl Residue, "Chemistry of Nucleosides and Nucleotides, Plenum Press, (1991) 2.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of this invention may range from approximately 0.01 to 50 mg per kilogram body weight of the recipient per day; preferably about 0.01-25 mg/kg/day, more preferably about 0.01-10 mg/kg/day, still more preferably from about 0.01 to 5 mg/kg/day. Thus, for administration to a 70 kg person, the dosage range would most preferably be about 0.7-350 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another manner for administering compounds of this invention is inhalation.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145, 684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions may be comprised of a compound of this invention in combination with at least one pharmaceutically acceptable excipient. Acceptable excipients are non-toxic, aid administration, and do not adversely affect the therapeutic benefit of the compound of this invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of this invention based on the total formulation, with the balance being one or more suitable pharmaceutical excipients. Preferably, the compound is present at a level of about 1-80 wt %.

Additionally, the present invention is directed to a pharmaceutical composition comprising a therapeutically effective amount of a compound of the present invention in combination with a therapeutically effective amount of another active agent against RNA-dependent RNA virus and, in particular, against HCV. Agents active against HCV include, but are not limited to, Ribavirin, levovirin, viramidine, thymosin alpha-1, an inhibitor of HCV NS3 serine protease, or an inhibitor of inosine monophosphate dehydrogenase, interferon-$\alpha$, pegylated interferon-$\alpha$ (peginterferon-$\alpha$), a combination of interferon-$\alpha$ and Ribavirin, a combination of peginterferon-$\alpha$ and Ribavirin, a combination of interferon-$\alpha$ and levovirin, and a combination of peginterferon-a and levovirin. Interferon-$\alpha$ includes, but is not limited to, recombinant interferon-$\alpha$2a (such as ROFERON interferon available from Hoffman-LaRoche, Nutley, N.J.), interferon-$\alpha$2b (such as Intron-A interferon available from Schering Corp., Kenilworth, N.J., USA), a consensus interferon, and a purified interferon-$\alpha$ product. For a discussion of Ribavirin and its activity against HCV, see J. O. Saunders and S. A. Raybuck, "Inosine Monophosphate Dehydrogenase: Consideration of Structure, Kinetics and Therapeutic Potential," *Ann. Rep. Med. Chem.,* 35:201-210 (2000).

EXAMPLES

The examples below as well as throughout the application, the following abbreviations have the following meanings. If not defined, the terms have their generally accepted meanings.

Ac$_2$O=acetic anhydride
ACN=acetonitrile
atm=atmospheres
bs=Broad singlet
CAN=ceric ammonium nitrate
cm=Centimeter
d=doublet
dd=Doublet of doublets
DCC=Dicyclohexylcarbodiimide
DCM=dichloromethane
DMEM=Delbecco's minimum eagles medium
DMAP=dimethylaminopyridine
DMF=dimethylformamide
DMSO=Dimethylsulfoxide
DTT=Dithiothreitol
EDTA=ethylene diamine tetraacetic acid
g=Gram
HCV=hepatitis C virus
Hz=hertz
IPTG=Isopropyl β-D-1-thiogalactopyranoside
IU=international units
m=Multiplet
MCPBA=meta-chloroperbenzoic acid
min=minute
M=Molar
mg=Milligram
mL=Milliliter
mM=Millimolar
mmol=Millimole
MS=mass spectrum
m/z=Mass to charge ratio
ng=Nanograms
nm=Nanometers
nM=Nanomolar
N=Normal
NMR=nuclear magnetic resonance
NTP=nucleotide triphosphate
HATU=O-(7-Azabenzotriazol-1-yl)-1,1,3,3-tetramethyluronium hexafluorophosphate
RP-HPLC=reverse phase high performance liquid chromatography
HPLC=high performance liquid chromatography
LC/MS=liquid chromatography mass spectroscopy
s=Singlet
t=triplet
TEA=Triethylamine
TFA=trifluoroacetic acid
THF=Tetrahydrofuran
TLC=thin layer chromatography
T$_m$=Melting temperature
TMS=trimethylsilyl
UTP=uridine triphosphate
μL=Microliters
μg=Micrograms
μM=Micromolar
v/v=volume to volume
wt %=weight percent In addition, all reaction temperatures are in degrees Celsius unless reported otherwise.

In the examples below as well as elsewhere throughout this application, the claimed compounds employ the following numbering system:

I

Example 1

Preparation of 2-(2'-methyl-β-D-ribofuanosyl)-2,6-dihydro-2,3,5,6-tetraaza-benzo[cd]azulen-7-one (Compound 301)

Step 1:

4-Chloro-7H-pyrrolo[2,3-d]pyrimidine 10.75 g (70 mmol) and N-iodosuccinimide (16.8 g, 75 mmol) were dissolved in 400 mL of dry DMF and left at ambient temperature in the darkness over night. The solvent was evaporated. The yellow residue was suspended in hot 10% solution of Na$_2$SO$_3$, filtered, washed twice with hot water and crystallized from ethanol to yield 14.6 g (74.6%) of the title compound as off-white crystals. The mother liquid was evaporated up to ⅓ volume and crystallized again from ethanol to give 2.47 g (12.3%) of the target product. The total yield is close to 100%; T$_m$ 212-214° C. (dec); UV λ$_{max}$: 307, 266, 230, 227 nm (methanol); MS: 277.93 (M–H), 313 (M+Cl); $^1$H-NMR (DMSO-d$_6$): 12.94 (s, 1H, NH), 8.58 (s, 1H, H-2), 7.94 (s, 1H, H-8).

Step 2:

The base, obtained as described above (11.2 g, 40 mmol) was suspended in 500 mL of CH$_3$CN, NaH was added (1.6 g, 40 mmol 60% in oil) and the reaction mixture was stirred at room temperature until NaH was dissolved (about 2 hour).

1—O-Methyl -2-methyl-3,5-bis-O-(2,4-dichlorobenzyl)-β-D-ribofuranose (10 g, 20 mmol) was dissolved in 500 mL of DCM and cooled down to 4 °C. in ice/water bath. $HBr_{(g)}$ was bubbled through the solution for about 30 min. The reaction was monitored by TLC and run until the disappearance of the starting sugar (ether/hexane 1:9 v/v). Upon reaction completion, the solvent was evaporated at the temperature not higher that 20 °C. and kept for 20 min in deep vacuum to remove the traces of HBr. Solution of Na-salt of the base was fast filtrated and the filtrate was added to the sugar component. The reaction was kept overnight at ambient temperature, neutralized with 0.1 N $H_2SO_4$ and evaporated. The residue was distributed between 700 mL of ethyl acetate and 700 mL of water. Organic fraction was washed with water (150 mL), brine (150 mL), dried over $Na_2SO_4$ and evaporated to give semi crystalline mixture. Toluene (500 mL) was added to form light tan precipitate of nonreacted heterocyclic base 2.5 g (25%). Filtrate was concentrated up to the volume of 50 mL and loaded on the glass filter with silica gel (10×10 cm). The filter was washed with 10% ethyl acetate in toluene collecting 500 mL fractions. Fraction 2-4 contained the target compound; fractions 6-7 contained the heterocyclic base.

Fractions 2-4 were evaporated, ether was added to the colorless oil and the mixture was sonicated for 5 min. The off-white precipitate was formed, yield 7.4 g (50%), mother liquid was evaporated and the described procedure was repeated to yield 0.7 g more of the title nucleoside. Total yield is 8.1 g (54.4%); $T_m$: 67-70° C.; $^1$H-NMR (DMSO-$d_6$): δ 8.66 (s, 1H), 8.07 (s, 1H), 7.62-7.34 (m, 6H), 6.22 (s, 1H), 5.64 (s, 1H), 4.78-4.55 (m, 4H), 4.20 (s, 2H), 3.97-3.93 and 3.78-3.75 (dd, 1H), 0.92 (s, 3H); MS: 743.99 (M+H); Recovered base (total): 4 g as off-white crystals; $T_m$ 228-230° C.

Step 3:

To the solution of the compound from the previous step (8 g, 10.7 mmol) in DCM (200 mL) at −78° C. was added boron trichloride (1M in DCM, 88 mL, 88 mmol) dropwise. The mixture was stirred at −78° C. for 2.5 hours and additionally overnight at −20° C. The reaction was quenched by addition of MeOH/DCM (90 mL, 1:1) and the resulting mixture stirred at −20° C. for 30 min, then neutralized by aqueous ammonia at the same temperature. The solid was filtered and washed with methanol/DCM (250 mL, 1:1). The filtrates were combined with 50 mL of silica gel and evaporated up to dryness. Dry silica was loaded on the glass filter with silica gel (10×10 cm). The filter was washed with ethyl acetate collecting 500 mL fractions. Fraction 2-4 contained the target compound. The solvent was evaporated and the residue crystallized from acetone/hexane to give 3.3 g (72%) of title nucleoside; $^1$H-NMR (DMSO-$d_6$): δ 8.84 (s, 1H), 8.20 (s, 1H), 6.21 (s, 1H), 4.00-3.60 (m, sugar), 0.84 (s, 3H); MS: 426.26 (M+H); $T_m$: 182-185° C.

Step 4:

The nucleoside (1.5 g, 3.5 mmol) prepared above was treated with liquid ammonia at 85° C. for 24 hours in the metal pressure reactor. After evaporation of ammonia the residue was dissolved in methanol and co-evaporated with silica gel (about 20 mL). Silica gel bearing the product was on the column (5×10 cm) with silica gel in acetone collecting 50 mL fractions. Fractions 2-8 contained the titled compound. Acetone was evaporated and the residue crystallized from methanol/acetonitrile to give 1.2 g (84%) of the target nucleoside; $T_m$ 220-222° C. (dec); $^1$H-NMR (DMSO-$d_6$): δ8.20 (s, 1H), 7.80 (s, 1H), 6.80-6.50 (bs, 1H), 6.09 (s, 1H), 5.19 (t, 1H, sugar), 5.13-5.11 (m, 2H, sugar), 4.00-3.70 (m, 3H, sugar), 3.60-3.20 (m, 1H, sugar), 0.84 (s, 3H); MS 407.32 (M+H).

Step 5:

To a solution of the product from Example 1, Step 4 (500 mg, 1.232 mmol) was added CuI (46.8 mg, 0.246 mmol), TEA (0.343 mL, 2.464 mmol) and 35 mL of DMF. The mixture was degassed with argon under sonication for 2-3 minutes and Pd(PPh$_3$)$_4$ (142 mg, 0.123 mmol) was added and the reaction mixture was heated to 55° C. for 20 min. Following the 20 min, ethyl propiolate (0.5 mL, 4.9 mL) was added to the reaction mixture every 20 minutes until all the starting material had been consumed, as was monitored by LC/MS. The crude reaction mixture was concentrated and purified on silica gel with methanol/methylene chloride (1:20) as the eluent to afford 600 mg of the target compound.

$^1$H NMR (CD$_3$OD): δ 0.858 (s, 3H), 1.34 (t, 3H), 3.87-4.126 (m, 4H), 4.28 (q, 2H) 6.24 (s, 1H), 8.17 (s, 1H), 8.24 (s, 1H); MS (M+1): 377.1.

Step 6:

To a solution of the product from Example 1, Step 5 (35 mg, 0.093 mmol) in 20 mL ethanol was added 10% palladium on carbon (20 mg). The reaction vessel was flushed with H$_2$ gas and held at 1 atm of H$_2$ via balloon until all starting material had been consumed, as was determined by TLC (24 hours). The palladium catalyst was filtered and the filtrate was concentrated and used directly in Example 1, Step 7.

Step 7:

To the crude material from Example 1, Step 6.(35 mg, 0.093 mmol) was added 0.1M NaOEt (20 mL) and the reaction heated to reflux for 1 hour. The reaction was neutralized with acetic acid, concentrated in vacuo and purified on Phenomenex-C$_{18}$ reverse phase HPLC with a 0-60% B gradient over 20 min at 10 mL/min (Buffer A=H$_2$O, Buffer B=acetonitrile); $^1$H NMR (CD$_3$OD): δ 0.881 (s, 3H), 3.59-4.085 (m, 4H), 5.73 (d, 1H, J=11.4) 6.22 (s, 1H), 7.03 (d, 1H, J=11.4), 7.84 (s, 1H), 8.31 (s, 1H); MS (M+1): 333.1.

Example 2

Preparation of 2-(2'-methyl-β-D-ribofuanosyl)-2,6,8,9-tetrahydro-2,3,5,6-tetraaza-benzo[cd]azulen-7-one (Compound 302)

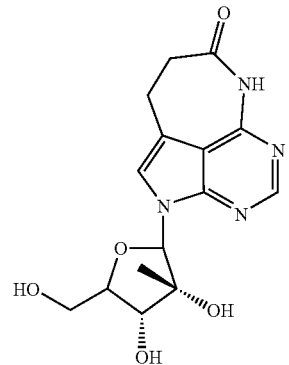

To a solution of the title product from Example 1(10 mg, 0.030 mmol) in ethanol (20 mL) was added 1-2 mg PtO$_2$. The reaction vessel was flushed with H$_2$ gas and held at 1 atm of H$_2$ via balloon for 24 hours. The platinum catalyst was filtered and the filtrate was concentrated and the crude product was purified on silica gel methanol/methylene chloride (1:20) as the eluent to afford 4.0 mg of the title compound; $^1$H NMR (CD$_3$OD): δ 0.852 (s, 3H), 2.91-3.03 (m, 4H), 3.61-4.14 (m, 4H), 6.22 (s, 1H), 7.53 (s, 1H), 8.44 (s, 1H); MS (M+1): 335.1.

Example 3

Preparation of 2-(2'-methyl-β-D-ribofuanosyl)-6,7-dihydro-2H-2,3,5,6-tetraaza-benzo[cd]azulene (Compound 303)

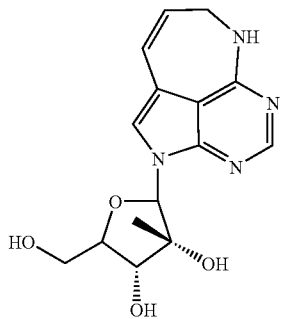

Step 1:

To a solution of the product from Example 1, Step 4 (200 mg, 0.492 mmol) was added CuI (36.5 mg, 0.192 mmol), TEA (.064 mL, 0.46 mmol), 3.2 mL of DMF, and 9.6 mL of THF. The mixture was degassed with argon under sonication for 2-3 minutes and Pd(PPh$_3$)$_4$ (56 mg, 0.048 mmol) and 0.4 mL (2.83 mmol) propyne diethylacetal were added to the reaction mixture which was allowed to stir at room temperature overnight. The following morning an additional 0.4 mL of propyne diethylacetal was added and the reaction was stirred at room temperature for an additional 24 hours. The crude reaction mixture was concentrated and purified on silica gel methanol/methylene chloride (1:4) as the eluent to afford 200 mg; $^1$H NMR (CD$_3$OD): δ 0.84 (s, 3H), 1.25 (t, 6H), 3.66-4.15 (m, 8H), 6.22 (s, 1H), 7.90 (s, 1H), 8.12 (s, 1H); MS (M+1): 407.2.

Step 2:

To a solution of the product from Example 3, Step 1 (50 mg, 0.123 mmol) in 20 mL ACN/H$_2$O (1:1) was added Lindlar's catalyst (2-3 mg). The vessel was flushed with H$_2$ gas and held at 1 atm of H$_2$ via balloon. The reaction was allowed to stir at room temperature until all starting material was consumed, as determined by TLC. The catalyst was filtered and the filtrate was concentrated. The crude product was taken up in acetic acid (1 mL) and was stirred at room temperature for 15 min to liberate the aldehyde. This material was then concentrated in vacuo and MgSO$_4$ (160 mg, 1.33 mmol), NaCNBH$_3$ 1M in THF (0.025 mL, 0.025 mmol) were added and the mixture was heated to 55° C. for 15 min. The MgSO$_4$ was filtered and the filtrate concentrated and purified on Phenomenex-C$_{18}$ reverse phase HPLC with a 0-40% B gradient over 30 min at 10 mL/min (Buffer A=H$_2$O, Buffer B=acetonitrile); $^1$H NMR (CD$_3$OD): δ 0.87 (s, 3H), 3.8-4.13 (m, 6H), 5.76 (dt, 1H, J=11.1 Hz, J=5.4 Hz) 6.20 (s, 1H), 6.66 (dt, 1H, J=11.1, J=1.2), 7.48 (s, 1H), 8.10 (s, 1H); MS (M+1): 319.15.

Example 4

Preparation of 2-(2'-methyl-β-D-ribofuanosyl)-6,9-dihydro-2H-2,3,5,6-tetraaza-benzo[cd]azulene (Compound 304)

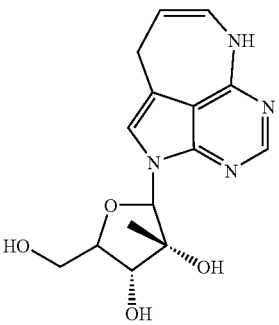

To a solution of the product from Example 3, Step 1 (50 mg, 0.123 mmol) in ethanol (10 mL) was added PtO$_2$ (2-3 mg). The vessel was flushed with H$_2$ gas and held at 1 atm H$_2$ via balloon for 2 hours. The catalyst was filtered and the filtrate was concentrated and the product was purified on Phenomenex-C$_{18}$ reverse phase HPLC with a 0-80% B gradient over 30 min at 10 mL/min (Buffer A=H$_2$O, Buffer B=acetonitrile). The appropriate fractions were concentrated and taken up in 2 mL 70% TFA-water mixture and stirred at 0° C. for 20 min to liberate the aldehyde. The crude product was concentrated and was taken up in acetonitrile (30 mL) and heated to 55° C. for 2 hours. The reaction mixture was concentrated and purified on Phenomenex-C$_{18}$ reverse phase HPLC with a 0-60% B gradient over 30 min at 10 mL/min (Buffer A=H$_2$O, Buffer B=acetonitrile); $^1$H NMR (DMSO-d$_6$): δ 0.68 (s, 3H), 3.48 (m, 2H), 3.63-3.97 (m, 4H), 4.79 (dt, 1H, J=10.8 Hz, J=4.5 Hz) 5.1 (s, 3H), 6.10 (m, 1H), 6.22 (s, 1H), 7.45 (s, 1H), 8.26 (s, 1H), 1H), 9.36 (d, 1H, J=6.3 Hz); MS (M+1): 319.15.

Example 5

Preparation of 2-(2'-methyl-β-D-ribofuanosyl)-6,7,8,9-tetrahydro-2H-2,3,5,6-tetraaza-benzo[cd]azulene (Compound 305)

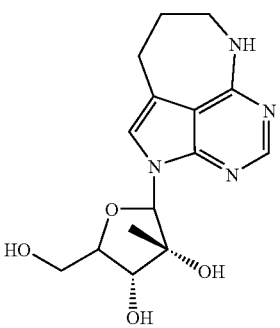

Step 1:

N-trifluoroacetyl propargylamine was synthesized as described in Tetrahedron Lett. 1988, Vol. 29, No. 41 pp. 5221-5224.

Step 2:

To a solution of the product from Example 1, Step 3 (125 mg, 0.294 mmol) in DMF (1.7 mL) and THF (5 mL) was added CuI (4.4 mg, 0.0231 mmol) and TEA (0.25 mL, 1.46 mmol). The mixture was degassed with argon under sonication for 2-3 minutes followed by the addition of $Pd(PPh_3)_2Cl_2$ (4.4 mg, 0.00627 mmol) and 0.6 mL (6.86 mmol) of n-trifluoroacetyl propargylamine. The reaction was allowed to stir at room temperature overnight. The following day, the reaction mixture was concentrated and purified on Phenomenex-$C_{18}$ reverse phase HPLC with a 0-80% B gradient over 30 min at 10 mL/min (Buffer A=$H_2O$, Buffer B=acetonitrile) to afford 100 mg; MS (M+1): 449.09.

Step 3:

To a solution of the product from Example 5, Step 2 (30 mg, 0.0668) in THF (10 mL) was added 1-2 mg $PtO_2$. The vessel was flushed with $H_2$ gas and held at 1 atm of $H_2$ via balloon for 1 hour at room temperature. The catalyst was filtered and the filtrate was concentrated. The residue was taken up in concentrated ammonium (3 mL), stirred at room temperature for 1 hour, and concentrated. The residue was co-evaporated with pyridine (5 mL) 3 times followed by toluene (5 mL) 2 times and taken up in acetonitrile in the presence of molecular sieves. TEA (30 μl) was added and the reaction was heated to 75° C. for 3 hours. The molecular sieves were filtered and the filtrate was concentrated and purified on Phenomenex-$C_{18}$ reverse phase HPLC with a 0-40% B gradient over 30 min at 10 mL/min (Buffer A=$H_2O$, Buffer B=acetonitrile) to afford 8 mg; $^1$H NMR (CD$_3$OD): δ 0.83 (s, 3H), 2.02 (m, 2H), 2.89 (m, 2H), 3.50 (m, 2H), 3.80-4.1 (m, 4H), 6.19 (s, 1H), 7.23 (s, 1H), 8.0 (s, 1H); MS (M+1): 321.17.

Example 6

Preparation of 9-Amino-2-(2'-methyl-β-D-ribofuanosyl)-2,6-dihydro-2,3,5,6-tetraaza-benzo[cd]azulen-7-one (Compound 306)

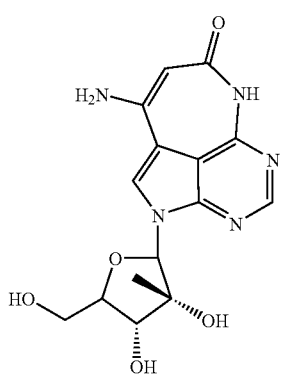

To the product from Example 1, Step 5 (100 mg, 0.266 mmol) was added liquid ammonia (3 mL) which was sealed in an autoclave bomb and heated to 85° C. for 1 hour. The ammonia was allowed to evaporate and the residue was taken up in 0.5 M NaOEt (8.4 mL) and heated to 85° C. overnight. The reaction mixture was concentrated and purified on Phenomenex-$C_{18}$ reverse phase HPLC with a 0-35% B gradient over 30 min at 10 mL/min (Buffer A=$H_2O$, Buffer B=acetonitrile) to afford 22 mg; $^1$H NMR (DMSO-d$_6$): δ 0.756 (s, 3H), 3.74-3.9 (m, 4H), 4.88 (t, 1H), 5.04 (s,1H), 5.24(s, 2H), 6.19 (s, 1H), 6.7 (s, 2H), 7.84 (s, 1H), 8.31 (s, 1H), 10.06 (s,1H); MS (M+1): 348.14.

Example 7

Preparation of 2-(2'-methyl-β-D-ribofuanosyl)-9-methylamino-2,6-dihydro-2,3,5,6-tetraaza-benzo[cd]azulen-7-one (Compound 307)

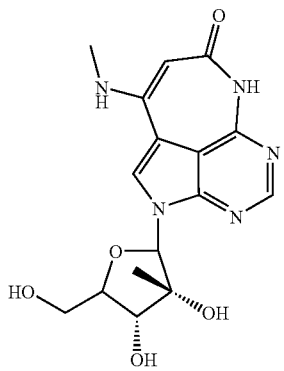

The product from Example 1, Step 5 (225 mg, 0.598 mmol) in methylamine (9 mL, 1 M in THF) was sealed in an autoclave bomb and heated to 80° C. for 1 hour. The reaction mixture was concentrated and the residue was taken up in 11.6 mL of 0.5 M NaOEt and heated to 80° C. for 1 hour. The reaction mixture was concentrated and purified on Phenomenex-$C_{18}$ reverse phase HPLC with a 0-40% B gradient over 20 min at 10 mL/min (Buffer A=$H_2O$, Buffer B=acetonitrile) to afford 110 mg; $^1$H NMR (DMSO-d$_6$): δ 0.76 (s, 3H), 2.82 (d, 3H, J=4.2)3.72-3.98 (m, 4H), 4.81 (d, 1H), 4.88 (t, 1H) 5.24 (d, 1H, J=8.1), 5.25(s, 1H), 6.20 (s, 1H), 7.08 (d, 1H, J=4.8), 7.80 (s, 1H), 8.32 (s, 1H), 10.16 (s, 1H); MS (M+1): 362.15.

Biological Examples

Example 1

Anti-Hepatitis C Activity

Compounds can exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture was disclosed in U.S. Pat. No. 5,738,985 to Miles et al. In vitro assays have been reported in Ferrari et al. Jnl. of Vir., 73:1649-1654, 1999; Ishii et al., Hepatology, 29:1227-1235, 1999; Lohmann et al., Jnl of Bio. Chem., 274:10807-10815, 1999; and Yamashita et al., Jnl. of Bio. Chem., 273:15479-15486, 1998.

WO 97/12033, filed on Sep. 27, 1996, by Emory University, listing C. Hagedorn and A. Reinoldus as inventors, which claims priority to U.S. Provisional Patent Application Ser. No. 60/004,383, filed on Sep. 1995, described an HCV polymerase assay that can be used to evaluate the activity of the of the compounds described herein. Another HCV polymerase assay has been reported by Bartholomeusz, et al., Hepatitis C Virus (HCV) RNA polymerase assay using cloned HCV nonstructural proteins; Antiviral Therapy 1996: 1 (Supp 4) 18-24.

Screens that measure reductions in kinase activity from HCV drugs were disclosed in U.S. Pat. No. 6,030,785, to Katze et al., U.S. Pat. No. 6,228,576, Delvecchio, and U.S.

Pat. No. 5,759,795 to Jubin et al. Screens that measure the protease inhibiting activity of proposed HCV drugs were disclosed in U.S. Pat. No. 5,861,267 to Su et al., U.S. Pat. No. 5,739,002 to De Francesco et al., and U.S. Pat. No. 5,597,691 to Houghton et al.

Example 2

Replicon Assay

A cell line, ET (Huh-lucubineo-ET) was used for screening of compounds for inhibiting HCV RNA dependent RNA polymerase. The ET cell line was stably transfected with RNA transcripts harboring a I 3891uc-ubi-neo/NS3-3'/ET; replicon with firefly luciferase-ubiquitin-neomycin phosphotransferase fusion protein and EMCV-IRES driven NS3-5B polyprotein containing the cell culture adaptive mutations (E1202G; T1280I; K1846T) (Krieger at al, 2001 and unpublished). The ET cells were grown in DMEM, supplemented with 10% fetal calf serum, 2 mM Glutamine, Penicillin (100 IU/mL)/Streptomycin (100 µg/mL), 1× nonessential amino acids, and 250 µg/mL G418 ("Geneticin"). They were all available through Life Technologies (Bethesda, Md.). The cells were plated at 0.5-1.0×104 cells/well in the 96 well plates and incubated for 24 hrs before adding test compound. The compounds were added to the cells to achieve a final concentration of 0.1 nM to 50 µm and a final DMSO concentration of 0.5%. Luciferase activity was measured 48-72 hours later by adding a lysis buffer and the substrate (Catalog number Glo-lysis buffer E2661 and Bright-Glo luciferase system E2620 Promega, Madison, Wis.). Cells should not be too confluent during the assay. Percent inhibition of replication data was plotted relative to no compound control. Under the same condition, cytotoxicity of the compounds was determined using cell proliferation reagent, WST-1(Roche, Germany). The compounds showing antiviral activities, but no significant cytotoxicities were chosen to determine IC50 and TC50. For these determinations, a 10 point, 2-fold serial dilution for each compound was used, which spans a concentration range of 1000 fold. IC50 and TC50 values were calculated by fitting % inhibition at each concentration to the following equation:

% inhibition=$100\%/[(IC50/[I])^b+1]$ where b is Hill's coefficient.

Example 3

Cloning and expression of recombinant HCV-NS5b

The coding sequence of NS5b protein was cloned by PCR from pFKI$_{389}$luc/NS3-3'/ET as described by Lohmann, V., et al. (1999) *Science* 285, 110-113 using the following primers:

The cloned fragment was missing the C terminus 21 amino acid residues. The cloned fragment is inserted into an IPTG-inducible expression plasmid that provides an epitope tag (His)6 at the carboxy terminus of the protein.

The cloned fragment was missing the C terminus 21 amino acid residues. The cloned fragment is inserted into an IPTG-inducible expression plasmid that provides an epitope tag (His)6 at the carboxy terminus of the protein.

The recombinant enzyme was expressed in XL-1 cells and after induction of expression, the protein was purified using affinity chromatography on a nickel-NTA column. Storage condition is 10 mM Tris-HCl pH 7.5, 50 mM NaCl, 0.1 mM EDTA, 1 mM DTT, 20% glycerol at −20° C.

Example 4

HCV-NS5b Enzyme Assay

The polymerase activity was assayed by measuring incorporation of radiolabeled UTP into a RNA product using a biotinylated, heteropolymeric template, which includes a portion of the HCV genome. Typically, the assay mixture (34 µL) contains 10 mM Tris-HCl (pH 7.5), 5 mM MgCl$_2$, 0.2 mM EDTA, 10 mM KCl, 1 unit/µL RNAsin, 1 mM DTT, 10 µM each of NTP, including [$^3$H]-UTP, and 10 ng/µL biotinylated heteropolymeric template. 20× test compound in 2 µl's was then added as a 100% DMSO solution to achieve a final DMSO concentration of 5%. For IC50 determination a 10-point dose response was used. The compounds were serial diluted 2-fold thus covering a range of 1000 fold. Typically for IC50's, compounds were tested starting at 50 uM or 2 µM depending on the potency. Reactions were started with addition of 10× NS5B in 4 µl's and allowed to incubate at 37° C. for 2 hours. Reactions were quenched with 8 µL of 100 mM EDTA and reaction mixtures (30 µL) were transferred to streptavidin-coated scintillation proximity microtiter plates (FlashPlates) and incubated at 4° C. overnight. Incorporation of radioactivity was determined by scintillation counting (cpm). The % Inhibition at a particular concentration was determined using the following equation, % Inhibition=100−[100*(cpm with inhibitor-bg)/(cpm with no inhibitor-bg)]

where bg was the background with no enzyme.

The prodrug compounds of the invention or their metabolites thereof have been found or are contemplated to be active when tested in the aforementioned assays.

Formulation Examples

The following are representative pharmaceutical formulations containing a compound of formula I.

Formulation Example 1

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Formulation Example 2

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Formulation Example 3

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Formulation Example 4

Injectable Formulation

The following ingredients are mixed to form an injectable formulation.

| Ingredient | Amount |
| --- | --- |
| compound of this invention | 0.2 mg–20 mg |
| sodium acetate buffer solution, 0.4 M | 2.0 mL |
| HCl (1N) or NaOH (1N) | q.s. to suitable pH |
| water (distilled, sterile) | q.s. to 20 mL |

Formulation Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Amount |
| --- | --- |
| Compound of the invention | 500 mg |
| Witepsol ® H-15 | balance |

What is claimed is:
1. A compound of Formula I:

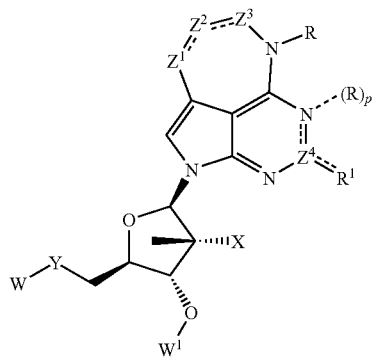

wherein
- ---- between Z and $Z^2$, between $Z^2$ and $Z^3$, between $Z^4$ and $R^1$, and between N and $Z^4$ indicates a bond that may be a single or a double bond and ---- indicates a single bond or no bond, provided that:

only one of the bonds between $Z^1$ and $Z^2$ and between $Z^2$ and $Z^3$ is a double bond;

when the bond between $Z^4$ and $R^1$ is a double bond, the bond between the N and $Z^4$ is a single bond, the bond between the N and $(R)_p$ is a single bond and p is 1;

when the bond between $Z^4$ and $R^1$ is a single bond, the bond between the N and $Z^4$ atoms is a double bond, the bond between the N and $(R)_p$ is absent and p is 0;

p is 0 or 1;

each R is independently selected from hydrogen, alkyl, substituted alkyl, cycloalkyl, substituted cycloalkyl;

when the bond between $Z^4$ and $R^1$ is a single bond, then $R^1$ is selected from the group consisting of hydrogen, alkyl, substituted alkyl, alkoxy, substituted alkoxy, thiol, and alkylthioether;

when the bond between $Z^4$ and $R^1$ is a double bond, then $R^1$ is $Q^1$;

each of $Z^1$, $Z^2$ and $Z^3$ is independently selected from the group consisting of CH, $CH_2$, CH-$Q^4$, C-$Q^4$, C($Q^1$), N, N—H, and N-Q provided that if one of $Z^1$, or $Z^3$ is CH, N or C-$Q^4$ then $Z^2$ is CH or N or C-$Q^4$;

$Z^4$ is a carbon atom containing a double bond either with R' or with N;

Q is selected from the group consisting of alkyl and substituted alkyl;

$Q^1$ is =O or =S;

$Q^3$ is selected from the group consisting of OH, alkyl, substituted alkyl, amino, and substituted amino;

$Q^4$ is selected from the group consisting of halo, cyano, azido, amino, substituted amino, alkyl, substituted alkyl, alkenyl, substituted alkenyl, alkynyl, substituted alkynyl, acyl, acyloxy, carboxyl, carboxyl ester, acylamino, aminoacyl, alkoxy, substituted alkoxy, thiol, alkylthioether and —$SO_2$-$Q^3$;

Y is selected from the group consisting of a bond, —$CH_2$— or —O—;

wherein X is halo and each of W and $W^1$ is independently hydrogen or a pharmaceutically acceptable prodrug group selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate

107 diester, and —C(O)CHR³NHR¹³, where R¹³ is hydrogen and R³ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a sidechain of an amino acid; or R³ and R¹³ together with the carbon and nitrogen atoms bound thereto respectively form a heterocyclic ring;

or pharmaceutically acceptable tautomers, salts or partial salts thereof;

provided that $W^1$ is a pharmaceutically acceptable prodrug group; and further provided that said compound, tautomer, salt, or partial salt is not represented by formula II or III or a tautomer, salt, or partial salt thereof

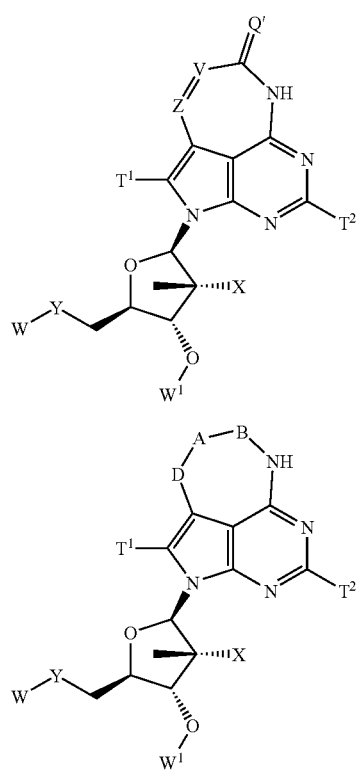

wherein:
Q' is absent or is selected from the group consisting of O, S, and NH, provided that when Q' is absent, V and NH are both attached to a $CH_2$ group;
V is selected from the group consisting of N and C-G;
Z is selected from the group consisting of N and C-G';
V and Z are not identical;
G and G' are independently selected from the group consisting of hydrogen, amino, aminocarbonyl, methylamino, dimethylamino, acylamino, alkoxyamino, —SO₃H, —SO₂NH₂, aminocarbonylamino, oxycarbonylamino, HR'NCHR"C(O)NH—, azido, cyano, halo, hydroxyamino, and hydrazino where R' is hydrogen and R" is a side-chain of an amino acid or where R' and R" together with the nitrogen and carbon bound to each group respectively form a pyrrolidinyl group;
A and B are independently selected from the group consisting of C=Q", NH, and methylene optionally substituted with 1 to 2 halo groups, provided that A and B are not both NH;

108

D is NH, or -D-A-B- together form a —N=CH—NH—, —(C=Q")—CH₂—(C=Q")-, —(C=Q")—NH—(C=Q")-, —(CX')=(CX')—(C=Q")-, or —CH=CH—NH— group where X' is halo;
each Q" is independently selected from the group consisting of O, S, and NH;
$T^1$ is hydrogen;
$T^2$ is selected from the group consisting of hydrogen, $C_1$-$C_4$-alkoxy, and $C_1$-$C_4$alkylthioether; and
W, $W^1$, Y and X are as defined for formula I.

2. A compound of claim 1, wherein the compound is of Formula Ia:

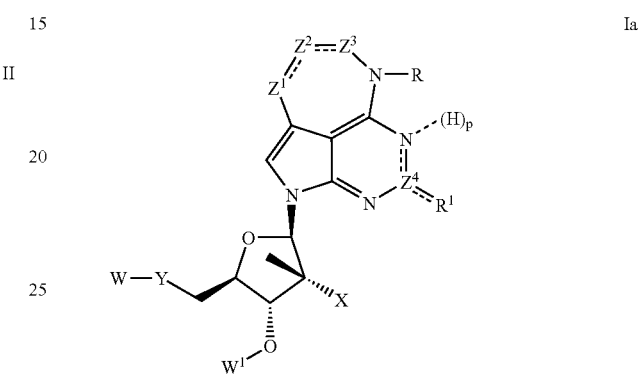

wherein
=== between $Z^1$ and $Z^2$, between $Z^2$ and $Z^3$, between $Z^4$ and $R^1$, and between N and $Z^4$ indicates a bond that may be a single or a double bond and ---- indicates a single bond or no bond, provided that:
only one of the bonds between $Z^1$ and $Z^2$ and between $Z^2$ and $Z^3$ is a double bond;
when the bond between $Z^4$ and $R^1$ is a double bond, the bond between the N and $Z^4$ is a
single bond, the bond between the N and $(H)_p$ is a single bond and p is 1;
when the bond between $Z^4$ and $R^1$ is a single bond, the bond between the N and $Z^4$ atoms is a double bond, the bond between the N and $(H)_p$ is absent and p is 0;
p is 0 or 1;
R is selected from hydrogen, alkyl, substituted alkyl, cycloalkyl, substituted cycloalkyl;
when the bond between $Z^4$ and $R^1$ is a single bond, then $R^1$ is selected from the group consisting of hydrogen, alkyl, substituted alkyl, alkoxy, substituted alkoxy, thiol, alkylthioether;
when the bond between $Z^4$ and $R^1$ is a double bond, then $R^1$ is $Q^1$;
$Z^1$ is selected from the group consisting of CH, $CH_2$, CH-$Q^4$, C-$Q^4$, C($Q^1$), N, NH, N-Q
$Z^2$ is selected from the group consisting of CH, $CH_2$, C($Q^1$);
$Z^3$ is selected from the group consisting of CH, $CH_2$, C($Q^1$);
provided that if $Z^1$ is CH, N or C-$Q^4$ or if $Z^3$ is CH then $Z^2$ is CH;
$Z^4$ is a carbon atom containing a double bond either with $R^1$ or with N;
Q is selected from the group consisting of alkyl and substituted alkyl;
$Q^1$ is =O or =S;

Q⁴ is selected from the group consisting of halo, cyano, azido, amino, substituted amino, alkyl, substituted alkyl, alkenyl, substituted alkenyl, alkynyl, substituted alkynyl, acyl, acyloxy, carboxyl, carboxyl ester, acylamino, aminoacyl, alkoxy, substituted alkoxy, thiol, alkylthioether and —SO₂-Q³, where Q³ is CH, alkyl, substituted alkyl, amino, or substituted amino;

Y is selected from the group consisting of a bond, —CH₂— or —O—; and

X is halo;

each of W, W¹ and W² is independently selected from the group consisting of hydrogen, and a pharmaceutically acceptable prodrug group;

or pharmaceutically acceptable tautomers, salts or partial salts thereof.

3. A compound of claim 1 wherein the compound is of Formula Ib:

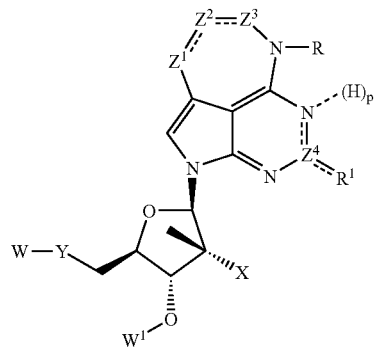

Ib wherein

═══between Z¹ and Z², between Z² and Z³, between Z⁴ and R¹, and between N and Z⁴ indicates a bond that may be a single or a double bond and ---- indicates a single bond or no bond, provided that:

only one of the bonds between Z¹ and Z² and between Z² and Z³ is a double bond;

when the bond between Z⁴ and R¹ is a double bond, the bond between the N and Z⁴ is a single bond, the bond between the N and (H)$_p$ is a single bond and p is 1;

when the bond between Z⁴ and R¹ is a single bond, the bond between the N and Z⁴ atoms is a double bond, the bond between the N and (H)$_p$ is absent, and p is 0;

p is 0 or 1;

R is hydrogen;

when the bond between Z⁴ and R¹ is a single bond, then R¹ is selected from the group consisting of hydrogen, alkyl, alkoxy, and alkylthioether;

when the bond between Z⁴ and R¹ is a double bond, then R¹ is ═O;

Z¹ is selected from the group consisting of CH, CH₂, C-Q⁵, C—CN, C-N₃, C-OH, C-SH, C—O-alkyl, C—S-alkyl, C—SO₂-Q³, CC≡C-Q², C(Q¹); C—NH₂, C—NHCH₃, C—N(CH₃)₂, N, and NH;

Z² is selected from the group consisting of CH, CH₂, C(Q¹);

Z³ is selected from the group consisting of CH, CH₂, C(Q¹);

provided that if Z¹ is CH, C—CN, C—N₃, C—O—C(O)CH₃, C—OH, C—SH, —C—O-alkyl, C—SO₂-Q³, CC≡C-Q², CNH₂, CNHCH₃, C—N(CH₃)₂ or N or if Z³ is CH then Z² is CH;

Z⁴ is a carbon atom containing a double bond either with R¹ or with N;

Q¹ is O or S;

Q² is hydrogen, alkyl;

Q³ is OH, NH₂, or alkyl;

Q⁵ is halo;

Y is selected from the group consisting of a bond, —CH₂— or —O—; and

X is halo;

each of W, W¹ and W² is independently selected from the group consisting of hydrogen, and a pharmaceutically acceptable prodrug group;

or pharmaceutically acceptable tautomers, salts or partial salts thereof.

4. A compound of claim 1 wherein the compound is of Formula Ic:

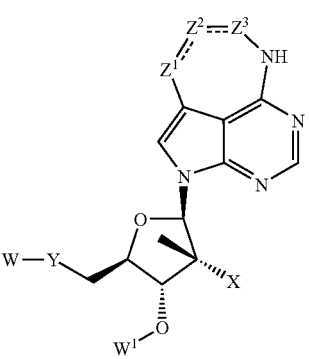

Ic wherein

═══between Z¹ and Z², between Z² and Z³, between Z⁴ and R¹, and between N and Z⁴ indicates a bond that may be a single or a double bond and ---- indicates a single bond or no bond, provided that:

only one of the bonds between Z¹ and Z² and between Z² and Z³ is a double bond;

Z¹ is selected from the group consisting of CH, CH₂, C—NH₂, C—NHCH₃;

Z² is selected from the group consisting of CH, CH₂;

Z³ is selected from the group consisting of CH, CH₂, C(O);

provided that if Z¹ is CH, C—NH₂ or C—NHCH₃, then Z² is CH and Z³ is not CH;

Y is selected from the group consisting of a bond, —CH₂— or —O—; and

X is halo;

each of W, W¹ and W² is independently selected from the group consisting of hydrogen, and a pharmaceutically acceptable prodrug group;

or pharmaceutically acceptable tautomers, salts or partial salts thereof.

5. The compound according to claim 1, wherein X is F.

6. A compound according to claim 5 wherein W is hydrogen, phospho, diphospho, or triphospho.

7. A compound according to claim 5 wherein W is represented by the formula:

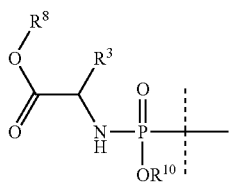

wherein
R³ is a sidechain of an amino acid;
R⁸ is hydrogen or alkyl; and
R¹⁰ is selected from the group consisting of alkyl, substituted alkyl, aryl, substituted aryl, cycloalkyl, substituted cycloalkyl, heteroaryl, substituted heteroaryl, heterocyclic and substituted heterocyclic.

8. A compound according to claim 5 wherein W¹ is represented by the formula:

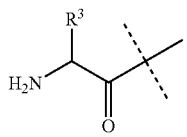

where R³ is a sidechain of an amino acid.

9. A compound of Formula I:

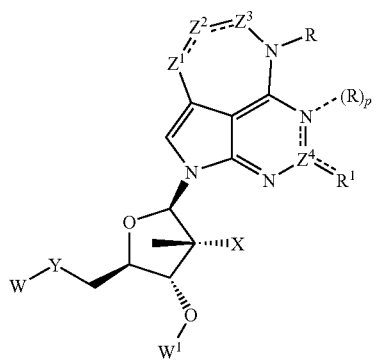

I wherein
----between Z and Z², between Z² and Z³, between Z⁴ and R¹, and between N and Z⁴ indicates a bond that may be a single or a double bond and ----indicates a single bond or no bond, provided that:
only one of the bonds between Z¹ and Z² and between Z² and Z³ is a double bond;
when the bond between Z⁴ and R¹ is a double bond, the bond between the N and Z⁴ is a single bond, the bond between the N and (R)$_p$ is a single bond and p is 1;
when the bond between Z⁴ and R¹ is a single bond, the bond between the N and Z⁴ atoms is a double bond, the bond between the N and (R)$_p$ is absent and p is 0;
p is 0 or 1;
each R is independently selected from hydrogen, alkyl, substituted alkyl, cycloalkyl, substituted cycloalkyl, when the bond between Z⁴ and R¹ is a single bond, then R¹ is selected from the group consisting of hydrogen, alkyl, substituted alkyl, alkoxy, substituted alkoxy, thiol, and alkylthioether;
when the bond between Z⁴ and R¹ is a double bond, then R¹ is Q¹;
each of Z¹, Z² and Z³ is independently selected from the group consisting of CH, CH₂, CH-Q⁴, C-Q⁴, C(Q¹), N, N—H, and N-Q provided that if one of Z¹, or Z³ is CH, N or C-Q⁴ then Z² is CH or N or C-Q⁴;
Z⁴ is a carbon atom containing a double bond either with R' or with N;
Q is selected from the group consisting of alkyl and substituted alkyl;
Q¹ is =O or =S;
Q³ is selected from the group consisting of OH, alkyl, substituted alkyl, amino, and substituted amino;
Q⁴ is selected from the group consisting of halo, cyano, azido, amino, substituted amino, alkyl, substituted alkyl, alkenyl, substituted alkenyl, alkynyl, substituted alkynyl, acyl, acyloxy, carboxyl, carboxyl ester, acylamino, aminoacyl, alkoxy, substituted alkoxy, thiol, alkylthioether and —SO₂-Q³;
Y is selected from the group consisting of a bond, —CH₂— or —O—;
wherein X is O—W² and wherein W¹ is methyl and each of W and W² is independently hydrogen or a pharmaceutically acceptable prodrug group selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and C(O)CHR³NHR¹³, where R¹³ is hydrogen and R³ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a sidechain of an amino acid; or R³ and R¹³ together with the carbon and nitrogen atoms bound thereto respectively form a heterocyclic ring;
or pharmaceutically acceptable tautomers, salts or partial salts thereof;
provided that W² is a pharmaceutically acceptable prodrug group; and
further provided that said compound, tautomer, salt, or partial salt is not represented by formula II or III or a tautomer, salt, or partial salt thereof

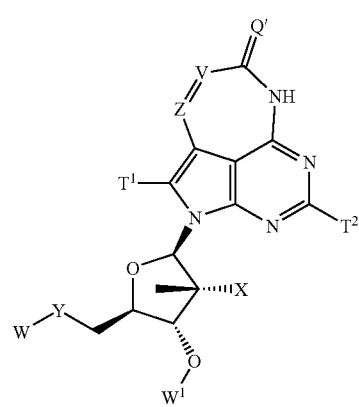

II

-continued

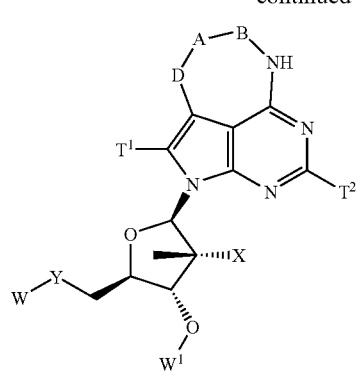

III wherein:
Q' is absent or is selected from the group consisting of O, S, and NH, provided that when Q' is absent, V and NH are both attached to a $CH_2$ group;
V is selected from the group consisting of N and C-G;
Z is selected from the group consisting of N and C-G';
V and Z are not identical;
G and G' are independently selected from the group consisting of hydrogen, amino, aminocarbonyl, methylamino, dimethylamino, acylamino, alkoxyamino, —$SO_3H$, —$SO_2NH_2$, aminocarbonylamino, oxycarbonylamino, HR'NCHR"C(O)NH—, azido, cyano, halo, hydroxyamino, and hydrazino where R' is hydrogen and R" is a side-chain of an amino acid or where R' and R" together with the nitrogen and carbon bound to each group respectively form a pyrrolidinyl group;
A and B are independently selected from the group consisting of C=Q", NH, and methylene optionally substituted with 1 to 2 halo groups, provided that A and B are not both NH;
D is NH, or -D-A-B- together form a —N=CH—NH—, -(C=Q")—$CH_2$—(C=Q")-, -(C=Q")—NH—(C=Q")-, —(CX')=(CX')—(C=Q")-, or —CH=CH—NH— group where X' is halo;
each Q" is independently selected from the group consisting of O, S, and NH;
$T^1$ is hydrogen;
$T^2$ is selected from the group consisting of hydrogen, $C_1$-$C_4$-alkoxy, and $C_1$-$C_4$alkylthioether; and
W, $W^1$, Y and X are as defined for formula I.

10. A compound according to claim 9 wherein W is hydrogen, phospho, diphospho, or triphospho.

11. A compound according to claim 9 wherein W is represented by the formula:

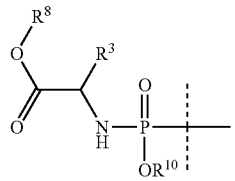

wherein
$R^3$ is a sidechain of an amino acid;
$R^8$ is hydrogen or alkyl; and
$R^{10}$ is selected from the group consisting of alkyl, substituted alkyl, aryl, substituted aryl, cycloalkyl, substituted cycloalkyl, heteroaryl, substituted heteroaryl, heterocyclic and substituted heterocyclic.

12. A compound of Formula I:

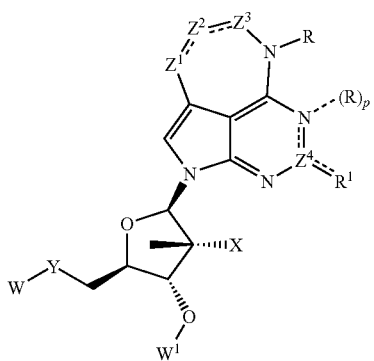

I wherein
---- between Z and $Z^2$, between $Z^2$ and $Z^3$, between $Z^4$ and $R^1$, and between N and $Z^4$ indicates a bond that may be a single or a double bond and ---- indicates a single bond or no bond, provided that:
only one of the bonds between $Z^1$ and $Z^2$ and between $Z^2$ and $Z^3$ is a double bond;
when the bond between $Z^4$ and $R^1$ is a double bond, the bond between the N and $Z^4$ is a single bond, the bond between the N and $(R)_p$ is a single bond and p is 1;
when the bond between $Z^4$ and $R^1$ is a single bond, the bond between the N and $Z^4$ atoms is a double bond, the bond between the N and $(R)_p$ is absent and p is 0;
p is 0 or 1;
each R is independently selected from hydrogen, alkyl, substituted alkyl, cycloalkyl, substituted cycloalkyl;
when the bond between $Z^4$ and $R^1$ is a single bond, then $R^1$ is selected from the group consisting of hydrogen, alkyl, substituted alkyl, alkoxy, substituted alkoxy, thiol, and alkylthioether;
when the bond between $Z^4$ and $R^1$ is a double bond, then $R^1$ is $Q^1$;
each of $Z^1$, $Z^2$ and $Z^3$ is independently selected from the group consisting of CH, $CH_2$, CH-$Q^4$, C-$Q^4$, C($Q^1$), N, N—H, and N-Q provided that if one of $Z^1$, or $Z^3$ is CH, N or C-$Q^4$ then $Z^2$ is CH or N or C-$Q^4$;
$Z^4$ is a carbon atom containing a double bond either with R' or with N;
Q is selected from the group consisting of alkyl and substituted alkyl;
$Q^1$ is =O or =S;
$Q^3$ is selected from the group consisting of OH, alkyl, substituted alkyl, amino, and substituted amino;
$Q^4$ is selected from the group consisting of halo, cyano, azido, amino, substituted amino, alkyl, substituted alkyl, alkenyl, substituted alkenyl, alkynyl, substituted alkynyl, acyl, acyloxy, carboxyl, carboxyl ester, acylamino, aminoacyl, alkoxy, substituted alkoxy, thiol, alkylthioether and —$SO_2Q^3$;
Y is selected from the group consisting of a bond, —$CH_2$— or —O—;
wherein X is O—$W^2$ and wherein W is methyl and each of $W^1$ and $W^2$ is independently hydrogen or a pharmaceutically acceptable prodrug group selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR³NHR¹³, where R¹³ is hydrogen and R³ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a sidechain of an amino acid; or R³ and R¹³ together with the carbon and nitrogen atoms bound thereto respectively form a heterocyclic ring;

or pharmaceutically acceptable tautomers, salts or partial salts thereof;

provided that W¹ is a pharmaceutically acceptable prodrug group; and further provided that said compound, tautomer, salt, or partial salt is not represented by formula II or III or a tautomer, salt, or partial salt thereof

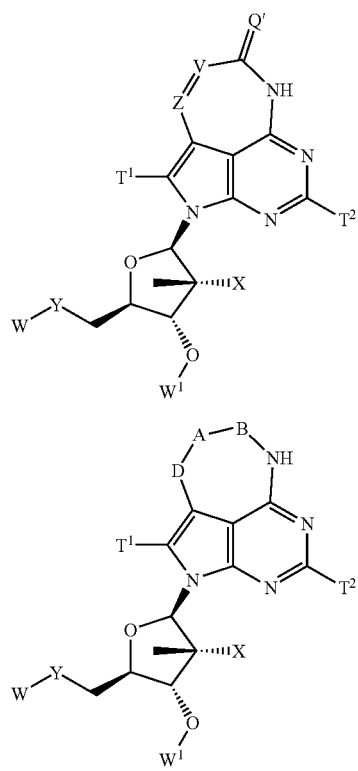

wherein:
Q' is absent or is selected from the group consisting of O, S, and NH, provided that when Q' is absent, V and NH are both attached to a CH₂ group;

V is selected from the group consisting of N and C-G;

Z is selected from the group consisting of N and C-G';

V and Z are not identical;

G and G' are independently selected from the group consisting of hydrogen, amino, aminocarbonyl, methylamino, dimethylamino, acylamino, alkoxyamino, —SO₃H, —SO₂NH₂, aminocarbonylamino, oxycarbonylamino, HR'NCHR"C(O)NH—, azido, cyano, halo, hydroxyamino, and hydrazino where R' is hydrogen and R"is a side-chain of an amino acid or where R' and R" together with the nitrogen and carbon bound to each group respectively form a pyrrolidinyl group;

A and B are independently selected from the group consisting of C=Q", NH, and methylene optionally substituted with 1 to 2 halo groups, provided that A and B are not both NH:

D is NH, or -D-A-B- together form a —N=CH—NH—, —(C=Q")—CH₂—(C=Q")-, —(C=Q")-NH—(C=Q")-, —(CX')=(CX')-(C=Q")-, or —CH=CH—NH— group where X' is halo; each Q" is independently selected from the group consisting of O, S, and NH;

T¹ is hydrogen;

T² is selected from the group consisting of hydrogen, C₁-C₄-alkoxy, and C₁-C₄alkylthioether; and W, W¹, Y and X are as defined for formula I.

13. A compound according to claim 12 wherein W¹ is represented by the formula:

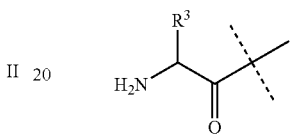

where R³ is a sidechain of an amino acid.

14. A pharmaceutical composition comprising a pharmaceutically acceptable diluent and a therapeutically effective amount of a compound or a mixture of one or more of such compounds as defined in claim 1.

15. A pharmaceutical composition according to claim 14, wherein said composition further comprises a therapeutically effective amount of one or more agents active against HCV.

16. The pharmaceutical composition according to claim 15, wherein said one or more agents is/are selected from the group consisting of Ribavirin, viramidine, levovirin, thymosin alpha-1, an inhibitor of NS3 serine protease, and inhibitor of inosine monophosphate dehydrogenase, interferon-alpha or pegylated interferon-alpha, either alone or in combination with Ribavirin or levovirin.

17. The pharmaceutical composition according to claim 16, wherein said one or more agents is/are interferon-alpha or pegylated interferon-alpha alone or in combination with viramidine, ribavirin or levovirin.

18. A method for treating a viral infection in a mammal which infection is mediated at least in part by a virus in the Flaviviridae family of viruses which method comprises administering to said mammal that has been diagnosed with said viral infection a pharmaceutical composition according to claim 15.

19. The method according to claim 18 wherein said virus is hepatitis C virus.

20. The method according to claim 19 wherein said pharmaceutical composition further comprises a therapeutically effective amount of one or more agents active against HCV.

21. The method according to claim 20 wherein said one or more agents is/are selected from the group consisting of Ribavirin, levovirin, viramidine, thymosin alpha-1, an inhibitor of NS3 serine protease, and inhibitor of inosine monophosphate dehydrogenase, interferon-alpha, pegylated interferon-alpha, alone or in combination with viramidine, Ribavirin or levovirin.

22. The method according to claim 21 wherein said one or more agents is/are interferon-alpha or pegylated interferon-alpha alone or in combination with viramidine, Ribavirin or levovirin.

23. A pharmaceutical composition comprising a pharmaceutically acceptable diluent and a therapeutically effective amount of a compound or a mixture of one or more of such compounds as defined in claim 9.

24. A pharmaceutical composition according to claim 23, wherein said composition further comprises a therapeutically effective amount of one or more agents active against HCV.

25. The pharmaceutical composition according to claim 24, wherein said one or more agents is/are selected from the group consisting of Ribavirin, viramidine, levovirin, thymosin alpha-1, an inhibitor of NS3 serine protease, and inhibitor of inosine monophosphate dehydrogenase, interferon-alpha or pegylated interferon-alpha, either alone or in combination with Ribavirin or levovirin.

26. A method for treating a viral infection in a mammal which infection is mediated at least in part by a virus in the Flaviviridae family of viruses which method comprises administering to said mammal that has been diagnosed with said viral infection a pharmaceutical composition according to claim 23.

27. The method according to claim 26 wherein said virus is hepatitis C virus.

28. A pharmaceutical composition comprising a pharmaceutically acceptable diluent and a therapeutically effective amount of a compound or a mixture of one or more of such compounds as defined in claim 12.

29. A pharmaceutical composition according to claim 28, wherein said composition further comprises a therapeutically effective amount of one or more agents active against HCV.

30. The pharmaceutical composition according to claim 29, wherein said one or more agents is/are selected from the group consisting of Ribavirin, viramidine, levovirin, thymosin alpha-1, an inhibitor of NS3 serine protease, and inhibitor of inosine monophosphate dehydrogenase, interferon-alpha or pegylated interferon-alpha, either alone or in combination with Ribavirin or levovirin.

31. A method for treating a viral infection in a mammal which infection is mediated at least in part by a virus in the Flaviviridae family of viruses which method comprises administering to said mammal that has been diagnosed with said viral infection a pharmaceutical composition according to claim 28.

32. The method according to claim 31 wherein said virus is hepatitis C virus.

\* \* \* \* \*